United States Patent
Hayashi et al.

(10) Patent No.: US 10,988,529 B2
(45) Date of Patent: *Apr. 27, 2021

(54) COMBINATION THERAPY

(71) Applicant: Eli Lilly and Company, Indianapolis, IN (US)

(72) Inventors: Mansuo Lu Hayashi, Carmel, IN (US); Michael Carl Irizarry, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 47 days.

This patent is subject to a terminal disclaimer.

(21) Appl. No.: 16/321,278

(22) PCT Filed: Aug. 3, 2017

(86) PCT No.: PCT/US2017/045234
§ 371 (c)(1),
(2) Date: Jan. 28, 2019

(87) PCT Pub. No.: WO2018/031361
PCT Pub. Date: Feb. 15, 2018

(65) Prior Publication Data
US 2019/0161539 A1    May 30, 2019

Related U.S. Application Data

(60) Provisional application No. 62/375,992, filed on Aug. 17, 2016, provisional application No. 62/373,022, filed on Aug. 10, 2016, provisional application No. 62/372,453, filed on Aug. 9, 2016.

(51) Int. Cl.
| | |
|---|---|
| *C07K 16/18* | (2006.01) |
| *A61P 25/28* | (2006.01) |
| *A61K 39/395* | (2006.01) |
| *A61K 38/00* | (2006.01) |
| *A61K 39/00* | (2006.01) |

(52) U.S. Cl.
CPC .......... *C07K 16/18* (2013.01); *A61K 39/3955* (2013.01); *A61P 25/28* (2018.01); *A61K 38/00* (2013.01); *A61K 2039/505* (2013.01); *A61K 2039/507* (2013.01); *A61K 2039/54* (2013.01); *A61K 2039/545* (2013.01); *C07K 2317/24* (2013.01); *C07K 2317/34* (2013.01); *C07K 2317/565* (2013.01); *C07K 2317/92* (2013.01); *C07K 2317/94* (2013.01)

(58) Field of Classification Search
CPC ................ C07K 16/18; C07K 2317/51; C07K 2317/515; C07K 2317/56; C07K 2317/565; C07K 2317/76; C07K 2317/92; A61K 39/3955; A61K 2039/507; A61K 2039/505; A61K 2039/54; A61K 2039/545; A61P 25/28

See application file for complete search history.

(56) References Cited

U.S. PATENT DOCUMENTS

| | | | |
|---|---|---|---|
| 5,445,090 | A | 8/1995 | Conley |
| 5,811,310 | A | 9/1998 | Ghanbali et al. |
| 5,900,461 | A | 5/1999 | Harris |
| 5,932,462 | A | 8/1999 | Harris et al. |
| 6,436,386 | B1 | 8/2002 | Roberts et al. |
| 6,437,025 | B1 | 8/2002 | Harris et al. |
| 6,448,369 | B1 | 9/2002 | Bentley et al. |
| 6,495,659 | B2 | 12/2002 | Bentley et al. |
| 6,514,491 | B1 | 2/2003 | Bentley et al. |
| 6,515,100 | B2 | 2/2003 | Harris |
| 7,161,060 | B1 | 1/2007 | Duff et al. |
| 7,195,761 | B2 | 3/2007 | Holtzman et al. |
| 7,238,788 | B2 | 7/2007 | Lee |
| 7,442,516 | B2 | 10/2008 | Ohno et al. |
| 7,446,180 | B2 | 11/2008 | Novak |
| 8,012,936 | B2 | 9/2011 | Sigurdsson et al. |
| 8,066,999 | B2 | 11/2011 | DeMattos et al. |
| 8,591,894 | B2 | 11/2013 | Holtzman et al. |
| 8,609,097 | B2 | 12/2013 | Bohrmann et al. |
| 8,647,631 | B2 | 2/2014 | Pfeifer et al. |
| 8,679,498 | B2 | 3/2014 | Lu et al. |
| 8,697,076 | B2 | 4/2014 | Binder et al. |
| 8,703,137 | B2 | 4/2014 | Chain |
| 8,771,693 | B2 | 7/2014 | Lu et al. |
| 8,778,343 | B2 | 7/2014 | Kayed |

(Continued)

FOREIGN PATENT DOCUMENTS

| | | |
|---|---|---|
| EP | 0279454 A2 | 8/1988 |
| WO | 2004016655 A1 | 2/2004 |

(Continued)

OTHER PUBLICATIONS

Ivan Aprahamian et al: "New treatment strategies for Alzheimer's disease: is there a hope? Introduction", Indian J Med Res, Oct. 1, 2013 (Oct. 1, 2013), pp. 449-460.

C. J. Lansdall: An effective treatment for Alzheimer's disease must consider both amyloid and tau, Bioscience Horizons, vol. 7, No. 0, Jun. 17, 201, pp. hzu002.

(Continued)

*Primary Examiner* — Kimberly Ballard
(74) *Attorney, Agent, or Firm* — Duane Christopher Marks

(57) ABSTRACT

A method of treating a cognitive or neurodegenerative disease, comprising administering to a patient in need of such treatment an effective amount of an anti-N3pGlu Abeta antibody, an anti-Abeta antibody, or an antibody fragment that binds Amyloid beta and is covalently attached to a polyethylene glycol molecule, in combination with an effective amount of an anti-Tau antibody.

19 Claims, No Drawings
Specification includes a Sequence Listing.

(56) References Cited

U.S. PATENT DOCUMENTS

| | | | |
|---|---|---|---|
| 8,926,974 | B2 | 1/2015 | Griswold-Prenner et al. |
| 8,940,272 | B2 | 1/2015 | Nitsch et al. |
| 8,980,270 | B2 | 3/2015 | Griswold-Prenner et al. |
| 8,980,271 | B2 | 3/2015 | Griswold-Prenner et al. |
| 9,051,367 | B2 | 6/2015 | Griswold-Prenner et al. |
| 9,139,643 | B2 | 9/2015 | Sigurdsson et al. |
| 9,290,567 | B2 | 3/2016 | Bohrmann et al. |
| 9,304,138 | B2 | 4/2016 | Pfeifer et al. |
| 2007/0218491 | A1 | 9/2007 | Vasan et al. |
| 2008/0220449 | A1 | 9/2008 | Vasan et al. |
| 2012/0244174 | A1 | 9/2012 | Chain |
| 2013/0095492 | A1 | 4/2013 | DeBernardis et al. |
| 2013/0295021 | A1 | 11/2013 | Chen et al. |
| 2014/0056901 | A1 | 2/2014 | Agadjanyan et al. |
| 2014/0099303 | A1 | 4/2014 | Griswold-Prenner et al. |
| 2014/0099304 | A1 | 4/2014 | Griswold-Prenner et al. |
| 2014/0161875 | A1 | 6/2014 | Winderickx et al. |
| 2014/0255412 | A1 | 9/2014 | Pfeifer et al. |
| 2014/0294731 | A1 | 10/2014 | Pfeifer et al. |
| 2014/0294839 | A1 | 10/2014 | Kuret et al. |
| 2014/0302046 | A1 | 10/2014 | Sigurdsson |
| 2015/0004169 | A1 | 1/2015 | Kayed |
| 2015/0175682 | A1 | 6/2015 | Pfeifer et al. |
| 2015/0175685 | A1 | 6/2015 | Grueninger et al. |
| 2015/0239963 | A1 | 8/2015 | Griswold-Prenner et al. |
| 2015/0252102 | A1 | 9/2015 | Nitsch et al. |
| 2015/0259406 | A1 | 9/2015 | Pfeifer et al. |

FOREIGN PATENT DOCUMENTS

| | | | | |
|---|---|---|---|---|
| WO | 2005080986 | A1 | 9/2005 | |
| WO | 2010142423 | A1 | 10/2010 | |
| WO | 2010115483 | A2 | 12/2010 | |
| WO | 2010144711 | A2 | 3/2011 | |
| WO | 2012/021469 | A1 | 2/2012 | |
| WO | 2012/021475 | A2 | 2/2012 | |
| WO | 2011026031 | A1 | 4/2012 | |
| WO | 2012045882 | A2 | 4/2012 | |
| WO | 2012049570 | A1 | 4/2012 | |
| WO | 2012106363 | A2 | 8/2012 | |
| WO | 2013007839 | A1 | 1/2013 | |
| WO | 2013041962 | A1 | 3/2013 | |
| WO | 2013050567 | A1 | 4/2013 | |
| WO | 2013059786 | A2 | 4/2013 | |
| WO | 2013096380 | A2 | 6/2013 | |
| WO | 2013151762 | A1 | 10/2013 | |
| WO | 2014008404 | A1 | 1/2014 | |
| WO | 2014016737 | A1 | 1/2014 | |
| WO | 2014200921 | A1 | 1/2014 | |
| WO | 2014028777 | A2 | 2/2014 | |
| WO | 2014031697 | A2 | 2/2014 | |
| WO | 2014059442 | A2 | 4/2014 | |
| WO | 2014096321 | A1 | 6/2014 | |
| WO | 2014100600 | A2 | 6/2014 | |
| WO | 2014165271 | A2 | 10/2014 | |
| WO | WO-2016137811 | A1 * | 9/2016 | ............ A61P 25/00 |

OTHER PUBLICATIONS

S Tomaszewski et al: "Combination Therapy of Anti-Tau and Anti-Amyloid Drugs for Disease Modification in Early-stage Alzheimer 1 s Disease: Socio-economic Considerations Modeled on Treatments for Tuberculosis, HIV/AIDS and Breast Cancer", J Prev Alz Dis, vol. 3, Nov. 27, 2015 (Nov. 27, 2015), pp. 164-172.

Anonymous: Promising New Treatments for Alzheimer's Target Multiple Disease-Related Proteins, May Have Benefits for Several Brain Diseases Drugs Targeting Protein Misfolding May Be Useful Across Neurodegenerative Diseases According to New Results Reported at Alzheimer's Association International Conference 201, Jul. 19, 2015 (2815-87-19).

North et al., A New Clustering of Antibody CDR Loop Conformations, Journal of Molecular Biology, 406:228-256 (2011).

Bird et al. (1988) Science 242:423-426 "Single-Chains anitgen-binding proteins".
Huston et al. (1988) Proc. Natl. Acad. Sci. USA 85:5879-5883.
Holliger, P., et al. (1993) Proc. Natl. Acad. Sci. USA 90:6444-6448.
Poljak, R. J., et al. (1994) Structure 2:1121-1123.
Queen et al. Proc. Natl. Acad. Sci. USA 86:10029-10033 (1988).
Levitt, M., J. Mol. Biol. 168:595-620 (1983).
He, X. Y., et al J. Immunol. 160: 1029-1035 (1998).
Co, M. S., et al., J. Immunol, 148:1149-1154 (1992).
Johnson-Wood, K., et al., Proc. Natl. Acad. Sci. USA (1997). 94:1550-1555.
Bales, K. R., et al. Nature Genet (1997) 17:263-264.
Asuni, et al., J. of Neuroscience (2007) 27(34): 9115-9129.
Ahmed, Z et al., (2014) Acta Neuropathol. 27(5): 667-683.
Braak, H. et al., Acta Neuropathol (1991) 82:239-259.
Billingsley M. et al., Journal of Biochem. (1997) 323:577-591.
Boutajangout, A.et al., Journal of Neurochem. (2011) 118:658-667.
Carmel, G., et al., J. Biol. Chem (1996) 271:32789-32795.
Castillo-Carranza, D., el al., J. of Neuroscience (2014) 34 (12):4260-4272.
Chai X., et al. {2011} J Biol Chem. 30:286(39):34457-67.
Clavaguera, et al. (2009) Nature Cell Biol. 11, 909-913.
Collin, L., et al., Brain (2014} 137: 2834-2846.
Clavaguera, F. et al., (2014} Acta Neuropathol. 127: 299-301.
Clavaguera, F. et al., PNAS (2013), vol. 110, No. 23, 9535-9540.
Frost, B., et al., J. of Biological Chemistry (2009) 284, No. 19, 12845-12852.
Falcon, Bet al., {2015) J Biol Chem. 290(2):1049.
Goedert, M. et al., Trends in Neurosciences (2010) 33: 317-325.
Goedert, M. et al., Neuron (1989) 3: 519-526.
Gotz, J et al., Biochimica et Biophysica Acta (2010) 1802: 860-871.
Gu J., et al., J. of Biol. Chem. (2013) 288:33081-33095.
Golde, T. et al., Neuron (2013) 80:254-256.
Guo J., et al., J. of Biol. Chem. (2011) 286(17):15317-15331.
Gerson, J., et aL Frontiers in Neurology (2013) Vot4, Art.93, 1-10.
Haroutunian, V., et al., Neurobiol. of Aging (2007) 28:1-7.
Hyman, B. et aL, (2012) Alzheimer's Dement. 2012;8(1):1-13.
Ittiner, A., et al., J. of Neurochem. (2015), 10.1111/jnc.12821.
Jicha, G. et al., J. Neurosci. Res. (1999), 55: 713-723.
Jicha, G. et al., (1997) J. Neurosci. Res., 48(2), 128-132.
Jicha, G_ et at, J. Neurochem (1997) 69(5): 2087-2095.
Koerber, J et at, Nature Biotechnology (2013) 31(10) 916--923.
Kfoury, N. et al., J Biol Chem. (2012} 287, No. 23, 19440-19451.
Kontsekova, E. et al., Alzheimer's Research & Therapy (2014) 6:45.
Liu, L. et al., www.plosone.org, (2012) vol. 7, Issue 2, e31302.
Lewis J. et al., (2000) Nat Genet. 25:402-405.
Lichrenberg-Kreg, B. et al., Biochem. (1992) 89:5384-5388.
Nakamura, K. et al., Cell (2012), 149: 232-244.
Otvos, L., et al., J. Neuroscience Res. (1994} 39:669-673.
Polydoro, M. et al., J. Or Neuroscience (2013) 33(33): 13300-13311.
Pooler, A. et al., J. of Comparative Neurology (2013), 521: 4236-4248.
Ramsden, M., et al., (2005) J. Neuroscience. 25: 10637-10647.
Santa-Maria, I. et al., J Biol Chem. (2012) 287, No. 24, 20522-20533.
Saper, C.B. et al., Neuroscience (1987) vol. 23, No. 2, 389-398.
Sanders, D. et al., Neuron (2014), 82:1271-1288.
Santacruz K., et al., {2005) Science. 309(5733):476-81.
Selkoe, D. et aL, (1991) Neuron. 6(4):487--498.
Uboga, N.V., et al., Neurobiol. of Aging (2000) 21:1-10.
Weaver, C., et at, Neurobiol. of Aging (2000) 21:719--727.
Wu J. et al., J Biol Chem. (2013) 288, No. 3, 1856-1870.
Wolozin, B. et al, Science (1986) 232:648-650.
Yanamandra, K. et al., Annals of Clin. and Translational Neurology (2015) 2(3): 278-288.
Yanamandra,. K. et al., Neuron {2013) 80:402-414.
Zetterberg H. et al., (2013) Alzheimer's Res Ther. 5(2):9.
Esteves-Villanueva, J.O., et al., Biochemistry (2015) 20; 54(2): 293-302.
Shahim P., et al., (2014) JAMA Neurology. 71: 684-692.
Harper Biochimica et Biophysica Acta 2010; 1802:785-795.
Tayebati. Mech. Ageing Dev. 2006. 127: 100-8.
Sarter. Neurosci. and Biobehav. Rev. 2004. 28: 645-650.
Anger. Neurotoxicology 1991. 12: 403-13.

* cited by examiner

SEQUENCE LISTING

<160> NUMBER OF SEQ ID NOS: 79

<210> SEQ ID NO 1
<211> LENGTH: 13
<212> TYPE: PRT
<213> ORGANISM: Artificial Sequence
<220> FEATURE:
<223> OTHER INFORMATION: HCDR1 - anti-N3pGlu Antibody (Antibody I and -continued Antibody II)

<400> SEQUENCE: 1

Lys Ala Ser Gly Tyr Thr Phe Thr Asp Tyr Tyr Ile Asn
1               5                   10

<210> SEQ ID NO 2
<211> LENGTH: 17
<212> TYPE: PRT
<213> ORGANISM: Artificial Sequence
<220> FEATURE:
<223> OTHER INFORMATION: HCDR2 - anti-N3pGlu Antibody (Antibody I and
      Antibody II)

<400> SEQUENCE: 2

Trp Ile Asn Pro Gly Ser Gly Asn Thr Lys Tyr Asn Glu Lys Phe Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: HCDR3 - anti-N3pGlu Antibody (Antibody I and
      Antibody II)

<400> SEQUENCE: 3

Thr Arg Glu Gly Glu Thr Val Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: LCDR1 - anti-N3pGlu Antibody (Antibody I and
      Antibody II)

<400> SEQUENCE: 4

Lys Ser Ser Gln Ser Leu Leu Tyr Ser Arg Gly Lys Thr Tyr Leu Asn
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: LCDR2 - anti-N3pGlu Antibody (Antibody II)

<400> SEQUENCE: 5

Tyr Ala Val Ser Lys Leu Asp Ser
1               5

<210> SEQ ID NO 6
<211> LENGTH: 8
<212> TYPE: PRT
<213> ORGANISM: Artificial Sequence
<220> FEATURE:
<223> OTHER INFORMATION: LCDR2 - anti-N3pGlu Antibody (Antibody I)

<400> SEQUENCE: 6

Tyr Asp Val Ser Lys Leu Asp Ser
1               5

<210> SEQ ID NO 7

<211> LENGTH: 9
<212> TYPE: PRT
<213> ORGANISM: Artificial Sequence
<220> FEATURE:
<223> OTHER INFORMATION: LCDR3 - anti-N3pGlu Antibody (Antibody I and Antibody II)

<400> SEQUENCE: 7

Val Gln Gly Thr His Tyr Pro Phe Thr
1               5

<210> SEQ ID NO 8
<211> LENGTH: 115
<212> TYPE: PRT
<213> ORGANISM: Artificial Sequence
<220> FEATURE:
<223> OTHER INFORMATION: HCVR - anti-N3pGlu Antibody (Antibody I and Antibody II)

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Glu Thr Val Tyr Trp Gly Gln Gly Thr Leu Val Thr
            100                 105                 110

Val Ser Ser
        115

<210> SEQ ID NO 9
<211> LENGTH: 112
<212> TYPE: PRT
<213> ORGANISM: Artificial Sequence
<220> FEATURE:
<223> OTHER INFORMATION: LCVR - anti-N3pGlu Antibody (Antibody I)

<400> SEQUENCE: 9

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Phe Gln Gln Arg Pro Gly Gln Ser
        35                  40                  45

Pro Arg Arg Leu Ile Tyr Asp Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

-continued

```
<210> SEQ ID NO 10
<211> LENGTH: 112
<212> TYPE: PRT
<213> ORGANISM: Artificial Sequence
<220> FEATURE:
<223> OTHER INFORMATION: LCVR - anti-N3pGlu Antibody (Antibody II)

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Lys Ser Ser Gln Ser Leu Leu Tyr Ser
            20                  25                  30

Arg Gly Lys Thr Tyr Leu Asn Trp Leu Gln Gln Lys Pro Gly Lys Ala
        35                  40                  45

Pro Lys Leu Leu Ile Tyr Ala Val Ser Lys Leu Asp Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Val Gln Gly
                85                  90                  95

Thr His Tyr Pro Phe Thr Phe Gly Gln Gly Thr Lys Leu Glu Ile Lys
            100                 105                 110

<210> SEQ ID NO 11
<211> LENGTH: 444
<212> TYPE: PRT
<213> ORGANISM: Artificial Sequence
<220> FEATURE:
<223> OTHER INFORMATION: HC - anti-N3pGlu Antibody (Antibody I and
      Antibody II)

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Glu Thr Val Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205
```

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Asp Glu Leu Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly
    435                 440

<210> SEQ ID NO 12
<211> LENGTH: 219
<212> TYPE: PRT
<213> ORGANISM: Artificial Sequence
<220> FEATURE:
<223> OTHER INFORMATION: LC- anti-N3pGlu Antibody (Antibody I)

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Phe Gln Gln Arg Pro Gly Gln Ser
        35                  40                  45

Pro Arg Arg Leu Ile Tyr Asp Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
            85                  90                  95

Thr His Tyr Pro Phe Thr Phe Gly Gln Gly Thr Lys Leu Glu Ile Lys
        100                 105                 110

Arg Thr Val Ala Ala Pro Ser Val Phe Ile Phe Pro Pro Ser Asp Glu
    115                 120                 125

```
Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 13
<211> LENGTH: 219
<212> TYPE: PRT
<213> ORGANISM: Artificial Sequence
<220> FEATURE:
<223> OTHER INFORMATION: LC - anti-N3pGlu Antibody (Antibody II)

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Lys Ser Ser Gln Ser Leu Leu Tyr Ser
            20                  25                  30

Arg Gly Lys Thr Tyr Leu Asn Trp Leu Gln Gln Lys Pro Gly Lys Ala
        35                  40                  45

Pro Lys Leu Leu Ile Tyr Ala Val Ser Lys Leu Asp Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 14
<211> LENGTH: 1332
<212> TYPE: DNA
<213> ORGANISM: Artificial Sequence
<220> FEATURE:
<223> OTHER INFORMATION: Exemplified DNA for Expressing HC of SEQ ID
      NO.11
```

<400> SEQUENCE: 14

```
caggtgcagc tggtgcagtc tggggctgag gtgaagaagc tgggtcctc ggtgaaggtc      60
tcctgcaagg cttctggata caccttcacc gactattata tcaactgggt gcgacaggcc    120
cctggacaag gcttgagtg gatgggatgg atcaaccctg cagtggtaa tacaaagtac     180
aatgagaagt tcaagggcag agtcacgatt accgcggacg aatccacgag cacagcctac   240
atggagctga gcagcctgag atctgaggac acggccgtgt attactgtac aagagaaggc   300
gagacggtct actggggcca gggaaccctg gtcaccgtct cctcagcctc caccaagggc   360
ccatcggtct tccccgctagc accctcctcc aagagcacct ctgggggcac agcggccctg  420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcaccc agacctacat ctgcaacgtg   600
aatcacaagc ccagcaacac caaggtggac aagaaagttg agcccaaatc ttgtgacaaa   660
actcacacat gcccaccgtg cccagcacct gaactcctgg ggggaccgtc agtcttcctc   720
ttccccccaa acccaaggacacccctcatg atctcccgga cccctgaggt cacatgcgtg   780
gtggtggacg tgagccacga agaccctgag gtcaagttca actggtacgt ggacggcgtg   840
gaggtgcata atgccaagac aaagccgcgg gaggagcagt acaacagcac gtaccgtgtg   900
gtcagcgtcc tcaccgtcct gcaccaggac tggctgaatg gcaaggagta caagtgcaag   960
gtctccaaca aagccctccc agcccccatc gagaaaacca tctccaaagc caaagggcag  1020
ccccgagaac acaggtgta caccctgccc ccatcccggg acgagctgac caagaaccag   1080
gtcagcctga cctgcctggt caaaggcttc tatcccagcg acatcgccgt ggagtgggag  1140
agcaatgggc agccggagaa caactacaag accacgcccc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                     1332
```

<210> SEQ ID NO 15
<211> LENGTH: 657
<212> TYPE: DNA
<213> ORGANISM: Artificial Sequence
<220> FEATURE:
<223> OTHER INFORMATION: Exemplified DNA for Expressing LC of SEQ ID NO.12

<400> SEQUENCE: 15

```
gatgttgtga tgactcagtc tccactctcc ctgcccgtca cccttggaca gccggcctcc     60
atctcctgca gtctagtca agcctcctg tacagtcgcg aaaaaccta cttgaattgg      120
tttcagcaga ggccaggcca atctccaagg cgcctaattt atgatgtttc taaactggac    180
tctggggtcc cagacagatt cagcggcagt gggtcaggca ctgatttcac actgaaaatc   240
agcagggtgg aggctgagga tgttggggtt tattactgcg tgcaaggtac acactaccct    300
tcacttttg gccaagggac caagctggag atcaaacgga ccgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
```

```
gtcacccatc agggcctgag ctcgcccgtc acaaagagct tcaacagggg agagtgc      657
```

<210> SEQ ID NO 16
<211> LENGTH: 657
<212> TYPE: DNA
<213> ORGANISM: Artificial Sequence
<220> FEATURE:
<223> OTHER INFORMATION: Exemplified DNA for Expressing LC of SEQ ID
      NO.13

<400> SEQUENCE: 16

```
gacatccaga tgacccagtc tccttccacc ctgtctgcat ctgtaggaga cagagtcacc    60
atcacttgca agtccagtca gagtctcctg tacagtcgcg gaaaaaccta tttgaactgg   120
ctccagcaga aaccagggaa agcccctaag ctcctgatct atgctgtctc caaactggac   180
agtggggtcc catcaaggtt cagcggcagt ggatctggga cagaattcac tctcaccatc   240
agcagcctgc agcctgatga ttttgcaact tattactgcg tgcagggtac acattatcct   300
ttcactttg gccaggggac caagctggag atcaaacgga ccgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgc      657
```

<210> SEQ ID NO 17
<211> LENGTH: 16
<212> TYPE: PRT
<213> ORGANISM: Artificial Sequence
<220> FEATURE:
<223> OTHER INFORMATION: anti-N3pGlu Antibody (LCDR1- B12L/R17L/hE8L)

<400> SEQUENCE: 17

Lys Ser Ser Gln Ser Leu Leu Tyr Ser Arg Gly Lys Thr Tyr Leu Asn
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: anti-N3pGlu Antibody (LCDR2 - B12L/R17L/hE8L)

<400> SEQUENCE: 18

Ala Val Ser Lys Leu Asp Ser
1               5

<210> SEQ ID NO 19
<211> LENGTH: 9
<212> TYPE: PRT
<213> ORGANISM: Artificial Sequence
<220> FEATURE:
<223> OTHER INFORMATION: anti-N3pGlu Antibody (LCDR3 - B12L/R17L/hE8L)

<400> SEQUENCE: 19

Val Gln Gly Thr His Tyr Pro Phe Thr
1               5

<210> SEQ ID NO 20
<211> LENGTH: 10
<212> TYPE: PRT

<210> SEQ ID NO 20
<211> LENGTH: 10
<212> TYPE: PRT
<213> ORGANISM: Artificial Sequence
<220> FEATURE:
<223> OTHER INFORMATION: anti-N3pGlu Antibody (HCDR1 - B12L)

<400> SEQUENCE: 20

Gly Tyr Asp Phe Thr Arg Tyr Tyr Ile Asn
1               5                   10

<210> SEQ ID NO 21
<211> LENGTH: 10
<212> TYPE: PRT
<213> ORGANISM: Artificial Sequence
<220> FEATURE:
<223> OTHER INFORMATION: anti-N3pGlu Antibody (HCDR1 - R17L)

<400> SEQUENCE: 21

Gly Tyr Thr Phe Thr Arg Tyr Tyr Ile Asn
1               5                   10

<210> SEQ ID NO 22
<211> LENGTH: 17
<212> TYPE: PRT
<213> ORGANISM: Artificial Sequence
<220> FEATURE:
<223> OTHER INFORMATION: anti-N3pGlu Antibody   (HCDR2 - B12L/R17L/hE8L)

<400> SEQUENCE: 22

Trp Ile Asn Pro Gly Ser Gly Asn Thr Lys Tyr Asn Glu Lys Phe Lys
1               5                   10                  15

Gly

<210> SEQ ID NO 23
<211> LENGTH: 6
<212> TYPE: PRT
<213> ORGANISM: Artificial Sequence
<220> FEATURE:
<223> OTHER INFORMATION: anti-N3pGlu Antibody (HCDR3 - B12L)

<400> SEQUENCE: 23

Glu Gly Ile Thr Val Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: anti-N3pGlu Antibody   (HCDR3 - R17L)

<400> SEQUENCE: 24

Glu Gly Thr Thr Val Tyr
1               5

<210> SEQ ID NO 25
<211> LENGTH: 112
<212> TYPE: PRT
<213> ORGANISM: Artificial Sequence
<220> FEATURE:
<223> OTHER INFORMATION: anti-N3pGlu Antibody   (LCVR - B12L/R17L)

<400> SEQUENCE: 25

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Leu Leu Gln Lys Pro Gly Gln Ser
            35                  40                  45

Pro Gln Leu Leu Ile Tyr Ala Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

<210> SEQ ID NO 26
<211> LENGTH: 115
<212> TYPE: PRT
<213> ORGANISM: Artificial Sequence
<220> FEATURE:
<223> OTHER INFORMATION: anti-N3pGlu Antibody (HCVR - B12L)

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Thr Arg Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Thr Val Tyr Trp Gly Gln Gly Thr Thr Val Thr
            100                 105                 110

Val Ser Ser
        115

<210> SEQ ID NO 27
<211> LENGTH: 115
<212> TYPE: PRT
<213> ORGANISM: Artificial Sequence
<220> FEATURE:
<223> OTHER INFORMATION: anti-N3pGlu Antibody (HCVR - R17L)

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Thr Val Tyr Trp Gly Gln Gly Thr Thr Val Thr
            100                 105                 110

Val Ser Ser
    115

<210> SEQ ID NO 28
<211> LENGTH: 219
<212> TYPE: PRT
<213> ORGANISM: Artificial Sequence
<220> FEATURE:
<223> OTHER INFORMATION: anti-N3pGlu Antibody (LC - B12L/R17L)

<400> SEQUENCE: 28

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Leu Leu Gln Lys Pro Gly Gln Ser
        35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 29
<211> LENGTH: 444
<212> TYPE: PRT
<213> ORGANISM: Artificial Sequence
<220> FEATURE:
<223> OTHER INFORMATION: anti-N3pGlu Antibody (HC - B12L)

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Thr Arg Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Glu Gly Ile Thr Val Tyr Trp Gly Gln Gly Thr Thr Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
            210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
            435                 440

<210> SEQ ID NO 30
<211> LENGTH: 444
<212> TYPE: PRT
<213> ORGANISM: Artificial Sequence
<220> FEATURE:
<223> OTHER INFORMATION: anti-N3pGlu Antibody (HC - R17L)
```

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Thr Val Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415
```

```
Gln Gly Asn Val Phe Ser Cys Ser Val Met His Glu Ala Leu His Asn
                420                 425                 430

His Tyr Thr Gln Lys Ser Leu Ser Leu Ser Pro Gly
        435                 440

<210> SEQ ID NO 31
<211> LENGTH: 40
<212> TYPE: PRT
<213> ORGANISM: Artificial Sequence
<220> FEATURE:
<223> OTHER INFORMATION: N3pGlu A beta
<220> FEATURE:
<221> NAME/KEY: MOD_RES
<222> LOCATION: (1)..(1)
<223> OTHER INFORMATION: Glu at residue 1 is modified as a pyro-glutamic
      acid

<400> SEQUENCE: 31

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
                20                  25                  30

Met Val Gly Gly Val Val Ile Ala
            35                  40

<210> SEQ ID NO 32
<211> LENGTH: 112
<212> TYPE: PRT
<213> ORGANISM: Artificial Sequence
<220> FEATURE:
<223> OTHER INFORMATION: anti-N3pGlu Antibody(LCVR-hE8L)

<400> SEQUENCE: 32

Asp Ile Val Met Thr Gln Thr Pro Leu Ser Leu Ser Val Thr Pro Gly
1               5                   10                  15

Gln Pro Ala Ser Ile Ser Cys Lys Ser Gln Ser Leu Leu Tyr Ser
                20                  25                  30

Arg Gly Lys Thr Tyr Leu Asn Trp Leu Leu Gln Lys Pro Gly Gln Ser
            35                  40                  45

Pro Gln Leu Leu Ile Tyr Ala Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

<210> SEQ ID NO 33
<211> LENGTH: 219
<212> TYPE: PRT
<213> ORGANISM: Artificial Sequence
<220> FEATURE:
<223> OTHER INFORMATION: anti-N3pGlu Antibody(LC-hE8L)

<400> SEQUENCE: 33

Asp Ile Val Met Thr Gln Thr Pro Leu Ser Leu Ser Val Thr Pro Gly
1               5                   10                  15

Gln Pro Ala Ser Ile Ser Cys Lys Ser Gln Ser Leu Leu Tyr Ser
                20                  25                  30

Arg Gly Lys Thr Tyr Leu Asn Trp Leu Leu Gln Lys Pro Gly Gln Ser
```

```
                35                  40                  45
Pro Gln Leu Leu Ile Tyr Ala Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                     85                  90                  95

Thr His Tyr Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 34
<211> LENGTH: 115
<212> TYPE: PRT
<213> ORGANISM: Artificial Sequence
<220> FEATURE:
<223> OTHER INFORMATION: anti-N3pGlu Antibody (HCVR-hE8L)

<400> SEQUENCE: 34

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
                 20                  25                  30

Tyr Ile Asn Trp Val Arg Gln Ala Pro Gly Gln Gly Leu Glu Trp Met
             35                  40                  45

Gly Trp Ile Asn Pro Gly Ser Gly Asn Thr Lys Tyr Asn Glu Lys Phe
 50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Glu Thr Val Tyr Trp Gly Gln Gly Thr Thr Val Thr
                100                 105                 110

Val Ser Ser
        115

<210> SEQ ID NO 35
<211> LENGTH: 444
<212> TYPE: PRT
<213> ORGANISM: Artificial Sequence
<220> FEATURE:
<223> OTHER INFORMATION: anti-N3pGlu Antibody (HC-hE8L)

<400> SEQUENCE: 35
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
50                      55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Thr Val Tyr Trp Gly Gln Gly Thr Thr Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
```

```
                420                 425                 430
His Tyr Thr Gln Lys Ser Leu Ser Leu Ser Pro Gly
        435                 440

<210> SEQ ID NO 36
<211> LENGTH: 10
<212> TYPE: PRT
<213> ORGANISM: Artificial Sequence
<220> FEATURE:
<223> OTHER INFORMATION: anti-N3pGlu Antibody (HCDR1-hE8L)

<400> SEQUENCE: 36

Gly Tyr Thr Phe Thr Asp Tyr Tyr Ile Asn
1               5                   10

<210> SEQ ID NO 37
<211> LENGTH: 6
<212> TYPE: PRT
<213> ORGANISM: Artificial Sequence
<220> FEATURE:
<223> OTHER INFORMATION: anti-N3pGlu Antibody (HCDR3-hE8L)

<400> SEQUENCE: 37

Glu Gly Glu Thr Val Tyr
1               5

<210> SEQ ID NO 38
<211> LENGTH: 42
<212> TYPE: PRT
<213> ORGANISM: Artificial Sequence
<220> FEATURE:
<223> OTHER INFORMATION: A beta 1-42

<400> SEQUENCE: 38

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 39
<211> LENGTH: 16
<212> TYPE: PRT
<213> ORGANISM: Artificial Sequence
<220> FEATURE:
<223> OTHER INFORMATION: LCDR1 of exemplified anti-A? antibody

<400> SEQUENCE: 39

Arg Ser Ser Gln Ser Leu Ile Tyr Ser Asp Gly Asn Ala Tyr Leu His
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: LCDR2 of exemplified anti-AB antibody

<400> SEQUENCE: 40

Lys Val Ser Asn Arg Phe Ser
1               5

<210> SEQ ID NO 41
<211> LENGTH: 9
```

```
<212> TYPE: PRT
<213> ORGANISM: Artificial Sequence
<220> FEATURE:
<223> OTHER INFORMATION: LCDR3 of exemplified anti-AB antibody

<400> SEQUENCE: 41

Ser Gln Ser Thr His Val Pro Trp Thr
1               5

<210> SEQ ID NO 42
<211> LENGTH: 5
<212> TYPE: PRT
<213> ORGANISM: Artificial Sequence
<220> FEATURE:
<223> OTHER INFORMATION: HCDR1 of exemplified anti-AB antibody

<400> SEQUENCE: 42

Arg Tyr Ser Met Ser
1               5

<210> SEQ ID NO 43
<211> LENGTH: 17
<212> TYPE: PRT
<213> ORGANISM: Artificial Sequence
<220> FEATURE:
<223> OTHER INFORMATION: HCDR2 of exemplified anti-AB antibody

<400> SEQUENCE: 43

Gln Ile Asn Ser Val Gly Asn Ser Thr Tyr Tyr Pro Asp Thr Val Lys
1               5                   10                  15

Gly

<210> SEQ ID NO 44
<211> LENGTH: 3
<212> TYPE: PRT
<213> ORGANISM: Artificial Sequence
<220> FEATURE:
<223> OTHER INFORMATION: HCDR3 of exemplified anti-AB antibody

<400> SEQUENCE: 44

Gly Asp Tyr
1

<210> SEQ ID NO 45
<211> LENGTH: 113
<212> TYPE: PRT
<213> ORGANISM: Artificial Sequence
<220> FEATURE:
<223> OTHER INFORMATION: LCVR of exemplified anti-AB antibody
<220> FEATURE:
<221> NAME/KEY: VARIANT
<222> LOCATION: (2)..(2)
<223> OTHER INFORMATION: Xaa at position 2 is Val or Ile
<220> FEATURE:
<221> NAME/KEY: VARIANT
<222> LOCATION: (7)..(7)
<223> OTHER INFORMATION: Xaa at position 7 is Ser or Thr
<220> FEATURE:
<221> NAME/KEY: VARIANT
<222> LOCATION: (14)..(14)
<223> OTHER INFORMATION: Xaa at position 14 is Thr or Ser
<220> FEATURE:
<221> NAME/KEY: VARIANT
<222> LOCATION: (15)..(15)
<223> OTHER INFORMATION: Xaa at position 15 is Leu or Pro
<220> FEATURE:
<221> NAME/KEY: VARIANT
<222> LOCATION: (30)..(30)
<223> OTHER INFORMATION: Xaa at position 30 is Ile or Val
<220> FEATURE:
```

```
<221> NAME/KEY: VARIANT
<222> LOCATION: (50)..(50)
<223> OTHER INFORMATION: Xaa at position 50 is Arg, Gln, or Lys
<220> FEATURE:
<221> NAME/KEY: VARIANT
<222> LOCATION: (88)..(88)
<223> OTHER INFORMATION: Xaa at position 88 is Val or Leu
<220> FEATURE:
<221> NAME/KEY: VARIANT
<222> LOCATION: (105)..(105)
<223> OTHER INFORMATION: Xaa at position 105 is Gln or Gly
<220> FEATURE:
<221> NAME/KEY: VARIANT
<222> LOCATION: (108)..(108)
<223> OTHER INFORMATION: Xaa at position 108 is Lys or Arg
<220> FEATURE:
<221> NAME/KEY: VARIANT
<222> LOCATION: (109)..(109)
<223> OTHER INFORMATION: Xaa at position 109 is Val or Leu

<400> SEQUENCE: 45

Asp Xaa Val Met Thr Gln Xaa Pro Leu Ser Leu Pro Val Xaa Xaa Gly
1               5                   10                  15

Gln Pro Ala Ser Ile Ser Cys Arg Ser Ser Gln Ser Leu Xaa Tyr Ser
            20                  25                  30

Asp Gly Asn Ala Tyr Leu His Trp Phe Leu Gln Lys Pro Gly Gln Ser
        35                  40                  45

Pro Xaa Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Ser Gln Ser
                85                  90                  95

Thr His Val Pro Trp Thr Phe Gly Xaa Gly Thr Xaa Xaa Glu Ile Lys
            100                 105                 110

Arg

<210> SEQ ID NO 46
<211> LENGTH: 112
<212> TYPE: PRT
<213> ORGANISM: Artificial Sequence
<220> FEATURE:
<223> OTHER INFORMATION: HCVR of exemplified anti-AB antibody
<220> FEATURE:
<221> NAME/KEY: VARIANT
<222> LOCATION: (1)..(1)
<223> OTHER INFORMATION: Xaa at position 1 is Glu or Gln
<220> FEATURE:
<221> NAME/KEY: VARIANT
<222> LOCATION: (7)..(7)
<223> OTHER INFORMATION: Xaa at position 7 is Ser or Leu
<220> FEATURE:
<221> NAME/KEY: VARIANT
<222> LOCATION: (46)..(46)
<223> OTHER INFORMATION: Xaa at position 46 is Glu, Val, Asp or Ser
<220> FEATURE:
<221> NAME/KEY: VARIANT
<222> LOCATION: (63)..(63)
<223> OTHER INFORMATION: Xaa at position 63 is Thr or Ser
<220> FEATURE:
<221> NAME/KEY: VARIANT
<222> LOCATION: (75)..(75)
<223> OTHER INFORMATION: Xaa at position 75 is Ala, Ser, Val or Thr
<220> FEATURE:
<221> NAME/KEY: VARIANT
<222> LOCATION: (76)..(76)
<223> OTHER INFORMATION: Xaa at position 76 is Lys or Arg
<220> FEATURE:
<221> NAME/KEY: VARIANT
<222> LOCATION: (89)..(89)
```

<223> OTHER INFORMATION: Xaa at position 89 is Glu or Asp
<220> FEATURE:
<221> NAME/KEY: VARIANT
<222> LOCATION: (107)..(107)
<223> OTHER INFORMATION: Xaa at position 107 is Leu or Thr

<400> SEQUENCE: 46

Xaa Val Gln Leu Val Glu Xaa Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Xaa Leu Val
        35                  40                  45

Ala Gln Ile Asn Ser Val Gly Asn Ser Thr Tyr Tyr Pro Asp Xaa Val
    50                  55                  60

Lys Gly Arg Phe Thr Ile Ser Arg Asp Asn Xaa Xaa Asn Thr Leu Tyr
65                  70                  75                  80

Leu Gln Met Asn Ser Leu Arg Ala Xaa Asp Thr Ala Val Tyr Tyr Cys
                85                  90                  95

Ala Ser Gly Asp Tyr Trp Gly Gln Gly Thr Xaa Val Thr Val Ser Ser
            100                 105                 110

<210> SEQ ID NO 47
<211> LENGTH: 113
<212> TYPE: PRT
<213> ORGANISM: Artificial Sequence
<220> FEATURE:
<223> OTHER INFORMATION: LCVR of exemplified anti-AB antibody

<400> SEQUENCE: 47

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg

<210> SEQ ID NO 48
<211> LENGTH: 112
<212> TYPE: PRT
<213> ORGANISM: Artificial Sequence
<220> FEATURE:
<223> OTHER INFORMATION: HCVR of exemplified anti-AB antibody

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val

```
                        35                  40                  45
Ala Gln Ile Asn Ser Val Gly Asn Ser Thr Tyr Tyr Pro Asp Thr Val
 50                  55                  60
Lys Gly Arg Phe Thr Ile Ser Arg Asp Asn Ala Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ser Gly Asp Tyr Trp Gly Gln Gly Thr Leu Val Thr Val Ser Ser
                100                 105                 110
```

<210> SEQ ID NO 49
<211> LENGTH: 219
<212> TYPE: PRT
<213> ORGANISM: Artificial Sequence
<220> FEATURE:
<223> OTHER INFORMATION: LC of exemplified anti-AB antibody

<400> SEQUENCE: 49

```
Asp Val Val Met Thr Gln Ser Pro Leu Ser Leu Pro Val Thr Leu Gly
  1               5                  10                  15
Gln Pro Ala Ser Ile Ser Cys Arg Ser Ser Gln Ser Leu Ile Tyr Ser
                 20                  25                  30
Asp Gly Asn Ala Tyr Leu His Trp Phe Leu Gln Lys Pro Gly Gln Ser
             35                  40                  45
Pro Arg Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Ser Gln Ser
                 85                  90                  95
Thr His Val Pro Trp Thr Phe Gly Gln Gly Thr Lys Val Glu Ile Lys
                100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

<210> SEQ ID NO 50
<211> LENGTH: 442
<212> TYPE: PRT
<213> ORGANISM: Artificial Sequence
<220> FEATURE:
<223> OTHER INFORMATION: HC of exemplified anti-AB antibody

<400> SEQUENCE: 50

```
Glu Val Gln Leu Val Glu Ser Gly Gly Gly Leu Val Gln Pro Gly Gly
  1               5                  10                  15
```

-continued

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys

<210> SEQ ID NO 51
<211> LENGTH: 46
<212> TYPE: DNA
<213> ORGANISM: Artificial Sequence
<220> FEATURE:
<223> OTHER INFORMATION: 3' Primer for VL PC

<400> SEQUENCE: 51
tatagagctc aagcttggat ggtgggaaga tggatacagt tggtgc         46

<210> SEQ ID NO 52
<211> LENGTH: 50
<212> TYPE: DNA
<213> ORGANISM: Artificial Sequence
<220> FEATURE:
<223> OTHER INFORMATION: 3' Primer for VH PCR

<400> SEQUENCE: 52
tatagagctc aagcttccag tggatagach gatggggstg tygttttggc     50

<210> SEQ ID NO 53
<211> LENGTH: 112
<212> TYPE: PRT
<213> ORGANISM: Artificial Sequence
<220> FEATURE:
<223> OTHER INFORMATION: LCVR of exemplified PEG-anti-A beta Antibody
      Fragment

<400> SEQUENCE: 53

Asp Ile Val Met Thr Gln Thr Pro Leu Ser Leu Ser Val Thr Pro Gly
1               5                   10                  15

Gln Pro Ala Ser Ile Ser Cys Ser Ser Ser Gln Ser Leu Ile Tyr Ser
            20                  25                  30

Asp Gly Asn Ala Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Thr Gln Ser
                85                  90                  95

Thr His Ser Pro Trp Thr Phe Gly Gly Gly Thr Lys Val Glu Ile Lys
            100                 105                 110

<210> SEQ ID NO 54
<211> LENGTH: 112
<212> TYPE: PRT
<213> ORGANISM: Artificial Sequence
<220> FEATURE:
<223> OTHER INFORMATION: HCVR of exemplified PEG-anti-A beta Antibody
      Fragment
<220> FEATURE:
<221> NAME/KEY: MOD_RES
<222> LOCATION: (56)..(56)
<223> OTHER INFORMATION: Cys at residue 56 is pegylated with a 20KD PEG
      via maleimide linkage

<400> SEQUENCE: 54

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Arg Tyr
            20                  25                  30

```
Ser Met Ser Trp Val Arg Gln Ala Pro Gly Lys Gly Leu Glu Trp Val
        35                  40                  45

Gly Gln Ile Asn Ile Arg Gly Cys Asn Thr Tyr Tyr Pro Asp Thr Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Gly Asp Phe Trp Gly Gln Gly Thr Leu Val Thr Val Ser Ser
            100                 105                 110
```

<210> SEQ ID NO 55
<211> LENGTH: 112
<212> TYPE: PRT
<213> ORGANISM: Artificial Sequence
<220> FEATURE:
<223> OTHER INFORMATION: HCVR of exemplified PEG-anti-A beta Antibody
      Fragment

<400> SEQUENCE: 55

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Arg Tyr
                20                  25                  30

Ser Met Ser Trp Val Arg Gln Ala Pro Gly Lys Gly Leu Glu Trp Val
            35                  40                  45

Gly Gln Ile Asn Ile Arg Gly Asn Asn Thr Tyr Tyr Pro Asp Thr Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Gly Asp Phe Trp Gly Gln Gly Thr Leu Val Thr Val Ser Ser
            100                 105                 110
```

<210> SEQ ID NO 56
<211> LENGTH: 16
<212> TYPE: PRT
<213> ORGANISM: Artificial Sequence
<220> FEATURE:
<223> OTHER INFORMATION: amino acid residues 13-28 of A beta peptide

<400> SEQUENCE: 56

```
His His Gln Lys Leu Val Phe Phe Ala Glu Asp Val Gly Ser Asn Lys
1               5                   10                  15
```

<210> SEQ ID NO 57
<211> LENGTH: 15
<212> TYPE: PRT
<213> ORGANISM: Artificial Sequence
<220> FEATURE:
<223> OTHER INFORMATION: amino acid residues 14-28 of A beta peptide

<400> SEQUENCE: 57

```
His Gln Lys Leu Val Phe Phe Ala Glu Asp Val Gly Ser Asn Lys
1               5                   10                  15
```

<210> SEQ ID NO 58
<211> LENGTH: 16
<212> TYPE: PRT
<213> ORGANISM: Artificial Sequence

```
<220> FEATURE:
<223> OTHER INFORMATION: LCDR1 of exemplified PEG-anti-A beta Antibody
      Fragment

<400> SEQUENCE: 58

Ser Ser Ser Gln Ser Leu Ile Tyr Ser Asp Gly Asn Ala Tyr Leu His
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: LCDR2 of exemplified PEG-anti-A beta Antibody
      Fragment

<400> SEQUENCE: 59

Lys Val Ser Asn Arg Phe Ser
1               5

<210> SEQ ID NO 60
<211> LENGTH: 9
<212> TYPE: PRT
<213> ORGANISM: Artificial Sequence
<220> FEATURE:
<223> OTHER INFORMATION: LCDR 3 of exemplified PEG-anti-A beta Antibody
      Fragment

<400> SEQUENCE: 60

Thr Gln Ser Thr His Ser Pro Trp Thr
1               5

<210> SEQ ID NO 61
<211> LENGTH: 10
<212> TYPE: PRT
<213> ORGANISM: Artificial Sequence
<220> FEATURE:
<223> OTHER INFORMATION: HCDR 1 of exemplified PEG-anti-A beta Antibody
      Fragment

<400> SEQUENCE: 61

Gly Tyr Thr Phe Ser Arg Tyr Ser Met Ser
1               5                   10

<210> SEQ ID NO 62
<211> LENGTH: 16
<212> TYPE: PRT
<213> ORGANISM: Artificial Sequence
<220> FEATURE:
<223> OTHER INFORMATION: HCVR2 of exemplified PEG-anti-A beta Antibody
      Fragment

<400> SEQUENCE: 62

Gln Ile Asn Ile Arg Gly Cys Asn Thr Tyr Tyr Pro Asp Thr Val Lys
1               5                   10                  15

<210> SEQ ID NO 63
<211> LENGTH: 17
<212> TYPE: PRT
<213> ORGANISM: Artificial Sequence
<220> FEATURE:
<223> OTHER INFORMATION: HCDR2 of exemplified PEG-anti-A beta Antibody
      Fragment

<400> SEQUENCE: 63

Gln Ile Asn Ile Arg Gly Asn Asn Thr Tyr Tyr Pro Asp Thr Val Lys
1               5                   10                  15
```

Gly

<210> SEQ ID NO 64
<211> LENGTH: 3
<212> TYPE: PRT
<213> ORGANISM: Artificial Sequence
<220> FEATURE:
<223> OTHER INFORMATION: HCDR3 of exemplified PEG-anti-A beta Antibody Fragment

<400> SEQUENCE: 64

Gly Asp Phe
1

<210> SEQ ID NO 65
<211> LENGTH: 657
<212> TYPE: DNA
<213> ORGANISM: Artificial Sequence
<220> FEATURE:
<223> OTHER INFORMATION: cDNA encoding LCVR (SEQ ID NO.53) of exemplified PEG-anti-A beta Antibody Fragment

<400> SEQUENCE: 65

```
gacatcgtta tgactcagac tccattgtcc ttgtctgtta ctccaggtca accagcttct      60
atttcctgtt cctcctccca atctttgatc tactccgacg gtaacgctta cttgcactgg    120
tacttgcaaa agcctggtca atccccacaa ttgttgatct acaaggtttc aacagattc    180
tctggtgttc ctgacagatt ttctggttcc ggttccggta ctgacttcac tttgaagatc    240
tccagagttg aagctgagga tgttggtgtt tactactgta ctcagtccac tcattcccca    300
tggacttttg gtggtggtac taaggttgag atcaagagaa ctgttgctgc tccatccgtt    360
ttcattttcc caccatccga cgaacaattg aagtctggta ctgcttccgt tgtttgtttg    420
ttgaacaact tctacccaag agaggctaag gttcagtgga aggttgacaa cgcttttgcaa    480
tccggtaact cccaagaatc cgttactgag caagactcta aggactccac ttactccttg    540
tcctccactt tgactttgtc caaggctgat tacgagaagc acaaggttta cgcttgtgag    600
gttacacatc agggtttgtc ctccccagtt actaagtcct tcaacagagg agagtcc       657
```

<210> SEQ ID NO 66
<211> LENGTH: 657
<212> TYPE: DNA
<213> ORGANISM: Artificial Sequence
<220> FEATURE:
<223> OTHER INFORMATION: cDNA encoding HCVR (SEQ ID NO.54) of exemplified PEG-anti-A beta Antibody Fragment

<400> SEQUENCE: 66

```
gaggttcagt tggttgaatc tggtggtgga ttggttaagc ctggtggttc tttgagattg     60
tcctgtgctg cttccggtta cactttctcc agatactcca tgtcctgggt tagacaagct    120
ccaggaaagg gattggagtg ggttggtcaa atcaacatca gaggttgtaa cacttactac    180
ccagacactg ttaagggaag attcactatc tccagagatg actccaagaa cactttgtac    240
ttgcagatga actccttgaa aactgaggac actgctgttt actactgtac tactggtgac    300
ttttggggac agggaacttt ggttactgtt tcctccgctt ctactaaggg accatccgtt    360
tttccattgg ctccatcctc taagtctact tccggtggta ctgctgcttt gggatgtttg    420
gttaaggact acttcccaga gccagttact gttcttggga actccggtgc tttgacttct    480
ggtgttcaca ctttcccagc tgttttgcaa tcttccggtt tgtactcctt gtcctccgtt    540
gttactgttc catcctcttc cttgggtact cagacttaca tctgtaacgt taaccacaag    600
```
ccatccaaca ctaaggttga caagaaggtt gaaccaaagt cctctgacaa gactcac      657

<210> SEQ ID NO 67
<211> LENGTH: 219
<212> TYPE: PRT
<213> ORGANISM: Artificial Sequence
<220> FEATURE:
<223> OTHER INFORMATION: LC of exemplified anti-Tau antibody

<400> SEQUENCE: 67

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ser
            20                  25                  30

Asn Gln Asn Thr Tyr Leu His Trp Tyr Gln Gln Lys Pro Gly Gln Ala
        35                  40                  45

Pro Arg Leu Leu Ile Tyr Lys Val Asp Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Ser
                85                  90                  95

Thr Leu Val Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 68
<211> LENGTH: 442
<212> TYPE: PRT
<213> ORGANISM: Artificial Sequence
<220> FEATURE:
<223> OTHER INFORMATION: HC of exemplified anti-Tau antibody

<400> SEQUENCE: 68

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Ser Asn Tyr
            20                  25                  30

Trp Ile Glu Trp Val Arg Gln Met Pro Gly Lys Gly Leu Glu Trp Met
        35                  40                  45

Gly Glu Ile Leu Pro Gly Ser Asp Ser Ile Lys Tyr Glu Lys Asn Phe
    50                  55                  60

Lys Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Arg Gly Asn Tyr Val Asp Asp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 69
<211> LENGTH: 16
<212> TYPE: PRT
<213> ORGANISM: Artificial Sequence
<220> FEATURE:
<223> OTHER INFORMATION: LCDR1 of exemplified anti-Tau antibody

<400> SEQUENCE: 69
```

Arg Ser Ser Gln Ser Leu Val His Ser Asn Gln Asn Thr Tyr Leu His
1               5                   10                  15

<210> SEQ ID NO 70
<211> LENGTH: 8
<212> TYPE: PRT
<213> ORGANISM: Artificial Sequence
<220> FEATURE:
<223> OTHER INFORMATION: LCDR2 of exemplified anti-Tau antibody

<400> SEQUENCE: 70

Tyr Lys Val Asp Asn Arg Phe Ser
1               5

<210> SEQ ID NO 71
<211> LENGTH: 9
<212> TYPE: PRT
<213> ORGANISM: Artificial Sequence
<220> FEATURE:
<223> OTHER INFORMATION: LCDR3 of exemplified anti-Tau antibody

<400> SEQUENCE: 71

Ser Gln Ser Thr Leu Val Pro Leu Thr
1               5

<210> SEQ ID NO 72
<211> LENGTH: 13
<212> TYPE: PRT
<213> ORGANISM: Artificial Sequence
<220> FEATURE:
<223> OTHER INFORMATION: HCDR1 of exemplified anti-Tau antibody

<400> SEQUENCE: 72

Lys Gly Ser Gly Tyr Thr Phe Ser Asn Tyr Trp Ile Glu
1               5                   10

<210> SEQ ID NO 73
<211> LENGTH: 17
<212> TYPE: PRT
<213> ORGANISM: Artificial Sequence
<220> FEATURE:
<223> OTHER INFORMATION: HCDR2 of exemplified anti-Tau antibody

<400> SEQUENCE: 73

Glu Ile Leu Pro Gly Ser Asp Ser Ile Lys Tyr Glu Lys Asn Phe Lys
1               5                   10                  15

Gly

<210> SEQ ID NO 74
<211> LENGTH: 9
<212> TYPE: PRT
<213> ORGANISM: Artificial Sequence
<220> FEATURE:
<223> OTHER INFORMATION: HCDR3 of exemplified anti-Tau antibody

<400> SEQUENCE: 74

Ala Arg Arg Gly Asn Tyr Val Asp Asp
1               5

<210> SEQ ID NO 75
<211> LENGTH: 112
<212> TYPE: PRT
<213> ORGANISM: Artificial Sequence
<220> FEATURE:
<223> OTHER INFORMATION: LCVR of exemplified anti-Tau antibody -continued

<400> SEQUENCE: 75

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ser
            20                  25                  30

Asn Gln Asn Thr Tyr Leu His Trp Tyr Gln Gln Lys Pro Gly Gln Ala
        35                  40                  45

Pro Arg Leu Leu Ile Tyr Lys Val Asp Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Ser
                85                  90                  95

Thr Leu Val Pro Leu Thr Phe Gly Gly Gly Thr Lys Val Glu Ile Lys
            100                 105                 110

<210> SEQ ID NO 76
<211> LENGTH: 116
<212> TYPE: PRT
<213> ORGANISM: Artificial Sequence
<220> FEATURE:
<223> OTHER INFORMATION: HCVR of exemplified anti-Tau antibody

<400> SEQUENCE: 76

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Ser Asn Tyr
            20                  25                  30

Trp Ile Glu Trp Val Arg Gln Met Pro Gly Lys Gly Leu Glu Trp Met
        35                  40                  45

Gly Glu Ile Leu Pro Gly Ser Asp Ser Ile Lys Tyr Glu Lys Asn Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Asn Tyr Val Asp Asp Trp Gly Gln Gly Thr Leu Val
            100                 105                 110

Thr Val Ser Ser
        115

<210> SEQ ID NO 77
<211> LENGTH: 1326
<212> TYPE: DNA
<213> ORGANISM: Artificial Sequence
<220> FEATURE:
<223> OTHER INFORMATION: Nucleotide Sequence Encoding the Exemplified HC
     (SEQ ID NO: 16)

<400> SEQUENCE: 77
gaggtgcagc tggtgcagtc tggagcagag gtgaaaaagc ccggggagtc tctgaagatc      60
tcctgtaagg gttctggcta cacattcagt aactactgga tagagtgggt gcgccagatg     120
cccgggaaag gcctggagtg gatggggag attttacctg gaagtgatag tattaagtac      180
gaaaagaatt tcaagggcca ggtcaccatc tcagccgaca gtccatcag caccgcctac      240 ctgcagtgga gcagcctgaa ggcctcggac accgccatgt attactgtgc gagaggggg      300 aactacgtgg acgactgggg ccagggcacc ctggtcaccg tctcctcagc ttctaccaag     360

```
ggcccatcgg tcttcccgct agcgccctgc tccaggagca cctccgagag cacagccgcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cgaagaccta cacctgcaac    600
gtagatcaca gcccagcaac caccaaggtg gacaagagag ttgagtccaa atatggtccc    660
ccatgcccac cctgcccagc acctgaggcc gccgggggac catcagtctt cctgttcccc    720
ccaaaaccca aggacactct catgatctcc cggacccctg aggtcacgtg cgtggtggtg    780
gacgtgagcc aggaagaccc cgaggtccag ttcaactggt acgtggatgg cgtggaggtg    840
cataatgcca agacaaagcc gcgggaggag cagttcaaca gcacgtaccg tgtggtcagc    900
gtcctcaccg tcctgcacca ggactggctg aacggcaagg agtacaagtg caaggtctcc    960
aacaaaggcc tcccgtcctc catcgagaaa accatctcca aagccaaagg gcagccccga   1020
gagccacagg tgtacaccct gcccccatcc caggaggaga tgaccaagaa ccaggtcagc   1080
ctgacctgcc tggtcaaagg cttctacccc agcgacatcg ccgtggagtg ggaaagcaat   1140
gggcagccgg agaacaacta caagaccacg cctcccgtgc tggactccga cggctccttc   1200
ttcctctaca gcaggctaac cgtggacaag agcaggtggc aggaggggaa tgtcttctca   1260
tgctccgtga tgcatgaggc tctgcacaac cactacacac agaagagcct ctccctgtct   1320
ctgggt                                                              1326
```

<210> SEQ ID NO 78
<211> LENGTH: 657
<212> TYPE: DNA
<213> ORGANISM: Artificial Sequence
<220> FEATURE:
<223> OTHER INFORMATION: Nucleotide Sequence Encoding the Exemplified LC
      (SEQ ID NO: 15)

<400> SEQUENCE: 78

```
gaaattgtgt tgacgcagtc tccaggcacc ctgtctttgt ctccagggga aagagccacc     60
ctctcctgca gatctagtca gagccttgta cacagtaatc agaacaccta tttacattgg    120
taccagcaga aacctggcca ggctcccagg ctcctcatct ataaagttga caaccgattt    180
tctggcatcc cagacaggtt cagtggcagt gggtctggga cagacttcac tctcaccatc    240
agcagactgg agcctgaaga ttttgcagtg tattactgtt ctcaaagtac actggttccg    300
ctcacgttcg gcgagggac caaggtggag atcaaacgga ccgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgc       657
```

<210> SEQ ID NO 79
<211> LENGTH: 441
<212> TYPE: PRT
<213> ORGANISM: Artificial Sequence
<220> FEATURE:
<223> OTHER INFORMATION: Amino Acid Sequence of Human, Full-Length Tau

<400> SEQUENCE: 79

Met Ala Glu Pro Arg Gln Glu Phe Glu Val Met Glu Asp His Ala Gly

```
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Glu Ser Pro Leu
                35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Gln Pro His Thr Glu
                85                  90                  95
Ile Pro Glu Gly Thr Thr Ala Glu Glu Ala Gly Ile Gly Asp Thr Pro
                100                 105                 110
Ser Leu Glu Asp Glu Ala Ala Gly His Val Thr Gln Ala Arg Met Val
                115                 120                 125
Ser Lys Ser Lys Asp Gly Thr Gly Ser Asp Asp Lys Lys Ala Lys Gly
                130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Ser Ser Gly Glu Pro Pro Lys Ser Gly
                180                 185                 190
Asp Arg Ser Gly Tyr Ser Ser Pro Gly Ser Pro Gly Thr Pro Gly Ser
                195                 200                 205
Arg Ser Arg Thr Pro Ser Leu Pro Thr Pro Pro Thr Arg Glu Pro Lys
                210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
                260                 265                 270
Gly Lys Val Gln Ile Ile Asn Lys Lys Leu Asp Leu Ser Asn Val Gln
                275                 280                 285
Ser Lys Cys Gly Ser Lys Asp Asn Ile Lys His Val Pro Gly Gly Gly
                290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
                340                 345                 350
Lys Ile Gly Ser Leu Asp Asn Ile Thr His Val Pro Gly Gly Gly Asn
                355                 360                 365
Lys Lys Ile Glu Thr His Lys Leu Thr Phe Arg Glu Asn Ala Lys Ala
                370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
                420                 425                 430
```

Ser Ala Ser Leu Ala Lys Gln Gly Leu
    435                 440

COMBINATION THERAPY

The present application claims priority to U.S. Provisional Patent Application Ser. No. 62/372,453, filed Aug. 9, 2016, entitled Combination Therapy, U.S. Provisional Patent Application Ser. No. 62/373,022, filed Aug. 10, 2016, entitled Combination Therapy, and U.S. Provisional Patent Application Ser. No. 62/375,992, filed Aug. 17, 2016, entitled Combination Therapy, the entire disclosures of which are incorporated herein by reference.

The present invention relates to a combination of an anti-Tau antibody with one of an anti-N3pGlu Abeta antibody, an antibody that sequesters amyloid beta peptide (anti-Aβ antibody), and an antibody fragment that binds amyloid beta peptide and is covalently attached to a polyethylene glycol (PEG) molecule, as well as methods of using the same, for the treatment of neurodegenerative diseases characterized by the formation of amyloid plaques and/or deposition of amyloid β (Abeta or Aβ) peptide and aberrant tau aggregation, such as Alzheimer's disease (AD).

AD is a devastating neurodegenerative disorder that affects millions of patients worldwide. In view of the currently approved agents on the market which afford only transient, symptomatic benefits to the patient, there is a significant unmet need in the treatment of AD. AD is characterized by the generation, aggregation, and deposition of Abeta and by aberrant tau aggregation in the brain.

Antibodies that specifically target N3pGlu Abeta have been shown to lower Aβ plaque levels in vivo (U.S. Patent Application Publication No. 2013/0142806). These antibodies are referred to herein as "anti-N3pGlu Abeta antibodies." N3pGlu Abeta, also referred to as N3pGlu Aβ, N3pG, N3pE, or A beta$_{p3-42}$, is a truncated form of the Abeta peptide found only in plaques. Although N3pGlu Abeta peptide is a minor component of the deposited Abeta in the brain, studies have demonstrated that N3pGlu Abeta peptide has aggressive aggregation properties and accumulates early in the deposition cascade.

Antibodies that specifically target, and sequester Aβ peptide have been shown to lower free Aβ and plaque levels in vivo (U.S. Pat. Nos. 7,195,761 and 8,591,894). These antibodies are referred to herein as "anti-Aβ antibodies."

Molecules comprising an antibody fragment that specifically binds Aβ peptide between residues 13-28 of human Aβ peptide and do not specifically bind amyloid precursor protein ("APP"), and which are covalently attached to one or more polyethylene glycol (PEG) molecules, have been shown to lower free Aβ in vivo (see, for example, U.S. Pat. No. 8,066,999). These molecules are referred to herein as "PEG-anti-Aβ antibody fragments."

Moreover, animal model studies have shown tau aggregates spread across neuronal synapse junctions and sequester monomeric (native or non-aggregated) tau, inducing tau aggregate formation. Neuroanatomical progression of tau aggregation and accumulation in neurodegenerative diseases, such as AD, suggests that tau fibril aggregation propagates along neuronal networks, ultimately resulting in destabilization of microtubules and ultimately localized impaired neuronal function. This suggests that even small reductions in tau aggregation and accumulation might result in a long-term significant reduction in intraneuronal neurofibrillary tangles (NFTs), thus providing therapeutic benefits, particularly in the treatment of AD.

A combination of an antibody which specifically binds tau aggregates and which reduces the propagation of tau aggregate formation (referred to herein as "anti-Tau antibodies") with an antibody that binds N3pGlu Abeta is desired to provide treatment for neurodegenerative disorders, such as AD. Such combination will also preferably be more effective than either antibody alone. For example, treatment with such combination may allow for use of lower doses of either or both antibodies as compared to each antibody used alone, potentially leading to lower side effects (or a shorter duration of one or the other therapy) while maintaining efficacy. It is believed that targeting tau aggregates with a tau antibody will reduce the propagation of tau aggregate formation, NFT formation, and neuronal loss, and that targeting the removal of deposited forms of Abeta with an N3pGlu antibody will facilitate the phagocytic removal of pre-existing plaque deposits while at the same time reduce or prevent further deposition of Abeta by inhibiting the generation of Abeta plaques.

Also, a combination of an anti-Tau antibodies with an antibody that binds Abeta peptide is desired to provide treatment for neurodegenerative disorders, such as AD. Such combination will also preferably be more effective than either antibody alone. For example, treatment with such combination may allow for use of lower doses of either or both antibodies as compared to each antibody used alone, potentially leading to lower side effects (or a shorter duration of one or the other therapy) while maintaining efficacy. It is believed that targeting tau aggregates with a tau antibody will reduce the propagation of tau aggregate formation, NFT formation, and neuronal loss, and that targeting the sequestration of Aβ peptide with an anti-Aβ antibody will facilitate the clearance of Aβ peptide and prevent plaque formation.

Additionally, a combination of an anti-Tau antibodies with a molecule that binds Aβ peptide (and specifically between residues 13-28 of human Aβ peptide and does not specifically bind APP) is desired to provide treatment for neurodegenerative disorders, such as AD. Such combination will also preferably be more effective than either antibody alone. For example, treatment with such combination may allow for use of lower doses of either or both molecule as compared to each molecule used alone, potentially leading to lower side effects (or a shorter duration of one or the other therapy) while maintaining efficacy. It is believed that targeting tau aggregates with an anti-tau antibody will reduce the propagation of tau aggregate formation, NFT formation, and neuronal loss, and that targeting the Aβ peptide (between residues 13-28) with a PEG-anti-Aβ antibody fragment will be useful as a treatment of neurodegenerative diseases characterized by formation of amyloid plaques and aberrant tau aggregation.

Accordingly, the present invention provides a method of treating a cognitive or neurodegenerative disease, comprising administering to a patient in need of such treatment an effective amount of an anti-Tau antibody in combination with an effective amount of an anti-N3pGlu Abeta antibody; an antibody that binds Abeta peptide; and/or a PEG-anti-Aβ antibody fragment. The present invention further provides a method of treating clinical or pre-clinical AD comprising administering to a patient in need of such treatment an effective amount of an anti-Tau antibody in combination with an effective amount of an anti-N3pGlu Abeta antibody; an antibody that binds Abeta peptide; and/or a PEG-anti-Aβ antibody fragment. The present invention also provides a method of treating prodromal AD (sometimes also referred to as mild cognitive impairment, or MCI), mild AD, moderate AD and/or severe AD, comprising administering to a patient in need of such treatment an effective amount of an anti-Tau antibody in combination with an effective amount of an anti-N3pGlu Abeta antibody; an antibody that binds Abeta peptide; and/or a PEG-anti-Aβ antibody fragment.

The present invention further provides a method of slowing cognitive decline in a patient diagnosed with pre-clinical AD or clinical AD, comprising administering to a patient in need of such treatment an effective amount of an anti-Tau antibody in combination with an effective amount of an anti-N3pGlu Abeta antibody; an antibody that binds Abeta peptide; and/or a PEG-anti-Aβ antibody fragment. The present invention further provides a method of slowing functional decline in a patient diagnosed with pre-clinical AD or clinical AD, comprising administering to a patient in need of such treatment an effective amount of an anti-Tau antibody in combination with an effective amount of an anti-N3pGlu Abeta antibody; an antibody that binds Abeta peptide; and/or a PEG-anti-Aβ antibody fragment. The present invention further provides a method of preventing memory loss or cognitive decline in asymptomatic patients with low levels of Aβ1-42 in the cerebrospinal fluid (CSF) or Aβ plaques in the brain, comprising administering an effective amount of an anti-Tau antibody in combination with an effective amount of an anti-N3pGlu Abeta antibody; an antibody that binds Abeta peptide; and/or a PEG-anti-Aβ antibody fragment.

In another embodiment the present invention provides a method of treating asymptomatic patients known to have an Alzheimer's disease-causing genetic mutation, comprising administering an effective amount of an anti-Tau antibody in combination with an effective amount of an anti-N3pGlu Abeta antibody; an antibody that binds Abeta peptide; and/or a PEG-anti-Aβ antibody fragment. Another embodiment the present invention provides a method for the prevention of the progression of mild cognitive impairment to AD, comprising administering to a patient in need of such treatment an effective amount of an anti-Tau antibody in combination with an effective amount of an anti-N3pGlu Abeta antibody; an antibody that binds Abeta peptide; and/or a PEG-anti-Aβ antibody fragment.

The present embodiments also provide an anti-N3pGlu Abeta antibody, for use in simultaneous, separate, or sequential combination with an anti-Tau antibody, for use in therapy. The present embodiments also provide an anti-Aβ antibody, for use in simultaneous, separate, or sequential combination with an anti-Tau antibody, for use in therapy. The present embodiments also provide a PEG-anti-Aβ antibody fragment, for use in simultaneous, separate, or sequential combination with an anti-Tau antibody, for use in therapy.

The invention further provides a pharmaceutical composition comprising one of an anti-N3pGlu Abeta antibody, an antibody that binds Abeta peptide, and a PEG-anti-Aβ antibody fragment, with one or more pharmaceutically acceptable carriers, diluents, or excipients, in combination with a pharmaceutical composition of an anti-Tau antibody, with one or more pharmaceutically acceptable carriers, diluents, or excipients.

In addition, the invention provides a kit, comprising an anti-Tau antibody with one of an anti-N3pGlu Abeta antibody, an antibody that binds Abeta peptide, and a PEG-anti-Aβ antibody fragment. The invention further provides a kit, comprising a pharmaceutical composition comprising an anti-Tau antibody with one or more pharmaceutically acceptable carriers, diluents, or excipients, and one of an anti-N3pGlu Abeta antibody, an antibody that binds Abeta peptide, and a PEG-anti-Aβ antibody fragment. As used herein, a "kit" includes separate containers of each component, wherein one component is an anti-Tau antibody, in a single package, and another component is one of an anti-N3pGlu Abeta antibody, an antibody that binds Abeta peptide, and a PEG-anti-Aβ antibody fragment, in a single package. A "kit" may also include separate containers of each component, wherein one component is an anti-Tau antibody and another component is one of an anti-N3pGlu Abeta antibody, an antibody that binds Abeta peptide, and a PEG-anti-Aβ antibody fragment, in separate packages with instructions to administer each component as a combination.

The invention further provides the use of one of an anti-N3pGlu Abeta antibody, an antibody that binds Abeta peptide, and a PEG-anti-Aβ antibody fragment, for the manufacture of a medicament for the treatment of AD, mild AD, prodromal AD or for the prevention of the progression of mild cognitive impairment to AD wherein the medicament is to be administered simultaneously, separately or sequentially with an anti-Tau antibody.

Anti-Tau Antibody

In an embodiment of the present invention, the anti-Tau antibody comprises a heavy chain (HC) and a light chain (LC), wherein the HC comprises a heavy chain variable region (HCVR) and the LC comprises a light chain variable region (LCVR), said HCVR comprising complementarity determining regions (CDRs) HCDR1, HCDR2 and HCDR3 and said LCVR comprising CDRs LCDR1, LCDR2 and LCDR3. According to particular embodiments of the anti-Tau antibodies of the present invention, the amino acid sequence of LCDR1 is given by SEQ ID NO.69, the amino acid sequence of LCDR2 is given by SEQ ID NO.70, the amino acid sequence of LCDR3 is given by SEQ ID NO.71, the amino acid sequence of HCDR1 is given by SEQ ID NO.72, the amino acid sequence of HCDR2 is given by SEQ ID NO.73, and the amino acid sequence of HCDR3 is given by SEQ ID NO.74. In an embodiment, the present invention provides a monoclonal antibody that binds human tau, comprising a LCVR and a HCVR, wherein the amino acid sequence of the LCVR is given by SEQ ID NO.75 and the amino acid sequence of the HCVR is given by SEQ ID NO. 76. In a further embodiment, the present invention provides a monoclonal antibody that binds human tau, comprising a light chain (LC) and a heavy chain (HC), wherein the amino acid sequence of the LC is given by SEQ ID NO.67 and the amino acid sequence of the HC is given by SEQ ID NO.68.

The anti-Tau antibodies of the present invention may be prepared and purified using known methods. For example, cDNA sequences encoding a HC (for example the amino acid sequence given by SEQ ID NO.68), such as the cDNA sequence given by SEQ ID NO.77, and a LC (for example, the amino acid sequence given by SEQ ID NO.67), such as the cDNA sequence given by SEQ ID NO.78, may be cloned and engineered into a GS (glutamine synthetase) expression vector. The engineered immunoglobulin expression vector may then be stably transfected into CHO cells. As one of skill in the art will appreciate, mammalian expression of antibodies will result in glycosylation, typically at highly conserved N-glycosylation sites in the Fc region. Stable clones may be verified for expression of an antibody specifically binding to tau aggregates. Positive clones may be expanded into serum-free culture medium for antibody production in bioreactors. Media, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques.

Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

The anti-Tau antibodies of the present invention bind human tau. In an embodiment, the anti-Tau antibodies of the present invention bind a conformational epitope of human tau. In a particular embodiment, the conformational epitope of human tau includes amino acid residues 7-9 and 312-322 of human tau, wherein the amino acid sequence of the human tau is given by SEQ ID NO.79.

Anti-N3pGlu Abeta Antibody

In an embodiment of the present invention, the anti-N3pGlu Abeta antibody comprises a light chain variable region (LCVR) and a heavy chain variable region (HCVR), wherein said LCVR comprises LCDR1, LCDR2 and LCDR3 and HCVR comprises HCDR1, HCDR2 and HCDR3 which are selected from the group consisting of:
  a) LCDR1 is SEQ ID NO.17, LCDR2 is SEQ ID NO.18, LCDR3 is SEQ ID NO.19, HCDR1 is SEQ ID NO.20, HCDR2 is SEQ ID NO.22, and HCDR3 is SEQ ID NO.23;
  b) LCDR1 is SEQ ID NO.17, LCDR2 is SEQ ID NO.18, LCDR3 is SEQ ID NO.19, HCDR1 is SEQ ID NO.21, HCDR2 is SEQ ID NO.22, and HCDR3 is SEQ ID NO.24;
  c) LCDR1 is SEQ ID NO.17, LCDR2 is SEQ ID NO.18, LCDR3 is SEQ ID NO.19, HCDR1 is SEQ ID NO.36, HCDR2 is SEQ ID NO.22, and HCDR3 is SEQ ID NO.37;
  d) LCDR1 is SEQ ID NO.4, LCDR2 is SEQ ID NO.6, LCDR3 is SEQ ID NO.7, HCDR1 is SEQ ID NO.1, HCDR2 is SEQ ID NO.2, and HCDR3 is SEQ ID NO.3; and
  e) LCDR1 is SEQ ID NO.4, LCDR2 is SEQ ID NO.5, LCDR3 is SEQ ID NO.7, HCDR1 is SEQ ID NO.1, HCDR2 is SEQ ID NO.2, and HCDR3 is SEQ ID NO.3.

In other embodiments, the anti-N3pGlu Abeta antibody comprises a light chain variable region (LCVR) and a heavy chain variable region (HCVR), wherein said LCVR and HCVR are selected from the group consisting of:
  a) LCVR of SEQ ID NO.25 and HCVR of SEQ ID NO.26;
  b) LCVR of SEQ ID NO.25 and HCVR of SEQ ID NO.27;
  c) LCVR of SEQ ID NO.32 and HCVR of SEQ ID NO.34;
  d) LCVR of SEQ ID NO.9 and HCVR of SEQ ID NO.8; and
  e) LCVR of SEQ ID NO.10 and HCVR of SEQ ID NO.8.

In further embodiments, the anti-N3pGlu Abeta antibody comprises a light chain (LC) and a heavy chain (HC), wherein said LC and HC are selected from the group consisting of:
  a) LC of SEQ ID NO.28 and HC of SEQ ID NO.29;
  b) LC of SEQ ID NO.28 and HC of SEQ ID NO.30;
  c) LC of SEQ ID NO.33 and HC of SEQ ID NO.35;
  d) LC of SEQ ID NO.12 and HC of SEQ ID NO.11; and
  e) LC of SEQ ID NO.13 and HC of SEQ ID NO.11.

In other embodiments, the anti-N3pGlu Abeta antibody comprises two light chains (LC) and two heavy chains (HC), wherein each LC and each HC are selected from the group consisting of:
  a) LC of SEQ ID NO.28 and HC of SEQ ID NO.29;
  b) LC of SEQ ID NO.28 and HC of SEQ ID NO.30;
  c) LC of SEQ ID NO.33 and HC of SEQ ID NO.35;
  d) LC of SEQ ID NO.12 and HC of SEQ ID NO.11; and
  e) LC of SEQ ID NO.13 and HC of SEQ ID NO.11.

In some embodiments, the anti-N3pGlu Abeta antibody comprises Antibody I, which has a light chain (LC) and a heavy chain (HC) of SEQ ID NOs.12 and 11 respectively. Antibody I further has a light chain variable region (LCVR) and a heavy chain variable region (HCVR) of SEQ ID NOs.9 and 8 respectively. The HCVR of Antibody I further comprises HCDR1 of SEQ ID NO. 1, HCDR2 of SEQ ID NO.2, and HCDR3 of SEQ ID NO.3. The LCVR of Antibody I further comprises LCDR1 of SEQ ID NO.4, LCDR2 of SEQ ID NO.6 and LCDR3 of SEQ ID NO.7 respectively.

In some embodiments, the anti-N3pGlu Abeta antibody comprises Antibody II, which has a light chain (LC) and a heavy chain (HC) of SEQ ID NOs.13 and 11 respectively. Antibody II further has a light chain variable region (LCVR) and a heavy chain variable region (HCVR) of SEQ ID NOs.10 and 8 respectively. The HCVR of Antibody II further comprises HCDR1 of SEQ ID NO.1, HCDR2 of SEQ ID NO.2, and HCDR3 of SEQ ID NO.3. The LCVR of Antibody II further comprises LCDR1 of SEQ ID NO.4, LCDR2 of SEQ ID NO.5, and LCDR3 of SEQ ID NO.7 respectively.

In some embodiments, the anti-N3pGlu Abeta antibody comprises B12L, which has a light chain (LC) and a heavy chain (HC) of SEQ ID NOs. 28 and 29 respectively. B12L further has a light chain variable region (LCVR) and a heavy chain variable region (HCVR) of SEQ ID NOs. 25 and 26 respectively. The HCVR of B12L further comprises HCDR1 of SEQ ID NO.20, HCDR2 of SEQ ID NO.22 and HCDR3 of SEQ ID NO.23. The LCVR of B12L further comprises LCDR1 of SEQ ID NO.17, LCDR2 of SEQ ID NO.18 and LCDR3 of SEQ ID NO.19 respectively.

In some embodiments, the anti-N3pGlu Abeta antibody comprises R17L which has a light chain (LC) and a heavy chain (HC) of SEQ ID NOs.28 and 30 respectively. R17L further has a light chain variable region (LCVR) and a heavy chain variable region (HCVR) of SEQ ID NOs.25 and 27 respectively. The HCVR of R17L further comprises HCDR1 of SEQ ID NO.21, HCDR2 of SEQ ID NO.22 and HCDR3 of SEQ ID NO.24. The LCVR of R17L further comprises LCDR1 of SEQ ID NO.17, LCDR2 of SEQ ID NO.18 and LCDR3 of SEQ ID NO.19 respectively.

In some embodiments, the anti-N3pGlu Abeta antibody comprises hE8L which has a light chain (LC) and a heavy chain (HC) of SEQ ID NOs.33 and 35 respectively. hE8L further has a light chain variable region (LCVR) and a heavy chain variable region (HCVR) of in SEQ ID NOs.32 and 34 respectively. The HCVR of hE8L further comprises HCDR1 of SEQ ID NO.36, HCDR2 of SEQ ID NO.22 and HCDR3 of SEQ ID NO.37. The LCVR of hE8L further comprises LCDR1 of SEQ ID NO.17, LCDR2 of SEQ ID NO.18 and LCDR3 of SEQ ID NO.19 respectively.

One of ordinary skill in the art will appreciate and recognize that "anti-N3pGlu Abeta antibody", and the specific antibodies, "B12L" and "R17L" are identified and disclosed along with methods for making and using said antibodies by one of ordinary skill in the art, in U.S. Pat. No. 8,679,498 B2, entitled "Anti-N3pGlu Amyloid Beta Peptide Antibodies and Uses Thereof", issued Mar. 25, 2014 (U.S. Ser. No. 13/810,895). See for example Table 1 of U.S. Pat. No. 8,679,498 B2. Each of these two antibodies (e.g., "B12L" and "R17L") may be used as the anti-N3pGlu Abeta antibody of the present invention. In other embodiments, the anti-N3pGlu Abeta antibody may comprise the antibody "hE8L" described herein. In further embodiments, the anti- N3pGlu Abeta antibody may comprise "Antibody I" outlined herein. In yet further embodiments, the anti-N3pGlu Abeta antibody may comprise "Antibody II" outlined herein.

The anti-N3pGlu Abeta antibodies of the present invention bind to N3pGlu Aβ. The sequence of N3pGlu Aβ is the amino acid sequence of SEQ ID NO.31. The sequence of Aβ is SEQ ID NO.38.

Anti-Aβ Antibody

In an embodiment of the present invention, the anti-Aβ antibody comprises a heavy chain (HC) and a light chain (LC), wherein the HC comprises a heavy chain variable region (HCVR) and the LC comprises a light chain variable region (LCVR), said HCVR comprising complementarity determining regions (CDRs) HCDR1, HCDR2 and HCDR3 and said LCVR comprising CDRs LCDR1, LCDR2 and LCDR3. According to particular embodiments of the anti-Aβ antibody of the present invention, the amino acid sequence of LCDR1 is given by SEQ ID NO.39, the amino acid sequence of LCDR2 is given by SEQ ID NO.40, the amino acid sequence of LCDR3 is given by SEQ ID NO.41, the amino acid sequence of HCDR1 is given by SEQ ID NO.42, the amino acid sequence of HCDR2 is given by SEQ ID NO.43, and the amino acid sequence of HCDR3 is given by SEQ ID NO.44. In an embodiment, the present invention provides a monoclonal antibody that binds human tau, comprising a LCVR and a HCVR, wherein the amino acid sequence of the LCVR is given by SEQ ID NO.45 and the amino acid sequence of the HCVR is given by SEQ ID NO.46. In a more specific embodiment, the amino acid sequence of the LCVR is given by SEQ ID NO.47 and the amino acid sequence of the HCVR is given by SEQ ID NO.48. In a further embodiment, the present invention provides a monoclonal antibody that binds human tau, comprising a light chain (LC) and a heavy chain (HC), wherein the amino acid sequence of the LC is given by SEQ ID NO.49 and the amino acid sequence of the HC is given by SEQ ID NO.50.

One of ordinary skill in the art will appreciate and recognize that anti-Aβ antibodies of the present invention are identified and disclosed along with methods for making and using said antibodies by one of ordinary skill in the art, in U.S. Pat. No. 7,195,761, entitled "Humanized Antibodies that Sequester ABeta Peptide," issued Mar. 27, 2007, and U.S. Pat. No. 8,591,894, entitled "Humanized Antibodies that Sequester ABeta Peptide", issued Nov. 26, 2013, both of which are incorporated herein by reference.

PEG-Anti-Aβ Antibody Fragment

In an embodiment of the present invention, a PEG-anti-Aβ antibody fragment that specifically binds human Aβ peptide between residues 13-28 of human Aβ peptide (SEQ ID NO. 56) and does not specifically bind APP is provided. According to such embodiments, the PEG-anti-Aβ antibody fragment comprises a heavy chain variable region (HCVR) and a light chain variable region (LCVR), wherein the LCVR comprises complementarity determining regions (CDRs) LCDR1, LCDR2 and LCDR3 and the HCVR comprises CDRs HCDR1, HCDR2 and HCDR3. According to particular embodiments of the PEG-anti-Aβ antibody fragment of the present invention, the PEG-anti-Aβ antibody fragment is a Fab and the amino acid sequence of LCDR1 is given by SEQ ID NO.58, the amino acid sequence of LCDR2 is given by SEQ ID NO.59, the amino acid sequence of LCDR3 is given by SEQ ID NO.60, the amino acid sequence of HCDR1 is given by SEQ ID NO.61, the amino acid sequence of HCDR2 is given by SEQ ID NO.62 or SEQ ID NO.63, and the amino acid sequence of HCDR3 is given by SEQ ID NO.64. According to such embodiments, a PEG molecule is covalently attached to one of the HCVR or LCVR. According to particular embodiments, the PEG molecule is covalently attached to a CDR. In an even more particular embodiment, the PEG molecule that is covalently attached to a cysteine residue within the CDR, for example the cysteine residue within a HCDR2 given by SEQ ID NO.62 of the HCVR of the PEG-anti-Aβ antibody fragment. In particular embodiments, the PEG molecule is attached to the cysteine via maleimide linkage. In even more particular embodiments, the PEG molecule has a molecular weight of between about 0.5 kD to about 30 kD. In even more particular embodiments, the PEG molecule has a molecular weight of about 20 kD.

In an embodiment, the present invention provides a PEG-anti-Aβ antibody fragment that specifically binds human Aβ peptide between residues 13-28 of human Aβ peptide and does not specifically bind APP. In particular embodiments, the PEG-anti-Aβ antibody fragment is a Fab comprising a LCVR and a HCVR, wherein the amino acid sequence of the LCVR is given by SEQ ID NO.53 and the amino acid sequence of the HCVR is given by SEQ ID NO.54. According to particular embodiments, a PEG molecule is covalently attached to a cysteine residue at amino acid position 56 of said HCVR (SEQ ID NO.54). In particular embodiments, the PEG molecule is attached to the cysteine via maleimide linkage. In even more particular embodiments, the PEG molecule has a molecular weight of between about 0.5 kD to about 30 kD. In even more particular embodiments, the PEG molecule has a molecular weight of about 2.0 W.

In an embodiment, the present invention provides a PEG-anti-Aβ antibody fragment that specifically binds human Aβ peptide between residues 13-28 of human Aβ peptide and does not specifically bind APP. Particular embodiments comprise a Fab comprising a LCVR and a HCVR, wherein the amino acid sequence of the LCVR is given by SEQ ID NO.53 and the amino acid sequence of the HCVR is given by SEQ ID NO.55. According to particular embodiments, a PEG molecule is covalently attached to the hinge region of the antibody fragment. In particular embodiments, the PEG molecule is covalently attached to the hinge region via a maleimide linkage. In even more particular embodiments, the PEG molecule has a molecular weight of between about 0.5 kD to about 30 W. In even more particular embodiments, the PEG molecule has a molecular weight of about 20 kD.

In a further particular embodiment, the present invention provides a PEG-anti-Aβ antibody fragment that specifically binds human Aβ peptide between residues 13-28 of human Aβ peptide and does not specifically bind APP. According to said particular embodiments, the PEG-anti-Aβ antibody fragment comprises a Fab comprising a LCVR having an amino acid sequence given by SEQ ID NO.53 and a HCVR having an amino acid sequence given by SEQ ID NO.54, wherein a PEG molecule is covalently attached to a cysteine residue at amino acid position 56 of said HCVR, the PEG molecule having a molecular weight of about 20 kD. In further particular embodiments, the PEG molecule is covalently attached to the hinge region via a maleimide linkage.

In a further particular embodiment, the present invention provides a PEG-anti-Aβ antibody fragment that specifically binds human Aβ peptide between residues 13-28 of human Aβ peptide and does not specifically bind APP. Said particular embodiments comprise a Fab having a LCVR having an amino acid sequence given by SEQ ID NO.53 and a HCVR having an amino acid sequence given by SEQ ID NO.55, wherein a PEG molecule is covalently attached to the hinge region of the PEG-anti-Aβ antibody fragment via a maleimide linkage, the PEG molecule having a molecular weight of about 20 kD.

One of ordinary skill in the art will appreciate and recognize that PEG-anti-Aβ antibody fragments of the present invention are identified and disclosed along with methods for making and using said PEG-anti-Aβ antibody fragments by one of ordinary skill in the art, in U.S. Pat. No. 8,066,999, entitled "Pegylated Aβ FAB," issued Nov. 29, 2011, which is incorporated herein by reference.

Definitions

As used herein, an "antibody" is an immunoglobulin molecule comprising two Heavy Chain (HC) and two Light Chain (LC) interconnected by disulfide bonds. The amino terminal portion of each LC and HC includes a variable region responsible for antigen recognition via the complementarity determining regions (CDRs) contained therein. The CDRs are interspersed with regions that are more conserved, termed framework regions. Assignment of amino acids to CDR domains within the LCVR and HCVR regions of the antibodies of the present invention is based on the well-known numbering conventions such as the following: Kabat, et al., Ann. NY Acad. Sci. 190:382-93 (1971); Kabat et al., Sequences of Proteins of Immunological Interest, Fifth Edition, U.S. Department of Health and Human Services, NIH Publication No. 91-3242 (1991); and North numbering convention (North et al., A New Clustering of Antibody CDR Loop Conformations, Journal of Molecular Biology, 406:228-256 (2011)).

As used herein, the term "antibody fragment" refers to one or more fragments of an antibody that retain the ability to specifically bind to an antigen (e.g., human Aβ peptide). Examples of molecules encompassed within the term "antibody fragment" include: (i) a Fab fragment, a monovalent fragment consisting of the VL, VH, CL and CH 1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and (v) a dAb fragment (Ward, et al., (1989) *Nature* 341:544-546), which consists of a VH domain. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al. (1988) *Science* 242:423-426: and Huston et al. (1988) *Proc. Natl. Acad. Sci. USA* 85:5879-5883). Such single chain antibodies are also intended to be encompassed within the term "antibody fragment". Other forms of single chain antibodies, such as diabodies are also encompassed by the term "antibody fragment". Diabodies are bivalent, bispecific binding proteins in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Pollak, R. J., et al. (1994) *Structure* 2:1121-1123).

The PEG-anti-Aβ antibody fragments of the present invention are covalently attached to one or more PEG molecules. It is intended that the term "polyethylene glycol" and "PEG" be used interchangeably and refer to polyethylene glycol or a derivative thereof as known in the art (see, e.g., U.S. Pat. Nos. 5,445,090; 5,900,461; 5,932,462; 6,436,386; 6,448,369; 6,437,025; 6,448,369; 6,495,659; 6,515,100 and 6,514,491). Preferably, PEG is covalently attached to one or more lysine or cysteine residues of the PEG-anti-Aβ antibody fragment. More preferably, PEG is covalently attached to a one or more lysine or cysteine residues in the HCVR of the PEG-anti-Aβ antibody fragment. Even more preferably, PEG is covalently attached to a one or more lysine or cysteine residues within the CDR of the PEG-anti-Aβ antibody fragments. Most preferably, PEG is attached to a cysteine residue at amino acid position 56 of the HCVR of the said SEQ ID NO: 54. Alternatively, the PEG molecules may be attached to the antibody fragment via a linker or spacer molecule to the hinge region of a PEG-anti-Aβ antibody fragment. Addition of linkers and spacer molecules to the hinge regions are well known in the art. Furthermore, a PEG molecule may be covalently attached to modified non-natural amino acids of a PEG-anti-Aβ antibody fragment by techniques well known in the art.

In its typical form, "PEG" is a linear polymer with terminal hydroxyl groups and has the formula HO—CH$_2$CH$_2$—(CH$_2$CH$_2$O)n-CH$_2$CH$_2$—OH, where n is from about 8 to about 4000. The terminal hydrogen may be substituted with a protective group such as an alkyl or alkanol group (M-PEG). Preferably, PEG has at least one hydroxy group, more preferably it is a terminal hydroxy group. It is this hydroxy group which is preferably activated to react with the peptide. A variety of chemical modifications are used to prepare an active PEG derivative with a functional group, such as active carbonate, active ester, aldehyde, tresylate, or using PEG-propionaidehyde suitable for coupling to a given target molecule. The activated PEG derivative is then covalently linked to a reactive group on the polypeptide drug. There are many forms of PEG useful for the present invention. Numerous derivatives of PEG exist in the art and are suitable for use in the invention. The PEG molecule covalently attached to a PEG-anti-Aβ antibody fragment of the present invention is not intended to be limited to a particular type or size. The molecular weight of the PEG molecule is preferably from about 0.5 kilodaltons (kD) to about 100 kD and more preferably from about 5 kD to about 30 kD and most preferably, from about 1 kD to about 20 kD. PEG molecule may be linear or branched and the PEG-anti-Aβ antibody fragment of the invention may have 1, 2, 3, 4, 5 or 6 PEG molecules attached to the peptide. It is most preferable that there be one PEG molecule attached per PEG-anti-Aβ antibody fragment; however, when more than one PEG molecule per PEG-anti-Aβ antibody fragment is present, it is preferred that there are no more than six. It is further contemplated that both ends of the PEG molecule may adapted for cross-linking two or more PEG-anti-Aβ antibody fragments together. Methods of attaching PEG molecules to proteins, antibodies and fragments thereof, are well known in the art.

In particular embodiments of the present invention, the antibodies and antibody fragments, or the nucleic acids encoding same, may be provided in isolated form. As used herein, the term "isolated" refers to a protein, peptide, or nucleic acid that is not found in nature and which is free or substantially free from other macromolecular species found in a cellular environment. "Substantially free", as used herein, means the protein, peptide or nucleic acid of interest comprises more than 80% (on a molar basis) of the macromolecular species present, preferably more than 90% and more preferably more than 95%. In particular embodiments of the present invention, the antibodies and/or antibody fragments, or the nucleic acids encoding same, may be provided in isolated form. As used herein, the term "isolated" refers to a protein, peptide, or nucleic acid that is not found in nature and which is free or substantially free from other macromolecular species found in a cellular environment. "Substantially free", as used herein, means the protein, peptide or nucleic acid of interest comprises more than 80% (on a molar basis) of the macromolecular species present, preferably more than 90% and more preferably more than 95%.

Following expression and secretion of the antibodies and/or antibody fragments of the present invention, the medium is clarified to remove cells and the clarified media is purified using any of many commonly-used techniques. Purified antibodies or fragments may be formulated into pharmaceutical compositions according to well-known methods for formulating proteins and antibodies for parenteral administration, particularly for subcutaneous, intrathecal, or intravenous administration. The antibodies or fragments may be lyophilized, together with appropriate pharmaceutically-acceptable excipients, and then later reconstituted with a water-based diluent prior to use. Alternatively, the antibodies may be formulated in an aqueous solution and stored prior to use. In either case, the stored form and the injected form of the pharmaceutical compositions of the antibodies will contain a pharmaceutically-acceptable excipient or excipients, which are ingredients other than the antibodies. Whether an ingredient is pharmaceutically-acceptable depends on its effect on the safety and effectiveness or on the safety, purity, and potency of the pharmaceutical composition. If an ingredient is judged to have a sufficiently unfavorable effect on safety or effectiveness (or on safety, purity, or potency) to warrant it not being used in a composition for administration to humans, then it is not pharmaceutically-acceptable to be used in a pharmaceutical composition of the antibody or fragments.

As referred to herein, the term "disease characterized by deposition of Aβ," is a disease that is pathologically characterized by Aβ deposits in the brain or in brain vasculature. This includes diseases such as AD, Down's syndrome, and cerebral amyloid angiopathy. The term "disease characterized by aberrant tau aggregation," refers to a disease characterized by propagation of at least one of tau aggregate formation, NFT formation, and neuronal loss. This includes diseases such as AD, Progressive Supranuclear Palsy (PSP), corticobasal degeneration, and Pick's Disease.

A clinical diagnosis, staging or progression of AD can be readily determined by the attending diagnostician or health care professional, as one skilled in the art, by using known techniques and by observing results. This generally includes some form of brain imaging (e.g., MRI, Amyloid PET), mental or cognitive assessment (e.g. Clinical Dementia Rating-summary of boxes (CDR-SB), Mini-Mental State Exam 25 (MMSE) or Alzheimer's Disease Assessment Scale-Cognitive (ADAS-Cog)) or functional assessment (e.g. Alzheimer's Disease Cooperative Study-Activities of Daily Living (ADCS-ADL). "Clinical Alzheimer's disease" as used herein is a diagnosed stage of AD. It includes conditions diagnosed as prodromal Alzheimer's disease, mild AD, moderate AD and severe AD. The term "preclinical Alzheimer's disease" is a stage that precedes clinical AD, where measurable changes in biomarkers (such as CSF Aβ42 levels or deposited brain plaque by amyloid PET) indicate the earliest signs of a patient with Alzheimer's pathology, progressing to clinical AD. This is usually before symptoms such as memory loss and confusion are noticeable.

As used herein, the terms "treating", "to treat", or "treatment", includes restraining, slowing, stopping, reducing, or reversing the progression or severity of an existing symptom, disorder, condition, or disease, such as AD.

As used herein, the term "patient" refers to a human.

As used herein, the term "inhibition of production of Abeta peptide" is taken to mean decreasing of in vivo levels of A-beta peptide in a patient.

The term "prevention" means prophylactic administration of the combination of the antibodies and/or antibody fragments outlined herein to an asymptomatic patient or a patient with pre-clinical AD to prevent progression of the disease.

As used herein, the term "effective amount" refers to the amount or dose of an anti-N3pGlu Abeta antibody, an anti-Aβ antibody or a PEG-anti-Aβ antibody fragment, and to the amount or dose of an anti-Tau antibody administered to the patient, that provides the desired effect in the patient under diagnosis or treatment. It is understood that the combination therapy of the present invention is carried out by the anti-N3pGlu Abeta antibody, anti-Aβ antibody or PEG-anti-Aβ antibody fragment, together with the anti-Tau antibody in any manner which provides effective levels of the anti-N3pGlu Abeta antibody, anti-Aβ antibody or PEG-anti-Aβ antibody fragment, and the anti-Tau antibody in the body.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. For example, an effective amount of anti-N3pGlu antibody may be determined based on achievement of significant amyloid reduction by florbetapir PET imagining (with an acceptable patient safety profile). An effective amount of anti-Aβ antibody or PEG-anti-Aβ antibody fragment may be determined based on extent of modeled free plasma Aβ lowering (with an acceptable patient safety profile). Further, for example, an effective amount of anti-Tau antibody may be determined based on achievement of slowing of progression of tau NFTs by tau PET imagine (with an acceptable patient safety profile).

In addition, the antibodies or fragments are generally effective over a wide dosage range in the combination of the present invention. In some instances, dosage levels below the lower limit of the aforesaid ranges may be more than adequate, while in other cases still larger doses may be employed with acceptable adverse events, and therefore the above dosage range is not intended to limit the scope of the invention in any way.

The antibodies or fragments of the present invention are preferably formulated as pharmaceutical compositions administered by any route which makes the antibodies bioavailable. The route of administration may be varied in any way, limited by the physical properties of the drugs and the convenience of the patient and the caregiver. Preferably, the pharmaceutical compositions are for parenteral administration, such as intravenous or subcutaneous administration. According to particular embodiments, the anti-N3pGlu Abeta antibody, anti-Aβ antibody or PEG-anti-Aβ antibody fragment may be administered subcutaneous and the anti-Tau antibody may be administered intravenous. In other particular embodiments, both the anti-N3pGlu Abeta antibody, anti-Aβ antibody or PEG-anti-Aβ antibody fragment, and the anti-Tau antibody, may both be administered intravenous or both be administered subcutaneous. Pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

As used herein, the phrase "in combination with" refers to the administration of an anti-N3pGlu Abeta antibody, anti-Aβ antibody or PEG-anti-Aβ antibody fragment, with anti-Tau antibody, such as simultaneously, or sequentially in any order, or any combination thereof. The two molecules may be administered either as part of the same pharmaceutical composition or in separate pharmaceutical compositions. The anti-N3pGlu Abeta antibody, anti-Aβ antibody or PEG-anti-Aβ antibody fragment can be administered prior to, at the same time as, or subsequent to administration of the anti-Tau antibody, or in some combination thereof.

As used herein, "BSA" refers to Bovine Serum Albumin; "EDTA" refers to ethylenediaminetetraacetic acid; "ee" refers to enantiomeric excess; "Ex" refers to example; "F12" refers to Ham's F12 medium; "hr" refers to hour or hours; "HRP" refers to Horseradish Peroxidase; "IC$_{50}$" refers to the concentration of an agent that produces 50% of the maximal inhibitory response possible for that agent; "min" refers to minute or minutes; "PBS" refers to Phosphate Buffered Saline; "PDAPP" refers to platelet derived amyloid precursor protein; "Prep" refers to preparation; "psi" refers to pounds per square inch; "R$_t$" refers to retention time; "SCX" refers to strong cation exchange chromatography; "THF" refers to tetrahydrofuran; and "TMB" refers to 3,3',5,5'-teramethylbenzidine.

EXAMPLES

The following examples are intended to illustrate but not to limit the invention.

Anti-Tau Antibody

Expression of Engineered Anti-Tau Antibodies

Engineered anti-Tau antibodies of the present invention can be expressed and purified essentially as follows. A glutamine synthetase (GS) expression vector containing the DNA sequence of SEQ ID NO.78 (encoding LC amino acid sequence of SEQ ID NO.67) and the DNA sequence of SEQ ID NO.77 (encoding HC amino acid sequence of SEQ ID NO.68) is used to transfect a Chinese hamster ovary cell line (CHO) by electroporation. The expression vector encodes an SV Early (Simian Virus 40E) promoter and the gene for GS. Expression of GS allows for the biochemical synthesis of glutamine, an amino acid required by the CHO cells. Post-transfection, cells undergo bulk selection with 50 µM L-methionine sulfoximine (MSX). The inhibition of GS by MSX is utilized to increase the stringency of selection. Cells with integration of the expression vector cDNA into transcriptionally active regions of the host cell genome can be selected against CHO wild type cells, which express an endogenous level of GS. Transfected pools are plated at low density to allow for close-to-clonal outgrowth of stable expressing cells. The masterwells are screened for antibody expression and then scaled up in serum-free, suspension cultures to be used for production.

Clarified medium, into which the antibody has been secreted, is applied to a Protein A affinity column that has been equilibrated with a compatible buffer, such as phosphate buffered saline (pH 7.4). The column is washed with 1M NaCl to remove nonspecific binding components. The bound anti-Tau antibodies are eluted, for example, with sodium citrate at pH (approx.) 3.5 and fractions are neutralized with 1M Tris buffer. Anti-Tau antibody fractions are detected, such as by SDS-PAGE or analytical size-exclusion, and then are pooled. Soluble aggregate and multimers may be effectively removed by common techniques, including size exclusion, hydrophobic interaction, ion exchange, or hydroxyapatite chromatography. The anti-Tau antibody of the present invention is concentrated and/or sterile filtered using common techniques. The purity of the anti-Tau antibody after these chromatography steps is greater than 95%. The anti-Tau antibody of the present invention may be immediately frozen at −70° C. or stored at 4° C. for several months.

Binding Kinetics and Affinity of Anti-Tau Antibody

Surface Plasmon Resonance (SPR) assay, measured with a BIACORE® 2000 instrument (primed with HBS-EP+ running buffer (GE Healthcare, 10 mM Hepes pH7.4+150 mM NaCl+3 mM EDTA+0.05% surfactant P20) at 25° C.), is used to measure binding of an exemplified anti-Tau antibody (having both HCs of SEQ ID NO.68 and both LCs of SEQ ID NO.67) to both human monomeric (e.g., native or non-aggregate) tau and human tau aggregates (both having the amino acid sequence as set forth in SEQ ID NO.79).

Except as noted, all reagents and materials are from BIACORE® AB (Upsala, Sweden). A CM5 chip containing immobilized protein A (generated using standard NHS-EDC amine coupling) on all four flow cells (FC) is used to employ a capture methodology. Antibody samples are prepared at 0.5 µg/mL by dilution into running buffer. Monomeric tau and fibril tau are prepared to concentrations of 2000, 1000, 500, 250, 125, 62.5, 31.25, 15.63, 7.82, 3.91, 1.95, and 0 (blank) nM by dilution into running buffer. Each analysis cycle consists of: (1) capturing antibody samples on separate flow cells (FC2, FC3, and FC4); (2) injection of 250 µL (300 sec) of either monomeric tau or tau fibril aggregate over respective FC at a rate of 50 µL/min; (3) return to buffer flow for 20 mins. to monitor dissociation phase; (4) regeneration of chip surfaces with 25 µL (30 sec) injection of glycine, pH1.5; (5) equilibration of chip surfaces with a 50 µL (60 sec) injection of HBS-EP+.

Data of binding to tau aggregate is processed using standard double-referencing and fit to a 1:1 binding model using Biacore 2000 Evaluation software, version 4.1, to determine the association rate ($k_{on}$, M$^{-1}$s$^{-1}$ units), dissociation rate ($k_{off}$, s$^{-1}$ units), and R$_{max}$ (RU units). The equilibrium dissociation constant ($K_D$) was calculated from the relationship $K_D=k_{off}/k_{on}$, and is in molar units. Data of binding to monomeric tau cannot be determined accurately by SPR as described above due to rapid on- and off-rates. Therefore, $K_D$ for binding to monomeric tau is obtained by using a steady state binding fit model from plotting the concentration of antigen versus the response unit. Resulting binding data is provided in Table 1.

TABLE 1

SPR binding data to both human monomeric and aggregate tau.

| | | $k_{on}$ ($M^{-1}s^{-1}$ units) | $k_{off}$ ($M^{-1}s^{-1}$ units) | $K_D^*$ (nM) |
|---|---|---|---|---|
| Exemplified anti-Tau mAb | Monomeric Tau | Not detectable | Not detectable | 235 |
| | Tau Aggregate | 4.59e4 | <1e-5 | <0.22 |

*$K_D$ results are considered relative as the results are not normalized for influence of avidity.

The results provided in Table 1 demonstrate the exemplified anti-Tau antibody does possess significant binding affinity to tau aggregate and does not possess measurable binding to monomeric tau such that an affinity value can be accurately determined by Biacore analysis (due to rapid on- and off-rates).

Enzyme-Linked Immunosorbant Assay (ELISA) is used to determine relative binding affinity of the exemplified anti-Tau antibody (having both HCs of SEQ ID NO.68 and both LCs of SEQ ID NO.67) to aggregate tau fibrils from AD brain homogenates. AD brain homogenates are prepared from approx. 80 g of cortex from brain of AD patients. Briefly, buffer (TBS/1 mM PMSF/1× Complete® protease inhibitor cocktail (Roche, p/n. 11 697 498 001) and phosphatase inhibitor (ThermoFischer, p/n. 78428)) is added to the AD brain tissue at about 10 ml/1 g (tissue). Tissue is homogenized using a handheld Kinematica Polytron at speed 6-7. Tissue is then further homogenized using Parr Bomb (Parr Instrument, p/n. 4653) at 1500 psi of nitrogen for 30 mins Homogenate is spun at 28,000 g (J14 Beckman rotor) for 30 min at 4° C. Supernatant is collected, pooled and run over a 4 cm high guard column of Sepharose 400 Superflow to remove larger debris, then run over 25 ml MC1-Affigel 10 column at a flow rate of 50-60 ml per hour, in order to purify MC1-binding tau fibrils. To maximize the recovery of purification, supernatants are recycled through MC-1 column over 18-20 hours at 4° C. Guard column is removed and MC1 column is washed with TBS with at least 40 column volumes. Bound tau aggregates are then eluted with 2 column volumes of 3M KSCN, collecting in approx. 1 ml fractions. Protein concentration in each eluted fraction is checked by microtiter plate Bradford assay. Fractions containing positive protein levels are pooled, concentrated to about 2 ml using Centricon (Millipore Ultracel-30K) at 4° C., and dialyzed using a Slide-A-Lyzer cassette (10K MWCO 3-12 ml, Pierce) overnight against 1 liter TBS. The concentration of tau within the tau fibrils purified from AD brain homogenate is measured by sandwich ELISA using DA-9 capture antibody and CP27 detection antibody.

Purified tau fibrils (50 µl) in PBS are coated on wells of 96-well plates (Coastar, p/n. 3690) at a concentration corresponding to 0.7 µg/ml of total tau. Plates are incubated overnight at 4° C., then washed three times with 150 µl of PBST (PBS containing 0.05% Tween-20), blocked in 100 µl BB3 (ImmunoChemistry Technology, p/n. 643) at room temperature for at least 1 hr (usually 2 hrs). Following blocking, the blocking buffer is removed from the wells. Exemplified anti-Tau antibody (having both HCs of SEQ ID NO. 68 and both LCs of SEQ ID NO.67) is diluted in 0.25% casein buffer to 1000 nM stock, then diluted serially 23 times with two fold dilutions. 50 µl of stock and serially diluted antibody are added to separate wells and incubated for 2 hours at room temperature, after which the plate is washed four times with 200 µl PBST per well. 50 µl of anti-human IgG-HRP antibodies (diluted at 1:4000 into 0.25% casein buffer) is added and incubated for 1 hour at room temperature, after which the plate is washed with 200 µl PBST per well 4 times. 50 µl of TMB/H2O2 is added and incubated at room temperature for about 10 minutes. Reaction is stopped by adding 50 µl stop solution (2N H2SO4) and colorimetric signal is measured at 450 nm. Data is input into Prism 6 (GraphPad) program and $EC_{50}$ values are generated using a nonlinear regression curve fit and sigmoidal dose response. Results are presented in Table 2.

TABLE 2

$EC_{50}$ Comparison of Binding to Purified AD Tau Fibrils

| Antibody Assayed | $EC_{50}$ (pM) |
|---|---|
| Exemplified anti-Tau mAb | 6.8 |

As reflected in Table 2, exemplified tau monoclonal antibody of the present invention demonstrates significant affinity (as measured by $EC_{50}$) to purified tau fibrils.

Ex Vivo Target Engagement Studies

Binding of exemplified anti-Tau antibody (having both HCs of SEQ ID NO.68 and both LCs of SEQ ID NO.67) to aggregated tau derived from human brains is determined through immunohistochemistry staining of formalin-fixed paraffin-embedded (FFPE) brain sections obtained from: a "normal" individual (displaying minimal tau aggregation); an AD patient (displaying severe tau aggregation and NFT formation, as well as amyloid plaque pathology); a PD patient (displaying severe tau aggregation). Staining is also performed on brain sections derived from a "control" wild type mouse that possess no human tau in order to determine background non-specific staining levels.

FFPE sections are de-paraffinized and rehydrated. Thereafter, antigen retrieval (using the Lab Vision PT module system, Thermo Scientific) is performed on the sections which includes heating sections in citrate buffer (Thermo Scientific, p/n. TA-250-PM1X) for 20 minutes at 100° C. then cooling the sections in dH20. Sections are then exposed to the following seven incubation steps (at room temp.): (1) 10 min. in 0.03% H2O2; (2) 30 min. in 1:20 dilution of normal goat serum (Vector Labs., p/n. S-1000) diluted in PBST; (3) 60 min. in exemplified anti-Tau antibody (normalized to 1 mg/ml, then diluted in PBST to a dilution of 1:4000 before incubation with sections); (4) 30 min. in rabbit anti-human IgG4 (raised against the Fc region of the exemplified antibody) at a concentration of 1.1 µg/ml in PBST; (5) 30 min in 1:200 dilution of biotinylated goat anti-rabbit IgG (Vector Labs., p/n. BA-1000) diluted in PBST: (6) 30 min in avidin-biotin complex solution (Vector Labs., p/n. PK-7100); (7) 5 min. in 3,3'-diaminobenzidine (Vector Labs., p/n. SK-4105). Sections are washed between each of the above 7 steps using PBST. Following the seven incubation steps above, sections are counterstained with haematoxylin, dehydrated and cover-slipped. For mouse "control" tissue sections the above protocol is modified in incubation step (3) by using a 1:8000 dilution (as opposed to a 1:4000 dilution) of exemplified anti-Tau antibody; and by replacing incubation steps (4) and (5) with a single 30 min 1:200 dilution of biotinylated goat anti-human IgG (Vector Labs. p/n. BA-3000) in PBST.

Following procedures substantially as described above, an analysis of the binding of the exemplified anti-Tau antibody to tau derived from human brains is performed. Results are provided in Table 3.

TABLE 3

Semi-quantitative analysis of binding to aggregated tau in FFPE AD brain sections.

| | Severity of aggregated tau detected as measured by semi quantitative scoring scheme (severe, +++; moderate, ++; mild, +; negative, −) | | | |
|---|---|---|---|---|
| | WT control (murine) | Normal control (human) | Alzheimer's disease | Pick's disease |
| Exemplified anti-Tau mAb | − | + | +++ | +++ |

The results provided in Table 3 reflect that exemplified anti-Tau antibody demonstrates significantly higher levels of staining to aggregated tau, from both AD and PD patients, in hippocampal brain sections as compared to the control sample Further, because AD and PD are characterized by distinct splicing variants of the gene encoding tau, these results support a conclusion that exemplified anti-Tau antibody specifically binds the conformational epitope comprising amino acid residues 7-9 and 312-322 of human tau (residue numbering based on the exemplified human tau of SEQ ID NO.79) common to tau aggregates of both AD and PD.

In Vivo Neutralization of Tau Aggregate Propagation

Homogenate brain stem preps from approx. 5 month old P301S mice are known to, upon injection into hippocampus of normal 10 week old female P301S mice, induce aggregation of native, non-aggregate tau, demonstrating a propagation-like effect of tau aggregation. Homogenate preps of brain stem tissue from 4.5 to 5 month old P301S mice are prepared substantially the same as described above.

Normal 10 week old female P301S mice are injected in the left hemisphere of the hippocampus with 5 μl homogenate brain prep and either: 7.5 μg exemplified anti-Tau antibody (having both HCs of SEQ ID NO.68 and both LCs of SEQ ID NO.67) (N=12); or 7.5 μg of control human IgG4 antibody (N=11). Four weeks post-injection, the mice are sacrificed and the left and right hemispheres are collected, paraffin embedded, and 6 μm serial sections are mounted on glass slides. Slides containing bregma (A-P=−2.30) are de-paraffinized, embedded tissue is rehydrated, and antigen retrieval is performed by heating slide to 100° C. for 20 min. in citrate buffer. Slides are cooled in dH$_2$O and incubated at room temperature according to the following steps: (a) 10 min. in (0.03%) H2O2; (b) 30 min. in a 1:20 dilution of normal goat serum; (c) 60 min. in a 1:8000 dilution of PG-5 antibody (diluted in PBST) (PG-5 antibody obtained from the lab of Dr. Peter Davies, Albert Einstein College of Medicine of Yeshiva University; PG-5 antibody specifically binds serine at residue 409 of tau when phosphorylated, residue numbering based on the exemplified human tau of SEQ ID NO.79); (d) 30 min in a 1:200 dilution of biotinylated goat anti-mouse IgG antibody (diluted in PB ST); (e) 30 min. in avidin-biotin complex solution; and (f) 5 min in 3,3'-diaminobenzidine. PBST is used for washing between the respective steps. Following the 5 min. incubation in 3,3'-diaminobenzidine, sections are counterstained with haematoxylin, then rehydrated and cover-slipped. Staining signal is measured by Scanscope AT Slide Scanner (Aperio) at 20× magnification. PG-5 immunoreactivity is quantified and expressed as a percentage using the positive pixel algorithm of Imagescope Software (v. 11.1.2.780, Aperio). Results are provided in Table 4.

TABLE 4

Mean % PG-5 immunoreactivity in left and right hippocampus, respectively.

| | (% PG-5 Immunoreactivity) | |
|---|---|---|
| | Left Hippocampus | Right Hippocampus |
| Exemplified anti-Tau mAb | 2.52 ± 0.49 SEM | 0.63 ± 0.13 SEM |
| Control IgG4 Ab | 6.38 ± 0.93 SEM | 1.88 ± 0.31 SEM |

The results provided in Table 4 demonstrate the exemplified anti-Tau antibody reduces the level of tau aggregation in both the left and right hippocampus as compared to the control IgG4 antibody. As shown, the exemplified anti-Tau antibody produces a 60.5% greater reduction in tau aggregation in the left hippocampus, and a 66.5% greater reduction in tau aggregation in the right hippocampus, respectively, compared to control IgG4 antibody. These results demonstrate the exemplified anti-Tau antibody possesses neutralizing activity against propagation of tau aggregation.

Anti-N3pGlu Aβ Antibody

Expression and Purification of Engineered Anti-N3pGlu Aβ Antibodies

Anti-N3pGlu Aβ antibodies (for example, Antibody I or II) of the present invention can be expressed and purified essentially as follows. A glutamine synthetase (GS) expression vector containing the DNA sequence encoding the LC amino acid sequence of SEQ ID NO: 12 or 13 and the DNA sequence encoding the HC amino acid sequence of SEQ ID NO: 11 is used to transfect a Chinese hamster ovary cell line (CHO) by electroporation. The expression vector encodes an SV Early (Simian Virus 40E) promoter and the gene for GS. Post-transfection, cells undergo bulk selection with 0-50 μM L-methionine sulfoximine (MSX). Selected bulk cells or master wells are then scaled up in serum-free, suspension cultures to be used for production.

Clarified medium, into which the antibody has been secreted, is applied to a Protein A affinity column that has been equilibrated with a compatible buffer, such as phosphate buffered saline (pH 7.4). The column is washed with 1 M NaCl to remove nonspecific binding components. The bound anti-N3pGlu Aβ antibody is eluted, for example, with sodium citrate at pH (approx.) 3.5 and fractions are neutralized with 1 M Tris buffer. Anti-N3pGlu Aβ antibody fractions are detected, such as by SDS-PAGE or analytical size-exclusion, and then are pooled. Anti-N3pGlu Aβ antibody (Antibody I or Antibody II) of the present invention is concentrated in either PBS buffer at pH 7.4 or 10 mM NaCitrate buffer, 150 mM NaCl at pH around 6. The final material can be sterile filtered using common techniques. The purity of the anti-N3pGlu Aβ antibody is greater than 95%. The anti-N3pGlu Aβ antibody (Antibody I or Antibody II) of the present invention may be immediately frozen at −70° C. or stored at 4° C. for several months.

Binding Affinity and Kinetics of Anti-N3pGlu Aβ Antibodies

The binding affinity and kinetics of an anti-N3pGlu Aβ antibody (Antibody I or Antibody II) to pE3-42 Aβ peptide or to Aβ 1-40 peptide is measured by surface plasmon resonance using BIACORE® 3000 (GE Healthcare). The binding affinity is measured by capturing the anti-N3pGlu Aβ antibody via immobilized protein A on a BIACORE® CM5 chip, and flowing pE3-42 Aβ peptide or Aβ 1-40 peptide, starting from 100 nM in 2-fold serial dilution down to 3.125 nM. The experiments are carried out at 25° C. in HBS-EP buffer (GE Healthcare BR100669; 10 mM HEPES, 150 mM NaCl, 3 mM EDTA, 0.05% surfactant P20, pH 7.4).

For each cycle, the antibody is captured with 5 µL injection of antibody solution at a 10 µg/mL concentration with 10 µL/min flow rate. The peptide is bound with 250 µL injection at 50 µL/min, and then dissociated for 10 minutes. The chip surface is regenerated with 5 µL injection of glycine buffer at pH 1.5 at 10 µL/mL flow rate. The data is fit to a 1:1 Langmiur binding model to derive $k_{on}$, $k_{off}$, and to calculate $K_D$. Following procedures essentially as described above, the following parameters (shown in Table 5) were observed.

TABLE 5

Binding affinity and kinetics of anti-N3pGlu Aβ Antibodies.

| Antibody | $k_{on}$ (×10$^5$ 1/MS) | $k_{off}$ (×10$^{-4}$ 1/s) | $K_D$ (nM) |
|---|---|---|---|
| I | 1.39 | 1.31 | 0.71 |
| II | 3.63 | 1.28 | 0.35 |

No appreciable binding to Aβ 1-40 was detected, indicating that Antibody I and Antibody II bound specifically to pE3-42 Aβ peptide as compared to Aβ 1-40.

Ex Vivo Target Engagement of Anti-N3pGlu Aβ Antibodies

To determine ex vivo target engagement on brain sections from a fixed PDAPP brain, immunohistochemical analysis is performed with an exogenously added anti-N3pGlu Aβ antibody (Antibody I or Antibody II). Cryostat serial coronal sections from aged PDAPP mice (25-month old) are incubated with 20 µg/mL of an exemplified N3pGlu Aβ antibody of the present invention (Antibody I or Antibody II). Secondary HRP reagents specific for human IgG are employed and the deposited plaques are visualized with DAB-Plus (DAKO). Biotinylated murine 3D6 antibody followed by Step-HRP secondary is used as a positive control. The positive control antibody (biotinylated 3D6) labeled significant quantities of deposited Aβ in the PDAPP hippocampus, and the anti-N3pGlu Aβ antibodies (Antibody I or Antibody II) labeled a subset of deposits. These histological studies demonstrated that the anti-N3pGlu Aβ antibodies (Antibody I and Antibody II) engaged deposited Aβ target ex vivo.

Anti-Aβ Antibody

Synthesis of Exemplified Anti-Aβ Antibody

Cells and antibodies. Mouse myeloma cell line Sp2/0 was obtained from ATCC (Manassas, Va.) and maintained in DME medium containing 10% FBS (Cat #SH32661.03, HyClone, Logan, Utah) in a 37° C. CO$_2$ incubator. Mouse 266 hybridoma cells were first grown in RPMI-1640 medium containing 10% FBS (HyClone), 10 mM HEPES, 2 mM glutamine, 0.1 mM non-essential amino acids, 1 mM sodium pyruvate, 25 µg/ml gentamicin, and then expanded in serum-free media (Hybridoma SFM, Cat #12045-076, Life Technologies, Rockville, Md.) containing 2% low FBS (Cat #30151.03, HyClone) to a 2.5 liter volume in roller bottles. Mouse monoclonal antibody 266 (Mu266) was purified from the culture supernatant by affinity chromatography using a protein-G Sepharose column. Biotinylated Mu266 was prepared using EZ-Link Sulfo-NHS-LC-LC-Biotin (Cat #21338ZZ, Pierce, Rockford, Ill.).

Cloning of variable region cDNAs. Total RNA was extracted from approximately 10$^7$ hybridoma cells using TRIzol reagent (Life Technologies) and poly(A)$^+$ RNA was isolated with the PolyATract mRNA Isolation System (Promega, Madison, Wis.) according to the suppliers' protocols. Double-stranded cDNA was synthesized using the SMART™ RACE cDNA Amplification Kit (Clontech, Palo Alto, Calif.) following the suppliers protocol. The variable region cDNAs for the light and heavy chains were amplified by polymerase chain reaction (PCR) using 3' primers that anneal respectively to the mouse kappa and gamma chain constant regions, and a 5' universal primer provided in the SMARTTMRACE cDNA Amplification Kit. For VL PCR, the 3' primer has the sequence:

[SEQ ID NO: 51]
5'-TATAGAGCTCAAGCTTGGATGGTGGGAAGATGGATACAGTTGGTGC-3' with residues 17-46 hybridizing to the mouse Ck region. For VH PCR, the 3' primers have the degenerate sequences:

[SEQ ID NO: 52]
```
                                              A       G   T
5'-TATAGAGCTCAAGCTTCCACTGGATAGACCGATGGGGCTGTCGTTTTGGC-3'
                                                      T
``` with residues 17-50 hybridizing to mouse gamma chain CHI. The VL and VH cDNAs were subcloned into pCR4Blunt-TOPO vector (Invitrogen, Carlsbad, Calif.) for sequence determination. DNA sequencing was carried out by PCR cycle sequencing reactions with fluorescent dideoxy chain terminators (Applied Biosystems, Foster City, Calif.) according to the manufacturer's instruction. The sequencing reactions were analyzed on a Model 377 DNA Sequencer (Applied Biosystems).

Construction of humanized 266 (Hu266) variable regions. Humanization of the mouse antibody V regions was carried out as outlined by Queen et al. [*Proc. Natl. Acad. Sci. USA* 86:10029-10033 (1988)]. The human V region framework used as an acceptor for Mu266 CDRs was chosen based on sequence homology. The computer programs ABMOD and ENCAD [Levitt, M., J. Mol. Biol. 168:595-620 (1983)] were used to construct a molecular model of the variable regions. Amino acids in the humanized V regions that were predicted to have contact with CDRs were substituted with the corresponding residues of Mu266. This was done at residues 46, 47, 49, and 98 in the heavy chain and at residue 51 in the light chain. The amino acids in the humanized V region that were found to be rare in the same V-region subgroup were changed to the consensus amino acids to eliminate potential immunogenicity. This was done at residues 42 and 44 in the light chain.

The light and heavy chain variable region genes were constructed and amplified using eight overlapping synthetic oligonucleotides ranging in length from approximately 65 to 80 bases [He, X. Y., et al., J. Immunol. 160: 029-1035 (1998)]. The oligonucleotides were annealed pairwise and extended with the Klenow fragment of DNA polymerase I, yielding four double-stranded fragments. The resulting fragments were denatured, annealed pairwise, and extended with Klenow, yielding two fragments. These fragments were denatured, annealed pairwise, and extended once again, yielding a full-length gene. The resulting product was amplified by PCR using the Expand High Fidelity PCR System (Roche Molecular Biochemicals, Indianapolis, Ind.). The PCR-amplified fragments were gel-purified and cloned into pCR4Blunt-TOPO vector. After sequence confirmation, the VL and VH genes were digested with MluI and XbaI, gel-purified, and subcloned respectively into vectors for expression of light and heavy chains to make pVk-Hu266 and pVg1-Hu266 [Co, M. S., et al., J. Immunol. 148:1149-1154 (1992)]. The mature humanized 266 antibody (Hu266) expressed from these plasmids has the light chain of SEQ ID NO:49 and the heavy chain of SEQ ID NO:50.

Stable transfection. Stable transfection into mouse myeloma cell line Sp2/0 was accomplished by electroporation using a Gene Pulser apparatus (BioRad, Hercules, Calif.) at 360 V and 25 pF as described (Co et al., 1992). Before transfection, pVk-Hu266 and pVg1-Hu266 plasmid DNAs were linearized using FspI. Approximately $10^7$ Sp2/0 cells were transfected with 20 g of pVk-1-Hu266 and 40 µg of pVg1-Hu266. The transfected cells were suspended in DME medium containing 10% PBS and plated into several 96-well plates. After 48 hr, selection media (DME medium containing 10% FBS, HT media supplement, 0.3 mg/ml xanthine and 1 µg/ml mycophenolic acid) was applied. Approximately 10 days after the initiation of the selection, culture supernatants were assayed for antibody production by ELISA as shown below. High yielding clones were expanded in DME medium containing 10% FBS and further analyzed for antibody expression. Selected clones were then adapted to growth in Hybridoma SFM.

Measurement of antibody expression by ELISA. Wells of a 96-well ELISA plate (Nunc-Immuno plate, Cat #439454, NalgeNunc, Naperville, Ill.) were coated with 100 µl of 1 µg/ml goat anti-human IgG, Fcγ fragment specific, polyclonal antibodies (Cat #109-005-098, Jackson ImmunoResearch, West Grove. Pa.) in 0.2 M sodium carbonate-bicarbonate buffer (pH 9.4) overnight at 4° C. After washing with Washing Buffer (PBS containing 0.1% Tween 20), wells were blocked with 400 µl of Superblock Blocking Buffer (Cat #37535, Pierce) for 30 min and then washed with Washing Buffer. Samples containing Hu266 were appropriately diluted in ELISA Buffer (PBS containing 1% BSA and 0.1% Tween 20) and applied to ELISA plates (100 µl per well). As a standard, humanized anti-CD33 IgG monoclonal antibody HuM195 (Co, et al., 1992, above) was used. The ELISA plate was incubated for 2 hr at room temperature and the wells were washed with Wash Buffer. Then, 100 µl of 1/1,000-diluted HRP-conjugated goat antihuman kappa polyclonal antibodies (Cat #1050-05, Southern Biotechnology, Birmingham, Ala.) in ELISA Buffer was applied to each well. After incubating for 1 hr at room temperature and washing with Wash Buffer, 100 µl of ABTS substrate (Cat #s 507602 and 506502, Kirkegaard and Perry Laboratories, Gaithersburg, Md.) was added to each well. Color development was stopped by adding 100 µl of 2% oxalic acid per well. Absorbance was read at 415 nm using an OPTImax microplate reader (Molecular Devices. Menlo Park, Calif.).

Purification of Hu266. One of the high Hu266-expressing Sp2/0 stable transfectants (clone 1D9) was adapted to growth in Hybridoma SFM and expanded to 2 liter in roller bottles. Spent culture supernatant was harvested when cell viability reached 10% or below and loaded onto a protein-A Sepharose column. The column was washed with PBS before the antibody was eluted with 0.1 M glycine-HCl (pH 2.5), 0.1 M NaCl. The eluted protein was dialyzed against 3 changes of 2 liter PBS and filtered through a 0.2 µm filter prior to storage at 4° C. Antibody concentration was determined by measuring absorbance at 280 nm (1 mg/ml=1.4 $A_{280}$). SDS-PAGE in Tris-glycine buffer was performed according to standard procedures on a 4-20% gradient gel (Cat #EC6025, Novex, San Diego, Calif.). Purified humanized 266 antibody is reduced and run on an SDSPAGE gel. The whole antibody shows two bands of approximate molecular weights 25 kDa and 50 kDa. These results are consistent with the molecular weights of the light chain and heavy chain or heavy chain fragment calculated from their amino acid compositions.

In Vitro Binding Properties of Exemplified Anti-Aβ Antibody

The binding efficacy of humanized 266 antibody (Hu266), synthesized and purified as described above, was compared with the mouse 266 antibody (Mu266) using biotinylated mouse 266 antibody in a comparative ELISA. Wells of a 96-well ELISA plate (Nunc-immuno plate, Cat #439454, NalgeNunc) were coated with 100 µl of β-amyloid peptide (1-42) conjugated to BSA in 0.2 M sodium carbonate/bicarbonate buffer (pH 9.4) (10 µg/mL) overnight at 4° C. The $Aβ_{1-42}$-BSA conjugate was prepared by dissolving 7.5 mg of $Aβ_{1-42}$-$Cys_{43}$ (C-terminal cysteine $Aβ_{1-42}$, AnaSpec) in 500 µL of dimethylsulfoxide, and then immediately adding 1,500 µL of distilled water. Two (2) milligrams of maleimide-activated bovine serum albumin (Pierce) was dissolved in 200 µL of distilled water. The two solutions were combined, thoroughly mixed, and allowed to stand at room temperature for two (2) hours. A gel chromatography column was used to separate unreacted peptide from $Aβ_{1-42}$-Cys-BSA conjugate.

After washing the wells with phosphate buffered saline (PBS) containing 0.1% Tween 20 (Washing Buffer) using an ELISA plate washer, the wells were blocked by adding 300 µL of SuperBlock reagent (Pierce) per well. After 30 minutes of blocking, the wells were washed Washing Buffer and excess liquid was removed.

A mixture of biotinylated Mu266 (0.3 µg/ml final concentration) and competitor antibody (Mu266 or Hu266; starting at 750 µg/ml final concentration and serial 3-fold dilutions) in ELISA Buffer were added in triplicate in a final volume of 100 µl per well. As a no-competitor control, 100 µl of 0.3 µg/ml biotinylated Mu266 was added. As a background control, 100 µl of ELISA Buffer was added. The ELISA plate was incubated at room temperature for 90 min. After washing the wells with Washing Buffer, 100 µl of 1 µg/ml HRP-conjugated streptavidin (Cat #21124, Pierce) was added to each well. The plate was incubated at room temperature for 30 min and washed with Washing Buffer. For color development, 100 µl/well of ABTS Peroxidase Substrate (Kirkegaard & Perry Laboratories) was added. Color development was stopped by adding 100 µl/well of 2% oxalic acid. Absorbance was read at 415 nm. The absorbances were plotted against the log of the competitor concentration, curves were fit to the data points (using Prism) and the IC50 was determined for each antibody using methods well-known in the art.

The mean IC50 for mouse 266 was 4.7 µg/mL (three separate experiments, standard deviation=1.3 µg/mL) and for humanized 266 was 7.5 µg/mL (three separate experiments, standard deviation=1.1 µg/mL). A second set of three experiments were carried out, essentially as described above, and the mean IC50 for mouse 266 was determined to be 3.87 µg/mL (SD=0.12 µg/mL) and for human 266, the IC50 was determined to be 4.0 µg/mL (SD=0.5 µg/mL). On the basis of these results, we conclude that humanized 266 has binding properties that are very similar to those of the mouse antibody 266. Therefore, we expect that humanized 266 has very similar in vitro and in vivo activities compared with mouse 266 and will exhibit in humans the same effects demonstrated with mouse 266 in mice.

The affinity (KD=Kd/Ka) of humanized 266 antibody, synthesized and purified as described above, for $A\beta_{1-42}$ was determined essentially as described above. Using the above-described method, the affinity of humanized 266 for $A\beta_{1-42}$ was found to be 4 pM.

Sequestration of Added Aβ Peptide in Human Fluids

Samples of human cerebrospinal fluid (CSF) (50 μl) and human plasma (50 μl) were incubated for 1 hour at room temperature as follows:

1. alone;
2. along with 5 ng Aβ 40 peptide; or
3. 5 ng Aβ 40 peptide plus 1 mg monoclonal antibody 266 (described, for example, in U.S. Pat. No. 5,766,846 incorporated herein by reference).

The samples were then electrophoresed on a 4-25% non-denaturing gradient gel, i.e., non-denaturing gradient electrophoresis (NDGGE) and transferred to nitrocellulose. The blots were then stained with Ponceau S or, for Western blot, probed with biotin-labeled monoclonal antibody (3D6) which is directed against the first five amino acids of Aβ peptide, developed with streptavidin-horse radish peroxidase and detected by enhanced chemiluminescence (ECL). The hydrated diameters of the materials contained in bands on the blots were estimated using Pharmacia molecular weight markers. Thus, if the Aβ peptide is bound to other molecules, it would run at the size of the resulting complex.

Western blots of CSF either with or without 5 ng Aβ peptide shows no evidence of the Aβ peptide in response to detection mediated by antibody 3D6. Similar results are obtained for human plasma. This was true despite the fact that Aβ peptide could be detected by SDS-PAGE followed by Western blot using the same technique and on the same CSF samples. Presumably, the detection of Aβ peptide was prevented by interactions between this peptide and other factors in the fluids tested. However, when Mab 266 is added to the incubation, characteristic bands representing sequestered Aβ peptide complexed to the antibody are present both in plasma and in CSF. The major band is at approximately 11 nm hydrated diameter, corresponding to antibody monomer with an additional smaller band at 13 nm corresponding to antibody dimer.

Specificity of the Sequestering Antibody

Samples containing 50 μl of human CSF or 10 μl of $APP^{V717F}$ CSF were used. $APP^{V717F}$ are transgenic mice representing a mouse model of Alzheimer's disease in which the human amyloid precursor protein transgene with a familial Alzheimer's disease mutation is expressed and results in the production of human Aβ peptide in the central nervous system.

The samples were incubated with or without various Mabs (1 μg) for 1 hour at room temperature and then electrophoresed on a 4-25% NDGGE and blotted onto nitrocellulose as described above (Sequestration of Added Aβ Peptide in Human Fluids). The antibodies were as follows:

Mab 266 (binds to positions 13-28);
Mab 4G8 (binds to positions 17-24);
QCBpan (rabbit polyclonal for positions 1-40);
mouse IgG (non-specific);
Mab 3D6 (binds to positions 1-5);
Mab 21F12 (binds to positions 33-42):
Mab 6E10 (binds to positions 1-17); and
$QCB_{40,42}$ (rabbit polyclonals to $A\beta_{40}$ and $A\beta_{42}$).

Detection of the Aβ peptide antibody complex was as described above (in Sequestration of Added Aβ Peptide in Human Fluids). Similar detection in human CSF incubated with Mab 266, in some instances substituted $QCB_{40,42}$, which binds to the carboxyl terminus of Aβ peptide, for 3D6.

The results showed that of the antibodies tested, only Mab 4G8 and Mab 266 permitted the detection of Aβ peptide.

The results showed that for human CSF, only Mab 266 and Mab 4G8 were able to sequester in detectable amounts of an antibody Aβ complex (again, without any antibody, no Aβ is detected). Mab 266 was also able to produce similar results to those obtained with human CSF with CSF from $APP^{V717F}$ transgenic mice. Aβ peptide could be sequestered in human CSF using Mab 266 regardless of whether 3D6 or $QCB_{40,42}$ antibody was used to develop the Western blot.

Sequestration of Aβ Peptide In Vivo

A. Transgenic $APP^{V717F}$ mice, also termed PDAPP mice, over-express a mutant form of human APP protein. These mice produce human Aβ in the CNS and have elevated levels of human Aβ peptide circulating in the CSF and plasma. Eight month old mice were injected intravenously with saline or 100 μg of Mab 266. They were bled 10 minutes after initial injection and again at 20 hours after initial injection.

Samples containing 20 μl of plasma from each animal were analyzed by NDGGE and Western blot with antibody 3D6 as described above (Sequestration of Added Aβ Peptide in Human Fluids). The saline injected animals did not show the presence of the characteristic 11 nm sequestered Aβ peptide band either after 10 minutes or 20 hours. However, the two animals that were injected with Mab 266 did show the appearance of this band after 20 hours.

B. Two month old $APP^{V717F}$ mice were used in this study. At day zero, the mice received either no Mab 266, 1 mg Mab 266, or 100 μg of this antibody. Plasma samples were taken two days prior to administration of the antibodies and on days 1, 3, 5 and 7. The plasma samples were subjected to NDGGE followed by Western blotting and detection with 3D6 as described above (Sequestration of Added Aβ Peptide in Human Fluids). At all-time points following administration of Mab 266, the 266/Aβ complex was detected unless the plasma sample had been treated with protein G, which binds to immunoglobulin, thus effectively removing the Mab 266. Consistent levels of complex over the time period tested were found except for a slight drop-off at day seven in animals injected with 100 μg of Mab 266; in general, the levels in animals administered 100 μg were consistently lower than those found in the mice administered 1 mg of this antibody.

C. Two two-month old $APP^{V717F}$ mice were administered 1 mg of Mab 266 intravenously and a 25 μl plasma sample was taken from each. The plasma sample was subjected to NDGGE followed by Western blot as described above except that binding with biotinylated 3D6 was followed by detection with streptavidin $^{125}$I (Amersham) and exposure to a phosphorimaging screen. The level of complex was estimated in comparison to a standard curve using known amounts of $A\beta_{40}$ complexed with saturating levels of Mab 266 and detected similarly. The amount of Aβ peptide bound to Mab 266 was estimated at approximately 100 ng/ml, representing an increase of approximately 1,000-fold over endogenous Aβ peptide in these mice which had been determined to be about 100 pg/ml. This is also similar to the level of Aβ peptide in $APP^{V717F}$ brain prior to Aβ deposition (50-100 ng/g); human AβP and human Aβ in $APP^{V717F}$ Tg mice are produced almost solely in the brain. Thus, it appears that the presence of Mab 266 in the plasma acts as an Aβ peptide sink facilitating net efflux of Aβ peptide from the CNS into the plasma. This increased net efflux likely results from both increasing Aβ efflux from CNS to plasma and also from preventing Aβ in plasma from re-entering the brain.

The correct size for the sequestered Aβ peptide was confirmed by running 20 μL of plasma samples obtained from APP$^{V717F}$ mice 24 hours after being injected with 1 mg Mab 266 on TRIS-tricine SDS-PAGE gels followed by Western blotting using anti-Aβ antibody 6E10 prior to, or after, protein G exposure using protein G-bound beads. A band that was depleted by protein G was detected at 4-8 kD, consistent with the presence of monomers and possibly dimers of Aβ peptide.

D. Two month old APP$^{V717F}$ mice were treated with either PBS (n=7) or 500 pg biotinylated Mab 266—i.e., m266B (n=9) intraperitoneally. Both prior to and 24 hours after the injection, plasma was analyzed for total Aβ peptide using a modification of the ELISA method of Johnson-Wood, K., et al., *Proc. Natl. Acad. Sci. USA* (1997). 94:1550-1555; and Bales, K. R., et al., *Nature Genet* (1997) 17:263-264. Total Aβ bound to m266B was measured by using 96-well Optiplates (Packard, Inc.) coated with m3D6. Diluted plasma samples and standards (varying concentrations of Aβ$_{40}$ and m266B) were incubated overnight in the coated plates and the amount of total Aβ/m266B complex was determined with the use of $^{125}$I-Streptavidin. In addition, at the 24-hour time point, the plasma samples were first treated with protein G to quantitate Aβ peptide not bound to Mab 266, and Aβ$_{Total}$ and Aβ$_{42}$ were determined by ELISA in the CSF. In PBS-injected animals, plasma Aβ peptide levels were 140 pg/ml both before and after injection. Plasma levels were similar in the Mab 266-injected mice prior to injection, but levels of Aβ peptide not bound to Mab 266 were undetectable at 24 hours post injection.

Levels in the CSF were also measured. CSF represents an extracellular compartment within the CNS and concentration of molecules in the CSF reflects to some extent the concentration of substances in the extracellular space of the brain. CSF was isolated from the cisterna magna compartment. Mice were anesthetized with pentobarbital and the musculature from the base of the skull to the first vertebrae was removed. CSF was collected by carefully puncturing the arachnoid membrane covering the cistern with a micro needle under a dissecting microscope and withdrawing the CSF into a polypropylene micropipette. At 24 hours post injection, an increase in total Aβ peptide in the CSF of Mab 266-injected mice was found, and an approximately two-fold increase in Aβ$_{42}$ as compared to PBS injected mice was obtained in the CSF. This was confirmed using denaturing gel electrophoresis followed by Western blotting with Aβ$_{42}$-specific antibody 21F12.

In an additional experiment, three month old APP$^{V717F}$ Tg mice were injected with either PBS or Mab 266 intravenously and both Aβ$_{40}$ and Aβ$_{42}$ levels were assessed in the CSF as follows:

For measurement of Aβ$_{40}$, the monoclonal antibody m2G3, specific for Aβ$_{40}$ was utilized. The ELISA described (Johnson-Wood, K., et al., *Proc. Natl. Acad. Sci. USA* (1997) 94:1550-1555) was modified into an RIA by replacing the Streptavidin-HRP reagent with $^{125}$I-Streptavidin. For plasma and CSF samples, the procedure was performed under non-denaturing conditions that lacked guanidine in the buffers. For assessment of carbonate soluble and insoluble Aβ in brain homogenate, samples were homogenized with 100 mM carbonate, 40 mM NaCl, pH 11.5 (4° C.), spun at 10,000×g for 15 min, and Aβ was assessed in the supernatant (soluble) and the pellet (insoluble) fractions as described (Johnson-Wood, K., et al., *Proc. Natl. Acad. Sci. USA* (1997) 94:1550-1555) and listed above. The measurement of Aβ/Mab 266 complex in plasma was performed by a modified RIA. Mice were injected with biotinylated Mab 266 (Mab 266B) and plasma was isolated at multiple time points. Total Aβ bound to Mab 266 was measured by using 96-well Optiplates (Packard, Inc.) coated with m3D6. Diluted plasma samples and standards (varying concentrations of Aβ$_{40}$ and Mab 266B) were incubated overnight in the coated plates and the amount of total Aβ/Mab 266B complex was determined with the use of $^{125}$I-Streptavidin.

Three hours following the intravenous injection of Mab 266, there was a two-fold increase in CSF Aβ$_{40}$ levels and a non-significant increase in Aβ$_{42}$. However, at both 24 and 72 hours there was a two to three-fold increase in both Aβ$_{40}$ and Aβ$_{42}$ in the CSF. Similar results were obtained using denaturing gel analysis followed by Aβ Western blotting of pooled CSF. The efflux of Aβ through brain interstitial fluid, which is reflected to some degree by CSF levels, likely accounts for the observed increase in CSF Aβ.

It is significant that the change in CSF Aβ peptide levels cannot be due to entry of Mab 266 into the CSF since the levels measured 24 hours after injection, which are less than 0.1% plasma levels of Mab 266, are insufficient to account for the changes. These results suggest Aβ peptide is withdrawn from the brain parenchyma into the CSF by the presence of the antibody in the bloodstream.

Forms of Aβ peptide which are soluble in PBS or carbonate buffer were measured in cerebral cortical homogenates in the same mice which had been injected with Mab 266 and in which the CSF was analyzed as described above. Similar increases in these soluble forms in the cortical homogenates were observed.

Mab 266 Effect on Aβ in the Brain

Four month old APP$^{V717F}$+/+ mice were treated every 2 weeks for 5 months with IP injections of saline, Mab 266 (500 μg), or control mouse IgG (100 μg, Pharmingen). The mice were sacrificed at nine months of age, and Aβ deposition in the cortex was determined. The % area covered by Aβ-immunoreactivity, as identified with a rabbit pan-Aβ antibody (QCB, Inc.), was quantified in the cortex immediately overlying the dorsal hippocampus as described by Holtzman, D. M., et al., *Ann. Neurol.* (2000) 97:2892-2897. At this age, about half of each group has still not begun to develop Aβ deposition. However, the % of mice with >50% Aβ burden in the cortex was significantly less (P=0.02, Chi-square test) in the 266-treated group. While APP$^{V717F}$ mice can develop large amounts of Aβ deposits by nine months, there is great variability with about 50% showing no deposits and about 50% showing substantial deposits. In PBS and IgG treated animals, 6/14 and 5/13 mice had greater than 50% of the cortex covered by Aβ staining, while only one of 14 mice treated with Mab 266 had this level of staining. Almost 50% of the animals in all groups still had not developed Aβ deposition by 9 months of age. The latter appears to be due to parental origin of individual mice in our cohort since even though all mice studied were confirmed to be APP$^{V717F+/+}$, high levels of Aβ deposition was observed only in mice derived from 4/8 breeding pairs (High pathology litters). Mice derived from the other 4 breeding pairs were virtually free of Aβ deposits (Low pathology litters). Using parental origin as a co-variate, there was a strong, significant effect of Mab 266 in reducing Aβ deposition (p=0.0082).

PEG-Anti-Aβ Antibody Fragment

Purification of Murine 266 and Humanized 1A1 Fab Analogs

Murine monoclonal antibody designated "266" (m266) was originally prepared by immunization with a peptide composed of residues 13-28 of human Aβ peptide and a Fab fragment of the m266 is designated (m266-Fab). The antibody is confirmed to immunoreact with this peptide. The preparation of m266 has been described previously (see for example, U.S. Pat. Nos. 8,066,999 and 7,195,761). To covalently attach a PEG molecule to m266-Fab, the Fab may be mutated to introduce a cysteine residue in CDR2 (N56C) of the heavy chain variable and PEGylated in a manner shown below (In Vitro PEGylation and Characterization). As the examples here describe experiments conducted in murine systems, the use of murine monoclonal antibodies and antibody fragments is satisfactory. However, in the treatment methods of the invention intended for human use, humanized forms of the antibodies and antibody fragments of the present invention are preferred. Anti-Aβ antibody fragment, 1A1-Fab, referred to in the examples below is a humanized antibody Fab fragment that comprises LCVR of SEQ ID NO.53 and HCVR of SEQ ID NO.54.

Culture supernatants from cells transfected with m266-Fab or humanized 1A1 Fab and analogs are purified using a two-step chromatography strategy consisting of cation exchange chromatography followed by size-exclusion chromatography using Superdex 75 resin (GE Healthcare). Following harvest, culture supernatant is concentrated using TFF and dialyzed against a 20-fold excess volume of 10 mM sodium acetate pH5 overnight at 4° C. Precipitate is removed by centrifugation and supernatant is loaded over a packed bed of SP sepharose (GE Healthcare) charged with 10 mM sodium acetate pH5. The column is washed with 10 mM sodium acetate pH5 containing successively larger amounts of NaCl until the Fab fragment eluted, at approximately 90 to 110 mM NaCl. Column fractions containing active Fab are identified and pooled. The volume is reduced and buffer exchanged (PBS) using a centrifugal concentration device (Millipore). The final volume is adjusted to 13 ml and loaded over a Superdex 75 sizing column. Fab containing fractions eluting at approximately 50 kD are identified and pooled for further characterization and PEGylation.

In Vitro PEGylation and Characterization

N56C Cysteine on 1A1-Fab purified from cell culture is blocked for PEGylation. Pierce's Reduce-Imm™ Immobilized Reductant beads are used to selectively reduce N56C Cysteine. Reductant beads are extracted from the column provided by the manufacturer and used in a batch mode. ~4 ml of beads are first activated with 8 ml 10 mM DTT in Reduce-IMM Equilibration buffer #1 (sodium phosphate+ EDTA, pH 8.0) for 30 mins The beads are then washed 3 times with PBS. 18 ml of 1A1 N56C Fab at 1.7 mg/ml in PBS pH 7.4 are added to the beads and 10 mM EDTA is added to the mixture. The mixture is rotated and incubated at room temperature for 4-5 hours. Fab is separated from the beads using Handee™ resin separators and the beads are washed with PBS. Fab and washes are combined, and reacted with 5 fold molar excess PEG-maleimide (20 kPEG from NOF; 10 kPEG from Sunbio; SkPEG from Nektar) for one hour. Reaction mixture is dialyzed against 4 L 10 mM sodium acetate buffer pH 5.0 so that the Fab and Fab-PEG can be captured on a SP sepharose column that is equilibrated with 10 mM sodium acetate buffer pH 5.0. Non-reacted Fab and Fab-PEG are eluted with a salt gradient. They are eluted between 50 mM to 70 mM NaCl. The protein is further purified by size exclusion chromatography (Superdex75 column, GE Healthcare) with PBS as the mobile phase. The reduction reaction can be scaled up and down. Similar methods can be used to prepare PEGylated murine 266 Fab N56C.

Samples are analyzed with size exclusion chromatography to confirm the addition of PEG to the Fab. Size exclusion chromatography is performed with TSK G3000PW XL (Tosoh Bioscience) column. The column is run at 0.5 ml/min with PBS plus 0.35 M NaCl at pH 7.4 using an Agilent HP1100 series analytical HPLC operating at 214 nm. In addition, samples are analyzed with SDS-PAGE. 10 μg of purified material is loaded on a 4-12% NuPage® Bis-Tris Gel and stained with SimplyBlue™ SafeStain.

1A1-Fab PEG Subcutaneous PK/PD Studies in PDAPP Mice

Studies are performed in young (3-month-old) transgenic PDAPP mice in order to investigate the pharmacokinetic/pharmacodynamic plasma response of antibody fragment and antibody fragment-Aβ complex. Several antibody fragment are investigated including: humanized 1A1-Fab; 1A1-Fab+SKD PEG; 1A1-Fab+10 KD PEG; and 1A1-Fab+20 KD PEG.

PDAPP+/− mice are injected subcutaneously with 1 mg/kg of respective antibody fragment and plasma is subsequently isolated at different time points depending upon antibody fragment injection group. The following time points are used for the various injection groups:

1A1-Fab are bled at 1, 4, 8, 12, 18, 24, and 48 hours post dose

1A1-Fab+5 KD PEG are bled at 1, 4, 8, 24, 48, 96, and 168 hours post dose

1A1-Fab+10 KD PEG are bled at 1, 4, 8, 24, 48, 96, and 168 hours post dose

1A1-Fab+20 KD PEG are bled at 1, 8, 24, 48, 96, 168, and 240 hours post dose

A total of five animals are analyzed per injection group per time point. The resulting plasma samples are aliquoted and stored at −80-degrees.

A. Methodology for Fab PK Analysis

Plasma 1A1 Fab concentrations for 1A1 Fab are determined using a sandwich ELISA. Plates are coated with goat anti-human IgG Kappa standards, control samples, and study samples are added to the plates then incubated for one hour at room temperature. A goat anti human IgG is used for detection followed by OPD for a colorimetric response. Plates are read at an absorbance of A493 with a reference of A700.

Concentrations from plasma samples are determined from standard curves prepared with known amounts of 1A1 Fab in mouse plasma using a 4/5-parameter algorithm; the range for the Fab and Fab-5K PEG assay is 0.003 to 0.3 μg/mL; the ranges for the Fab-10K PEG assays are 0.006 to 0.2 and 0.04 to 0.4 μg/mL; the ranges for the Fab 20K PEG assays are 0.02-0.4 and 0.04-0.4 μg/mL. Results demonstrate that addition of a PEG molecule and increasing the size of the PEG molecule increases the retention of the Pegylated Fabs in the plasma (77 ng/ml after 96 hours for 20K Pegylated 1A1 Fab) as compared to the non Pegylated 1A1 Fab (not detectable after 24 hours).

B. 1A1 Aβ ELISA Assay

The ELISA is essentially the same as described above for m266. Samples are prepared by diluting plasma into the sample diluents to yield the following: 20% plasma, 0.5 M guanidine, 5 mM Tris pH 8.0, 0.5× protease inhibitor cocktail, 20 μg/ml 1A1, and PBS. The Aβ peptides being measured in these assays are full length Aβ1-40 or Aβ1-42.

The colorimetric progression is monitored at 650 nm at 15, 30, and 60 minutes. Results are presented in Table 6 below.

TABLE 6

Pharmacodynamic Results:
Avg. Plasma Concentration for Aβ 40 (pg/ml)

| Time (h) | 1A1 Fab | 1A1 Fab + 5 KD PEG | 1A1 Fab + 10 KD PEG | 1A1 Fab + 20 KD PEG |
|---|---|---|---|---|
| 1 | 136.8 | 117.1 | 116.3 | 111.2 |
| 4 | 153.6 | 208.2 | 281.6 | |
| 8 | 96.65 | 198.4 | 406.3 | 529.2 |
| 12 | 131.9 | | | |
| 18 | 105.9 | | | |
| 24 | 114.7 | 133.6 | 585.1 | 1243 |
| 48 | 106.8 | 95.12 | 170.7 | 642 |
| 96 | | 88.48 | 113.7 | 177.9 |
| 168 | | 93.96 | 110.8 | 125.4 |
| 240 | | | | 200 |

The data from Table 6 demonstrates that humanized Fabs that are covalently attached to a PEG molecule provide an ideal PK/PD profile allowing for a flexible dosing schedule while preventing the antibody fragment-antigen complex from accumulating in plasma circulation for extended amounts of time.

Measuring Equilibrium Constants with KinExA

KinExA analysis is used as an orthogonal approach to measure binding affinity through equilibrium binding analysis due to the slow off-rate of the antigen Fab complex. A KinExA 3000 instrument (Sapidyne Inst. Inc.) is used to measure binding kinetics. Briefly, the antigen is covalently coupled to sepharose beads and the binding of free Fab/Fab-PEG to the beads is detected on the instrument. To measure Kd, individual tubes containing Fab/Fab-PEG (20 pM or 500 pM for 1A1-Fab-20kPEG, 5 pM or 50 pM for 1A1 Fab) with decreasing serially diluted antigen human soluble Abeta (1-40) (0-10 nM), are incubated for 30-50 hrs at 37° C. in PBS containing 1 mg/ml BSA to ensure equilibrium achievement. After the incubation, free Fab/Fab-PEG in each equilibrated sample is determined on the KinExA 3000 according to the manufacturer's instructions. $K_d$ values are determined by n-Curve Analysis using KinExA 3000 software. The results demonstrate that 1A1 Fab binds tightly to human Aβ (19 pM), with affinity ~10-fold higher compared to the m266 Fab (240 pM). In addition, covalent attachment of 20K PEG at N56C site has no impact on the affinity of 1A1-Fab (12 pM).

Amyloid Precursor Protein (APP) Binding Analysis Using Cell-based ELISA

To assess cross reactivity of 266 Fabs/mAbs with Abeta precursor APP, HEK 293 cells stably expressing APP (aa 1-751) are used. These cells are created by cloning the APP (1-751) gene into a plasmid containing the neomycin resistance marker. The recombinant plasmid is transfected into HEK 293 and cells are selected in 200 μg/ml G418 to generate an over-expressing stable cell line. For binding assays, 75,000 APP 751 cells are plated in each well of a PDL coated 96-well plate. Following incubation for 2 days in growth media (DMEM F12, 5% FBS, 10 mM Hepes pH7.5, 200 μg/ml G418), liquid is removed and 20 μg/ml of Fab or mAb is added in PBS (with Ca/Mg) containing 10 mg/ml BSA. Binding proceeds for 2 hours at 4 C and cells are washed 3× with 10 mg/ml BSA. A secondary antibody (horseradish peroxidase (hrp) conjugated anti kappa light chain) specific to human or mouse light chain is added in PBS/BSA (Southern Biotech). A dilution of 1:5000 in PBS/BSA is used for anti-human light chain and 1:2000 for anti-mouse light chain. Following one-hour incubation at 4 C, the cells are washed 5× with BSA/PBS. Hrp activity, as a function of Fab/mAb binding to APP, is measured by adding the substrate TMB for 10 minutes. The reactions are transferred to a clear 96-well plate and absorbance at 650 nm is measured. Data indicate that the Pegylated (5 kD, 10 kD), and 20 kD) 1A1-Fab and m266-Fab confer selectivity for Abeta peptide over APP.

Exemplified Anti-N3pGlu Aβ Antibody and Anti-Tau Antibody Combination

In Vivo Murine Combination Study

The following Example demonstrates how a study could be designed to verify (in animal models) that the combination of the anti-N3pGlu Abeta antibodies of the present invention, in combination with the anti-Tau antibodies of the present invention, may be useful for treating a disease characterized by deposition of Aβ and aberrant tau aggregation, such as AD. It should be understood however, that the following descriptions are set forth by way of illustration and not limitation, and that various modifications may be made by one of ordinary skill in the art.

In order to evaluate the Abeta plaque lowering of an anti-N3pGlu Abeta antibody such as hE8L, Antibody I or Antibody II, and the tau aggregation propagation neutralization of exemplified anti-Tau antibody, in a combination therapy as described herein, tau/APP murine progeny are generated through crossing of tau transgenic mice (for example, JNPL3 or Tg4510) with an APP transgenic mouse line (e.g., Tg2576 or PDAPP or APP knock-in). Tau/APP transgenic mice, as described above, have shown amyloid deposition may accelerate the spread of tau pathology. Tau/APP transgenic mice may be divided into treatment groups consisting of: (a) control antibody (30 mg/kg); (b) anti-N3pGlu Abeta antibody (15 mg/kg) and control antibody (15 mg/kg); (c) anti-Tau antibody (15 mg/kg) and control antibody (15 mg/kg); and (d) anti-N3pGlu Abeta antibody (15 mg/kg) and anti-Tau antibody (15 mg/kg).

Following the treatment period, mice may be sacrificed and brain and spinal cord tissue collected. Tau aggregate pathology and amyloid plaque pathology may be assessed as described above. To assess, Aβ reductions, parenchymal Aβ concentrations are determined in guanidine solubilized tissue homogenates by sandwich ELISA. Tissue extraction is performed with the bead beater technology wherein frozen tissue is extracted in 1 ml of 5.5 M guanidine/50 mM Tris/0.5× protease inhibitor cocktail at pH 8.0 in 2 ml deep well dishes containing 1 ml of siliconized glass beads (sealed plates were shaken for two intervals of 3-minutes each). The resulting tissue lysates are analyzed by sandwich ELISA for Abeta$_{1-40}$ and Abeta$_{1-42}$: bead beater samples are diluted 1:10 in 2% BSA/PBS-T and filtered through sample filter plates (Millipore). Samples, blanks, standards, quality control samples, are further diluted in 0.55 M guanidine/5 mM Tris in 2% BSA/PBST prior to loading the sample plates. Reference standard are diluted in sample diluent. Plates coated with the capture antibody 21F12 (anti-Abeta$_{42}$) or 2G3 (anti-Abeta$_{40}$) at 15 μg/ml are incubated with samples and detection is accomplished with biotinylated 3D6 (anti-Abeta$_{1-x}$) diluted in 2% BSA/PBS-T, followed by 1:20 K dilution NeutrAvidin-HRP (Pierce) in 2% BSA/PBS-T and color development with TMB (Pierce). The Aβ levels are interpolated from standard curves and the final tissue concentration is calculated as nanograms of Aβ per milligram of tissue wet weight. The percent area of the hippocampus and cortex occupied by deposited Aβ may be determined histologically. Cryostat serial coronal sections (7 to 10 μm thick) are incubated with 10 μg/ml of biotinylated 3D6 (anti-Abeta$_{1-x}$) or negative control murine IgG (biotinylated). Secondary HRP reagents specific for biotin are employed and the deposited Aβ visualized with DAB-Plus (DAKO). Immunoreactive Aβ deposits are quantified in defined areas of interest within the hippocampus or cortex by analyzing captured images with Image Pro plus software (Media Cybernetics). This study may show that the combination therapy of an anti-N3pGlu Abeta antibody and an anti-Tau antibody may result in a combination of both Aβ reduction and reduction in tau aggregate propagation.

In Vivo Combination Study

The following Example demonstrates how a study could be designed to verify that the combination of the anti-N3pGlu Abeta antibodies of the present invention, in combination with the anti-Tau antibodies of the present invention, may be useful for treating a disease characterized by deposition of Aβ and aberrant tau aggregation, such as AD. It should be understood however, that the following descriptions are set forth by way of illustration and not limitation, and that various modifications may be made by one of ordinary skill in the art.

In order to evaluate the Abeta plaque lowering of an anti-N3pGlu Abeta antibody such as hE8L, Antibody I or Antibody II, and the tau aggregation propagation neutralization of exemplified anti-Tau antibody, in a combination therapy as described herein, delay in disease progression may be assessed by biomarkers and/or cognitive and functional decline assessment using validated rating scales.

Patients may be divided into treatment groups consisting of double-blinded placebo and combination therapy groups. Combination therapy groups are administered an effective amount of an anti-N3pGlu Abeta antibody (an effective amount of anti-N3pGlu antibody may be determined based on achievement of significant amyloid reduction by florbetapir PET imagining, e.g., 3-40 mg/kg IV), in combination with an effective amount of an anti-Tau antibody (an effective amount of anti-Tau antibody may be determined based on achievement of slowing of progression of tau NFTs by tau PET imagine, e.g., 200-2800 mg IV). Monotherapy groupings (monotherapy group of anti-N3pGlu Abeta antibody at the same dosage as the anti-N3pGlu Abeta antibody in the combination therapy group; and monotherapy group of anti-Tau antibody at the same dosage as the anti-Tau antibody in the combination therapy group) may be included to further elucidate the contributions of each individual antibody to the disease modification. Moreover, treatment groups may be characterized based on a diagnosis of preclinical or clinical AD, or based on a diagnosis that the patient (although asymptomatic for AD) possesses an AD disease-causing genetic mutation. For example, groups may include one or more of: (a) asymptomatic but AD-causing genetic-mutation positive; (b) preclinical AD; (c) prodromal AD; (d) mild AD; (e) moderate AD; and (f) severe AD. Each treatment group may receive the respective treatment once per month for a treatment period of 3 months to 24 months (and may receive the respective treatments for different time periods, e.g., 3-6 month treatment period for N3PGlu Abeta antibody and 24 month treatment period for anti-tau antibody).

Following the treatment period, AD neurodegeneration may be assessed through one or more of the following biomarker assessments: (a) Tau PET imagining (assessment of NFT accumulation); (b) volumetric MRI (assessment of neuroanatomical atrophy); (c) FDG-PEG PET imagining (assessment of hypometabolism); (d) florbetapir perfusion PET imagining (assessment of hypometabolism); (e) CSF tau concentration (assessment of neurodegeneration); (f) CSF phosphorylated-Tau concentration (assessment of neurodegeneration); (g) CSF neurofilament light chain concentration (assessment of neurodegeneration); (h) CSF neurogranin concentration (assessment of neurodegeneration); and (i) florbetapir PET imagining (assessment of amyloid plaque pathology). Additionally, one or more validated rating scales assessing the cognitive and functional decline of each treatment group may be applied, for example ADAS-cog, MMSE, CDR-SB, ADCS-ADL, and Functional Activities Questionnaire (FAQ). This study may show that the combination therapy of an anti-N3pGlu Abeta antibody of the present invention and an anti-Tau antibody of the present invention may result in a combination of both Abeta reductions, and reduction in tau aggregate propagation.

Exemplified Anti-Aβ Antibody and Anti-Tau Antibody Combination

In Vivo Murine Combination Study

The following Example demonstrates how a study could be designed to verify (in animal models) that the combination of the anti-Aβ antibodies of the present invention, in combination with the anti-Tau antibodies of the present invention, may be useful for treating a disease characterized by formation of amyloid plaques and aberrant tau aggregation, such as AD. It should be understood however, that the following descriptions are set forth by way of illustration and not limitation, and that various modifications may be made by one of ordinary skill in the art.

In order to evaluate the impact of sequestration of Aβ by exemplified anti-Aβ antibody, and the tau aggregation propagation neutralization of exemplified anti-Tau antibody, in a combination therapy as described herein, tau/APP murine progeny are generated through crossing of tau transgenic mice (for example, JNPL3 or Tg4510) with an APP transgenic mouse line (e.g., Tg2576 or PDAPP or APP knock-in). Tau/APP transgenic mice, as described above, have shown amyloid deposition may accelerate the spread of tau pathology. Tau/APP transgenic mice may be divided into treatment groups consisting of: (a) control antibody (30 mg/kg); (b) anti-Aβ antibody (15 mg/kg) and control antibody (15 mg/kg); (c) anti-Tau antibody (15 mg/kg) and control antibody (15 mg/kg); and (d) anti-Aβ antibody (15 mg/kg) and anti-Tau antibody (15 mg/kg).

Following the treatment period, mice may be sacrificed and brain and spinal cord tissue collected. Tau aggregate pathology and amyloid plaque pathology may be assessed as described above. Free plasma Aβ levels may be assessed as described above. To assess Aβ reductions, parenchymal Aβ concentrations are determined in guanidine solubilized tissue homogenates by sandwich ELISA. Tissue extraction is performed with the bead beater technology wherein frozen tissue is extracted in 1 ml of 5.5 M guanidine/50 mM Tris/0.5× protease inhibitor cocktail at pH 8.0 in 2 ml deep well dishes containing 1 ml of siliconized glass beads (sealed plates were shaken for two intervals of 3-minutes each). The resulting tissue lysates are analyzed by sandwich ELISA for Abeta$_{1-40}$ and Abeta$_{1-42}$: bead beater samples are diluted 1:10 in 2% BSA/PBS-T and filtered through sample filter plates (Millipore). Samples, blanks, standards, quality control samples, are further diluted in 0.55 M guanidine/5 mM Tris in 2% BSA/PBST prior to loading the sample plates. Reference standard are diluted in sample diluent. Plates coated with the capture antibody 21F12 (anti-Abeta$_{42}$) or 2G3 (anti-Abeta$_{40}$) at 15 μg/ml are incubated with samples and detection is accomplished with biotinylated 3D6 (anti-Abeta$_{1-x}$) diluted in 2% BSA/PBS-T, followed by 1:20 K dilution NeutrAvidin-HRP (Pierce) in 2% BSA/PBS-T and color development with TMB (Pierce).

The Aβ levels are interpolated from standard curves and the final tissue concentration is calculated as nanograms of Aβ per milligram of tissue wet weight. The percent area of the hippocampus and cortex occupied by deposited Aβ may be determined histologically. Cryostat serial coronal sections (7 to 10 μm thick) are incubated with 10 μg/ml of biotinylated 3D6 (anti-Abeta$_{1-x}$) or negative control murine IgG (biotinylated). Secondary HRP reagents specific for biotin are employed and the deposited Aβ visualized with DAB-Plus (DAKO). Immunoreactive Aβ deposits are quantified in defined areas of interest within the hippocampus or cortex by analyzing captured images with Image Pro plus software (Media Cybernetics). This study may show that the combination therapy of an anti-Aβ antibody and an anti-Tau antibody may result in a combination of a reduction in free Aβ levels, amyloid plaque reduction and reduction in tau aggregate propagation.

In Vivo Combination Study

The following Example demonstrates how a study could be designed to verify that the combination of the anti-Aβ antibodies of the present invention, in combination with the anti-Tau antibodies of the present invention, may be useful for treating a disease characterized by formation of amyloid plaques and aberrant tau aggregation, such as AD. It should be understood however, that the following descriptions are set forth by way of illustration and not limitation, and that various modifications may be made by one of ordinary skill in the art.

In order to evaluate the impact of sequestration of Aβ of exemplified anti-Aβ antibody, and the tau aggregation propagation neutralization of exemplified anti-Tau antibody, in a combination therapy as described herein, delay in disease progression may be assessed by biomarkers and/or cognitive and functional decline assessment using validated rating scales.

Patients may be divided into treatment groups consisting of double-blinded placebo and combination therapy groups. Combination therapy groups are administered an effective amount of an anti-Aβ antibody (an effective amount of anti-Aβ antibody may be determined, for example, based on achievement of significant reduction of modeled free plasma Aβ, e.g., 3-40 mg/kg IV), in combination with an effective amount of an anti-Tau antibody (an effective amount of anti-Tau antibody may be determined, for example, based on achievement of slowing of progression of tau NFTs by tau PET imagine, e.g., 200-2800 mg IV). Monotherapy groupings (monotherapy group of anti-Aβ antibody at the same dosage as the anti-Aβ antibody in the combination therapy group; and monotherapy group of anti-Tau antibody at the same dosage as the anti-Tau antibody in the combination therapy group) may be included to further elucidate the contributions of each individual antibody to the disease modification. Moreover, treatment groups may be characterized based on a diagnosis of pre-clinical or clinical AD, or based on a diagnosis that the patient (although asymptomatic for AD) possesses an AD disease-causing genetic mutation. For example, groups may include one or more of: (a) asymptomatic but AD-causing genetic-mutation positive; (b) preclinical AD; (c) prodromal AD; (d) mild AD; (e) moderate AD; and (f) severe AD. Each treatment group may receive the respective treatment once per month for a treatment period of 3 months to 24 months (and may receive the respective treatments for different time periods, e.g., 3-6 month treatment period for anti-Aβ antibody and 24 month treatment period for anti-tau antibody).

Following the treatment period, AD neurodegeneration may be assessed through one or more of the following biomarker assessments: (a) Tau PET imagining (assessment of NFT accumulation); (b) volumetric MRI (assessment of neuroanatomical atrophy); (c) FDG-PEG PET imagining (assessment of hypometabolism); (d) florbetapir perfusion PET imagining (assessment of hypometabolism); (e) CSF tau concentration (assessment of neurodegeneration); (f) CSF phosphorylated-Tau concentration (assessment of neurodegeneration); (g) CSF neurofilament light chain concentration (assessment of neurodegeneration); (h) CSF neurogranin concentration (assessment of neurodegeneration); and (i) florbetapir PET imagining (assessment of amyloid plaque pathology). Additionally, one or more validated rating scales assessing the cognitive and functional decline of each treatment group may be applied, for example ADAS-cog, MMSE, CDR-SB, ADCS-ADL, and Functional Activities Questionnaire (FAQ).

This study may show that the combination therapy of an anti-Aβ antibody of the present invention and an anti-Tau antibody of the present invention may result in a combination of both reduced free plasma and CSF Aβ, and a reduction in tau aggregate propagation.

Exemplified PEG-Anti-Aβ Antibody Fragment and Anti-Tau Antibody Combination

In Vivo Murine Combination Study

The following Example demonstrates how a study could be designed to verify (in animal models) that the combination of the PEG-anti-Aβ antibody fragments of the present invention, in combination with the anti-Tau antibodies of the present invention, may be useful for treating a disease characterized by formation of amyloid plaques and aberrant tau aggregation, such as AD. It should be understood however, that the following descriptions are set forth by way of illustration and not limitation, and that various modifications may be made by one of ordinary skill in the art.

In order to evaluate the impact of plasma Aβ reduction by exemplified PEG-anti-Aβ antibody fragments, and the tau aggregation propagation neutralization of exemplified anti-Tau antibody, in a combination therapy as described herein, tau/APP murine progeny are generated through crossing of tau transgenic mice (for example, JNPL3 or Tg4510) with an APP transgenic mouse line (e.g., Tg2576 or PDAPP or APP knock-in). Tau/APP transgenic mice, as described above, have shown amyloid deposition may accelerate the spread of tau pathology. Tau/APP transgenic mice may be divided into treatment groups consisting of: (a) control antibody (30 mg/kg); (b) PEG-anti-Aβ antibody fragments (15 mg/kg) and control antibody (15 mg/kg); (c) anti-Tau antibody (15 mg/kg) and control antibody (15 mg/kg); and (d) PEG-anti-Aβ antibody fragments (15 mg/kg) and anti-Tau antibody (15 mg/kg).

Following the treatment period, mice may be sacrificed and brain and spinal cord tissue collected. Tau aggregate pathology may be assessed as described above. Plasma Aβ levels may be assessed as described above (and as previously described, for example, in U.S. Pat. No. 7,195,761). To assess Aβ reductions, parenchymal Aβ concentrations are determined in guanidine solubilized tissue homogenates by sandwich ELISA. Tissue extraction is performed with the bead beater technology wherein frozen tissue is extracted in 1 ml of 5.5 M guanidine/50 mM Tris/0.5× protease inhibitor cocktail at pH 8.0 in 2 ml deep well dishes containing 1 ml of siliconized glass beads (sealed plates were shaken for two intervals of 3-minutes each). The resulting tissue lysates are analyzed by sandwich ELISA for Abeta$_{1-40}$ and Abeta$_{1-42}$: bead beater samples are diluted 1:10 in 2% BSA/PBS-T and filtered through sample filter plates (Millipore). Samples, blanks, standards, quality control samples, are further diluted in 0.55 M guanidine/5 mM Tris in 2% BSA/PBST prior to loading the sample plates. Reference standard are diluted in sample diluent. Plates coated with the capture antibody 21F12 (anti-Abeta$_{42}$) or 2G3 (anti-Abeta$_{40}$) at 15 µg/ml are incubated with samples and detection is accomplished with biotinylated 3D6 (anti-Abeta$_{1-x}$) diluted in 2% BSA/PBS-T, followed by 1:20 K dilution NeutrAvidin-HRP (Pierce) in 2% BSA/PBS-T and color development with TMB (Pierce). The Aβ levels are interpolated from standard curves and the final tissue concentration is calculated as nanograms of Aβ per milligram of tissue wet weight. The percent area of the hippocampus and cortex occupied by deposited Aβ may be determined histologically. Cryostat serial coronal sections (7 to 10 µm thick) are incubated with 10 µg/ml of biotinylated 3D6 (anti-Abeta$_{1-x}$) or negative control murine IgG (biotinylated). Secondary HRP reagents specific for biotin are employed and the deposited Aβ visualized with DAB-Plus (DAKO). Immunoreactive Aβ deposits are quantified in defined areas of interest within the hippocampus or cortex by analyzing captured images with Image Pro plus software (Media Cybernetics). This study may show that the combination therapy of a PEG-anti-Aβ antibody fragment and an anti-Tau antibody may result in a combination of a reduction in Aβ levels, amyloid plaque reduction and reduction in tau aggregate propagation.

In Vivo Combination Study

The following Example demonstrates how a study could be designed to verify that the combination of the PEG-anti-Aβ antibody fragment of the present invention, in combination with the anti-Tau antibodies of the present invention, may be useful for treating a disease characterized by formation of amyloid plaques and aberrant tau aggregation, such as AD. It should be understood however, that the following descriptions are set forth by way of illustration and not limitation, and that various modifications may be made by one of ordinary skill in the art.

In order to evaluate the impact of plasma Aβ reduction of exemplified PEG-anti-Aβ antibody fragment, and the tau aggregation propagation neutralization of exemplified anti-Tau antibody, in a combination therapy as described herein, delay in disease progression may be assessed by biomarkers and/or cognitive and functional decline assessment using validated rating scales.

Patients may be divided into treatment groups consisting of double-blinded placebo and combination therapy groups. Combination therapy groups are administered an effective amount of an PEG-anti-Aβ antibody fragment (an effective amount of PEG-anti-Aβ antibody fragment may be determined, for example, based on achievement of significant reduction of modeled free plasma Aβ, e.g., 25-200 mg subcutaneous per week), in combination with an effective amount of an anti-Tau antibody (an effective amount of anti-Tau antibody may be determined, for example, based on achievement of slowing of progression of tau NFTs by tau PET imagine, e.g., 200-2800 mg IV). Monotherapy groupings (monotherapy group of PEG-anti-Aβ antibody fragment at the same dosage as the PEG-anti-Aβ antibody fragment in the combination therapy group; and monotherapy group of anti-Tau antibody at the same dosage as the anti-Tau antibody in the combination therapy group) may be included to further elucidate the contributions of each individual antibody to the disease modification. Moreover, treatment groups may be characterized based on a diagnosis of pre-clinical or clinical AD, or based on a diagnosis that the patient (although asymptomatic for AD) possesses an AD disease-causing genetic mutation. For example, groups may include one or more of: (a) asymptomatic but AD-causing genetic-mutation positive; (b) preclinical AD; (c) prodromal AD; (d) mild AD; (e) moderate AD; and (f) severe AD. Each treatment group may receive the respective treatment once per month for a treatment period of 3 months to 24 months (and may receive the respective treatments for different time periods, e.g., 3-6 month treatment period for PEG-anti-Aβ antibody fragment and 24 month treatment period for anti-tau antibody).

Following the treatment period, AD neurodegeneration may be assessed through one or more of the following biomarker assessments: (a) Tau PET imagining (assessment of NFT accumulation); (b) volumetric MRI (assessment of neuroanatomical atrophy); (c) FDG-PEG PET imagining (assessment of hypometabolism); (d) florbetapir perfusion PET imagining (assessment of hypometabolism); (e) CSF tau concentration (assessment of neurodegeneration); (f) CSF phosphorylated-Tau concentration (assessment of neurodegeneration); (g) CSF neurofilament light chain concentration (assessment of neurodegeneration); (h) CSF neurogranin concentration (assessment of neurodegeneration); and (i) florbetapir PET imagining (assessment of amyloid plaque pathology). Additionally, one or more validated rating scales assessing the cognitive and functional decline of each treatment group may be applied, for example ADAS-cog, MMSE, CDR-SB, ADCS-ADL, and Functional Activities Questionnaire (FAQ).

This study may show that the combination therapy of a PEG anti-Aβ antibody fragment of the present invention and an anti-Tau antibody of the present invention may result in a combination of both reduced plasma and CSF Aβ, and a reduction in tau aggregate propagation.

Sequences

SEQ ID NO. 1-HCDR1-anti-N3pGlu Antibody (Antibody I and Antibody II)
KASGYTFTDYYIN SEQ ID NO. 2-HCDR2-anti-N3pGlu Antibody (Antibody I and Antibody II)
WINPGSGNTKYNEKFKG SEQ ID NO. 3-HCDR3-anti-N3pGlu Antibody (Antibody I and Antibody II)
TREGETVY SEQ ID NO. 4-LCDR1-anti-N3pGlu Antibody (Antibody I and Antibody II)
KSSQSLLYSRGKTYLN SEQ ID NO. 5-LCDR2-anti-N3pGlu Antibody (Antibody II)
YAVSKLDS SEQ ID NO. 6-LCDR2-anti-N3pGlu Antibody (Antibody I)
YDVSKLDS

| Sequences |
|---|
| SEQ ID NO. 7-LCDR3-anti-N3pGlu Antibody (Antibody I and Antibody II)<br>VQGTHYPFT<br><br>SEQ ID NO. 8-HCVR-anti-N3pGlu Antibody (Antibody I and Antibody II)<br>QVQLVQSGAEVKKPGSSVKVSCKASGYTFTDYYINWVRQAPGQGLEWMGWINP<br>GSGNTKYNEKFKGRVTITADESTSTAYMELSSLRSEDTAVYYCTREGETVYWGQ<br>GTLVTVSS<br><br>SEQ ID NO. 9-LCVR-anti-N3pGlu Antibody (Antibody I)<br>DVVMTQSPLSLPVTLGQPASISCKSSQSLLYSRGKTYLNWFQQRPGQSPRRLIYD<br>VSKLDSGVPDRFSGSGSGTDFTLKISRVEAEDVGVYYCVQGTHYPFTFGQGTKLE<br>IK<br><br>SEQ ID NO. 10-LCVR-anti-N3pGlu Antibody (Antibody II)<br>DIQMTQSPSTLSASVGDRVTITCKSSQSLLYSRGKTYLNWLQQKPGKAPKLLIYA<br>VSKLDSGVPSRFSGSGSGTEFTLTISSLQPDDFATYYCVQGTHYPFTFGQGTKLEI<br>K<br><br>SEQ ID NO. 11-HC-anti-N3pGlu Antibody (Antibody I and Antibody II)<br>QVQLVQSGAEVKKPGSSVKVSCKASGYTFTDYYINWVRQAPGQGLEWMGWINP<br>GSGNTKYNEKFKGRVTITADESTSTAYMELSSLRSEDTAVYYCTREGETVYWGQ<br>GTLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKA<br>LPAPIEKTISKAKGQPREPQVYTLPPSRDELTKNQVSLTCLVKGFYPSDIAVEWES<br>NGQPENNYKTTPPVLDSDGSFFLYSKLTVDKSRWQQGNVFSCSVMHEALHNHY<br>TQKSLSLSPG<br><br>SEQ ID NO. 12-LC-anti-N3pGlu Antibody (Antibody I)<br>DVVMTQSPLSLPVTLGQPASISCKSSQSLLYSRGKTYLNWFQQRPGQSPRRLIYD<br>VSKLDSGVPDRFSGSGSGTDFTLKISRVEAEDVGVYYCVQGTHYPFTFGQGTKLE<br>IKRTVAAPSVFIFPPSDEQLKSGTASVVCLLNNFYPREAKVQWKVDNALQSGNSQ<br>ESVTEQDSKDSTYSLSSTLTLSKADYEKHKVYACEVTHQGLSSPVTKSFNRGEC<br><br>SEQ ID NO. 13-LC-anti-N3pGlu Antibody (Antibody II)<br>DIQMTQSPSTLSASVGDRVTITCKSSQSLLYSRGKTYLNWLQQKPGKAPKLLIYA<br>VSKLDSGVPSRFSGSGSGTEFTLTISSLQPDDFATYYCVQGTHYPFTFGQGTKLEI<br>KRTVAAPSVFIFPPSDEQLKSGTASVVCLLNNFYPREAKVQWKVDNALQSGNSQ<br>ESVTEQDSKDSTYSLSSTLTLSKADYEKHKVYACEVTHQGLSSPVTKSFNRGEC<br><br>SEQ ID NO. 14-Exemplified DNA for Expressing HC of SEQ ID NO. 11<br>CAGGTGCAGCTGGTGCAGTCTGGGGCTGAGGTGAAGAAGCCTGGGTCCTCGG<br>TGAAGGTCTCCTGCAAGGCTTCTGGATACACCTTCACCGACTATTATATCAAC<br>TGGGTGCGACAGGCCCCTGGACAAGGGCTTGAGTGGATGGGATGGATCAACC<br>CTGGCAGTGGTAATACAAAGTACAATGAGAAGTTCAAGGGCAGAGTCACGAT<br>TACCGCGGACGAATCCACGAGCACAGCCTACATGGAGCTGAGCAGCCTGAGA<br>TCTGAGGACACGGCCGTGTATTACTGTACAAGAGAAGGCGAGACGGTCTACT<br>GGGGCCAGGGAACCCTGGTCACCGTCTCCTCAGCCTCCACCAAGGGCCCATC<br>GGTCTTCCCGCTAGCACCCTCCTCCAAGAGCACCTCTGGGGGCACAGCGGCCC<br>TGGGCTGCCTGGTCAAGGACTACTTCCCCGAACCGGTGACGGTGTCGTGGAA<br>CTCAGGCGCCCTGACCAGCGGCGTGCACACCTTCCCGGCTGTCCTACAGTCCT<br>CAGGACTCTACTCCCTCAGCAGCGTGGTGACCGTGCCCTCCAGCAGCTTGGGC<br>ACCCAGACCTACATCTGCAACGTGAATCACAAGCCCAGCAACACCAAGGTGG<br>ACAAGAAAGTTGAGCCCAAATCTTGTGACAAAACTCACACATGCCCACCGTG<br>CCCAGCACCTGAACTCCTGGGGGGACCGTCAGTCTTCCTCTTCCCCCCAAAAC<br>CCAAGGACACCCTCATGATCTCCCGGACCCCTGAGGTCACATGCGTGGTGGT<br>GGACGTGAGCCACGAAGACCCTGAGGTCAAGTTCAACTGGTACGTGGACGGC<br>GTGGAGGTGCATAATGCCAAGACAAAGCCGCGGGAGGAGCAGTACAACAGC<br>ACGTACCGTGTGGTCAGCGTCCTCACCGTCCTGCACCAGGACTGGCTGAATGG<br>CAAGGAGTACAAGTGCAAGGTCTCCAACAAAGCCCTCCCAGCCCCCATCGAG<br>AAAACCATCTCCAAAGCCAAAGGGCAGCCCCGAGAACCACAGGTGTACACCC<br>TGCCCCCATCCCGGGACGAGCTGACCAAGAACCAGGTCAGCCTGACCTGCCT<br>GGTCAAAGGCTTCTATCCCAGCGACATCGCCGTGGAGTGGGAGAGCAATGGG<br>CAGCCGGAGAACAACTACAAGACCACGCCCCCCGTGCTGGACTCCGACGGCT<br>CCTTCTTCCTCTATAGCAAGCTCACCGTGGACAAGAGCAGGTGGCAGCAGGG<br>GAACGTCTTCTCATGCTCCGTGATGCATGAGGCTCTGCACAACCACTACACGC<br>AGAAGAGCCTCTCCCTGTCTCCGGGT<br><br>SEQ ID NO. 15-Exemplified DNA for Expressing LC of SEQ ID NO. 12<br>GATGTTGTGATGACTCAGTCTCCACTCTCCCTGCCCGTCACCCTTGGACAGCC<br>GGCCTCCATCTCCTGCAAGTCTAGTCAAAGCCTCCTGTACAGTCGCGGAAAAA<br>CCTACTTGAATTGGTTTCAGCAGAGGCCAGGCCAATCTCCAAGGCGCCTAATT<br>TATGATGTTTCTAAACTGGACTCTGGGGTCCCAGACAGATTCAGCGGCAGTGG<br>GTCAGGCACTGATTTCACACTGAAAATCAGCAGGGTGGAGGCTGAGGATGTT<br>GGGGTTTATTACTGCGTGCAAGGTACACACTACCCTTTCACTTTTGGCCAAGG |

| Sequences |
|---|
| GACCAAGCTGGAGATCAAACGGACCGTGGCTGCACCATCTGTCTTCATCTTCC<br>CGCCATCTGATGAGCAGTTGAAATCTGGAACTGCCTCTGTTGTGTGCCTGCTG<br>AATAACTTCTATCCCAGAGAGGCCAAAGTACAGTGGAAGGTGGATAACGCCC<br>TCCAATCGGGTAACTCCCAGGAGAGTGTCACAGAGCAGGACAGCAAGGACA<br>GCACCTACAGCCTCAGCAGCACCCTGACGCTGAGCAAAGCAGACTACGAGAA<br>ACACAAAGTCTACGCCTGCGAAGTCACCCATCAGGGCCTGAGCTCGCCCGTC<br>ACAAAGAGCTTCAACAGGGGAGAGTGC<br><br>SEQ ID NO. 16-Exemplified DNA for Expressing LC of SEQ ID NO. 13<br>GACATCCAGATGACCCAGTCTCCTTCCACCCTGTCTGCATCTGTAGGAGACAG<br>AGTCACCATCACTTGCAAGTCCAGTCAGAGTCTCCTGTACAGTCGCGGAAAA<br>ACCTATTTGAACTGGCTCCAGCAGAAACCAGGGAAAGCCCCTAAGCTCCTGA<br>TCTATGCTGTCTCCAAACTGGACAGTGGGGTCCCATCAAGGTTCAGCGGCAGT<br>GGATCTGGGACAGAATTCACTCTCACCATCAGCAGCCTGCAGCCTGATGATTT<br>TGCAACTTATTACTGCGTGCAGGGTACACATTATCCTTTCACTTTTGGCCAGG<br>GGACCAAGCTGGAGATCAAACGGACCGTGGCTGCACCATCTGTCTTCATCTTC<br>CCGCCATCTGATGAGCAGTTGAAATCTGGAACTGCCTCTGTTGTGTGCCTGCT<br>GAATAACTTCTATCCCAGAGAGGCCAAAGTACAGTGGAAGGTGGATAACGCC<br>CTCCAATCGGGTAACTCCCAGGAGAGTGTCACAGAGCAGGACAGCAAGGACA<br>GCACCTACAGCCTCAGCAGCACCCTGACGCTGAGCAAAGCAGACTACGAGAA<br>ACACAAAGTCTACGCCTGCGAAGTCACCCATCAGGGCCTGAGCTCGCCCGTC<br>ACAAAGAGCTTCAACAGGGGAGAGTGC<br><br>SEQ ID NO. 17-anti-N3pGlu Antibody (LCDR1-B12L/R17L/hE8L)<br>KSSQSLLYSRGKTYLN<br><br>SEQ ID NO. 18-anti-N3pGlu Antibody (LCDR2-B12L/R17L/hE8L)<br>AVSKLDS<br><br>SEQ ID NO. 19-anti-N3pGlu Antibody (LCDR3-B12L/R17L/hE8L)<br>VQGTHYPFT<br><br>SEQ ID NO. 20-anti-N3pGlu Antibody (HCDR1-B12L)<br>GYDFTRYYIN<br><br>SEQ ID NO. 21-anti-N3pGlu Antibody (HCDR1-R17L)<br>GYTFTRYYIN<br><br>SEQ ID NO. 22-anti-N3pGlu Antibody (HCDR2-B12L/R17L/hE8L)<br>WINPGSGNTKYNEKFKG<br><br>SEQ ID NO. 23-anti-N3pGlu Antibody (HCDR3-B12L)<br>EGITVY<br><br>SEQ ID NO. 24-anti-N3pGlu Antibody (HCDR3-R17L)<br>EGTTVY<br><br>SEQ ID NO. 25-anti-N3pGlu Antibody (LCVR-B12L/R17L)<br>DIVMTQTPLSLSVTPGQPASISC<u>KSSQSLLYSRGKTYLN</u>WLLQKPGQSPQLLIY<u>AV</u><br><u>SKLDS</u>GVPDRFSGSGSGTDFTLKISRVEAEDVGVYYC<u>VQGTHYPFT</u>FGQGTKLEI<br>K<br><br>SEQ ID NO. 26-anti-N3pGlu Antibody (HCVR-B12L)<br>QVQLVQSGAEVKKPGSSVKVSCKAS<u>GYDFTRYYIN</u>WVRQAPGQGLEWMG<u>WINP</u><br><u>GSGNTKYNEKFKG</u>RVTITADESTSTAYMELSSLRSEDTAVYYCAR<u>EGITVY</u>WGQ<br>GTTVTVSS<br><br>SEQ ID NO. 27-anti-N3pGlu Antibody (HCVR-R17L)<br>QVQLVQSGAEVKKPGSSVKVSCKAS<u>GYTFTRYYIN</u>WVRQAPGQGLEWMG<u>WINP</u><br><u>GSGNTKYNEKFKG</u>RVTITADESTSTAYMELSSLRSEDTAVYYCAR<u>EGTTVY</u>WGQ<br>GTTVTVSS<br><br>SEQ ID NO. 28-anti-N3pGlu Antibody (LC-B12L/R17L)<br>DIVMTQTPLSLSVTPGQPASISC<u>KSSQSLLYSRGKTYLN</u>WLLQKPGQSPQLLIY<u>AV</u><br><u>SKLDS</u>GVPDRFSGSGSGTDFTLKISRVEAEDVGVYYC<u>VQGTHYPFT</u>FGQGTKLEI<br>KRTVAAPSVFIFPPSDEQLKSGTASVVCLLNNFYPREAKVQWKVDNALQSGNSQ<br>ESVTEQDSKDSTYSLSSTLTLSKADYEKHKVYACEVTHQGLSSPVTKSFNRGEC<br><br>SEQ ID NO. 29-anti-N3pGlu Antibody (HC-B12L)<br>QVQLVQSGAEVKKPGSSVKVSCKAS<u>GYDFTRYYIN</u>WVRQAPGQGLEWMG<u>WINP</u><br><u>GSGNTKYNEKFKG</u>RVTITADESTSTAYMELSSLRSEDTAVYYCAR<u>EGITVY</u>WGQ<br>GTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKA |

| Sequences |
|---|
| LPAPIEKTISKAKGQPREPQVYTLPPSRDELTKNQVSLTCLVKGFYPSDIAVEWES<br>NGQPENNYKTTPPVLDSDGSFFLYSKLTVDKSRWQQGNVFSCSVMHEALHNHY<br>TQKSLSLSPG<br><br>SEQ ID NO. 30-anti-N3pGlu Antibody (HC-R17L)<br>QVQLVQSGAEVKKPGSSVKVSCKAS<u>GYTFTRYYIN</u>WVRQAPGQGLEWMG<u>WINP</u><br><u>GSGNTKYNEKFKG</u>RVTITADESTSTAYMELSSLRSEDTAVYYCAR<u>EGTTVY</u>WGQ<br>GTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKA<br>LPAPIEKTISKAKGQPREPQVYTLPPSRDELTKNQVSLTCLVKGFYPSDIAVEWES<br>NGQPENNYKTTPPVLDSDGSFFLYSKLTVDKSRWQQGNVFSCSVMHEALHNHY<br>TQKSLSLSPG<br><br>SEQ ID NO. 31-N3pGlu Aβ<br>[pE]FRHDSGYEVHHQKLVFFAEDVGSNKGAIIGLMVGGVVIA<br><br>SEQ ID NO. 32-anti-N3pGlu Antibody (LCVR-hE8L)<br>DIVMTQTPLSLSVTPGQPASISC<u>KSSQSLLYSRGKTYLN</u>WLLQKPGQSPQLLIY<u>AV</u><br><u>SKLDS</u>GVPDRFSGSGSGTDFTLKISRVEAEDVGVYYC<u>VQGTHYPFT</u>FGQGTKLEI<br>K<br><br>SEQ ID NO. 33-anti-N3pGlu Antibody (LC-hE8L)<br>DIVMTQTPLSLSVTPGQPASISC<u>KSSQSLLYSRGKTYLN</u>WLLQKPGQSPQLLIY<u>AV</u><br><u>SKLDS</u>GVPDRFSGSGSGTDFTLKISRVEAEDVGVYYC<u>VQGTHYPFT</u>FGQGTKLEI<br>KRTVAAPSVFIFPPSDEQLKSGTASVVCLLNNFYPREAKVQWKVDNALQSGNSQ<br>ESVTEQDSKDSTYSLSSTLTLSKADYEKHKVYACEVTHQGLSSPVTKSFNRGEC<br><br>SEQ ID NO. 34-anti-N3pGlu Antibody (HCVR-hE8L)<br>QVQLVQSGAEVKKPGSSVKVSCKAS<u>GYTFTDYYIN</u>WVRQAPGQGLEWMG<u>WINP</u><br><u>GSGNTKYNEKFKG</u>RVTITADESTSTAYMELSSLRSEDTAVYYCAR<u>EGETVY</u>WGQ<br>GTTVTVSS<br><br>SEQ ID NO. 35-anti-N3pGlu Antibody (HC-hE8L)<br>QVQLVQSGAEVKKPGSSVKVSCKAS<u>GYTFTDYYIN</u>WVRQAPGQGLEWMG<u>WINP</u><br><u>GSGNTKYNEKFKG</u>RVTITADESTSTAYMELSSLRSEDTAVYYCAR<u>EGETVY</u>WGQ<br>GTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKA<br>LPAPIEKTISKAKGQPREPQVYTLPPSRDELTKNQVSLTCLVKGFYPSDIAVEWES<br>NGQPENNYKTTPPVLDSDGSFFLYSKLTVDKSRWQQGNVFSCSVMHEALHNHY<br>TQKSLSLSPG<br><br>SEQ ID NO. 36-anti-N3pGlu Antibody (HCDR1-hE8L)<br>GYTFTDYYIN<br><br>SEQ ID NO. 37-anti-N3pGlu Antibody (HCDR3-hE8L)<br>EGETVY<br><br>SEQ ID NO. 38-Aβ 1-42<br>DAEFRHDSGYEVHHQKLVFFAEDVGSNKGAIIGLMVGGVVIA<br><br>SEQ ID NO. 39-LCDR1 of exemplified anti-Aβ antibody<br>RSSQSLIYSDGNAYLH<br><br>SEQ ID NO. 40-LCDR2 of exemplified anti-Aβ antibody<br>KVSNRFS<br><br>SEQ ID NO. 41-LCDR3 of exemplified anti-Aβ antibody<br>SQSTHVPWT<br><br>SEQ ID NO. 42-HCDR1 of exemplified anti-Aβ antibody<br>RYSMS<br><br>SEQ ID NO. 43-HCDR2 of exemplified anti-Aβ antibody<br>QINSVGNSTYYPDTVKG<br><br>SEQ ID NO. 44-HCDR3 of exemplified anti-Aβ antibody<br>GDY<br><br>SEQ ID NO. 45-LCVR of exemplified anti-Aβ antibody<br>DXaa$_2$VMTQXaa$_7$PLSLPVXaa$_{14}$Xaa$_{15}$GQPASISCRSSQSLXaa$_{30}$YSDGNAYLHWFLQ<br>KPGQSPXaa$_{50}$LLIYKVSNRFSGVPDRFSGSGSGTDFTLKISRVEAEDXaa$_{88}$GVYYCS<br>QSTHVPWTFGXaa$_{105}$GTXaa$_{108}$Xaa$_{109}$EIKR |

Wherein the Xaa₂ at position 2 is Val or Ile
Wherein the: Xaa₇ at position 7 is Ser or Thr
Wherein the Xaa₁₄ at position 14 is Thr or Ser
Wherein the Xaa₁₅ at position 15 is Leu or Pro
Wherein the Xaa₃₀ at position 30 is Ile or Val
Wherein the Xaa₅₀ at position 50 is Arg, Gln, or Lys
Wherein the Xaa₈₈ at position 88 is Val or Leu
Wherein the: Xaa₁₀₅ at position 105 is Gln or Gly
Wherein the: Xaa₁₀₈ at position 108 is Lys or Arg
Wherein the Xaa₁₀₉ at position 109 is Val or Leu

```
HCVR of exemplified anti-Aβ antibody
                                         SEQ ID NO. 46
Xaa₁VQLVEXaa₇GGGLVQPGGSLRLSCAASGFTFSRYSMSWVRQA PGKGLXaa₄₆LVAQINSVGNSTYYPDXaa₆₃VKGRFTISRDNXaa₇₅

Xaa₇₆NTLYLQMNSLRAXaa₈₉DTAVYY CASGD YWGQGTXaa₁₀₇V

TVSS
```

Wherein the Xaa₁ at position 1 is Glu or Gln
Wherein the Xaa₇ at position 7 is Ser or Leu
Wherein the Xaa₄₆ at position 46 is Glu, Val, Asp or Ser
Wherein the Xaa₆₃ at position 63 is Thr or Ser
Wherein the Xaa at position 75 is Ala, Ser, Val or Thr
Wherein the Xaa at position 76 is Lys or Arg
Wherein the Xaa at position 89 is Glu or Asp
Wherein the Xaa at position 107 is Leu or Thr

```
LCVR of exemplified anti-Aβ antibody
                                         SEQ ID NO. 47
DVVMTQSPLSLPVTLGQPASISCRSSQSLIYSDGNAYLHWFLQKPG

QSPRLLIYKVSNRFSGVPDRFSGSGSGTDFTLKISRVEAEDVGVYY

CSQSTHVPWTFGQGTKVEIKR

HCVR of exemplified anti-Aβ antibody
                                         SEQ ID NO. 48
EVQLVESGGGLVQPGGSLRLSCAASGFTFSRYSMSWVRQAPGKGLE

LVAQINSVGNSTYYPDTVKGRFTISRDNAKNTLYLQMNSLRAEDTA

VYYCASGDYWGQGTLVTVSS

LC of exemplified anti-Aβ antibody
                                         SEQ ID NO. 49
DVVMTQSPLSLPVTLGQPASISCRSSQSLIYSDGNAYLHWFLQKPG

QSPRLLIYKVSNRFSGVPDRFSGSGSGTDFTLKISRVEAEDVGVYY

CSQSTHVPWTFGQGTKVEIKRTVAAPSVFIFPPSDEQLKSGTASVV

CLLNNFYPREAKVQWKVDNALQSGNSQESVTEQDSKDSTYSLSSTL

TLSKADYEKHKVYACEVTHQGLSSPVTKSFNRGEC

HC of exemplified anti-Aβ antibody
                                         SEQ ID NO. 50
EVQLVESGGGLVQPGGSLRLSCAASGFTFSRYSMSWVRQAPGKGLE

LVAQINSVGNSTYYPDTVKGRFTISRDNAKNTLYLQMNSLRAEDTA

VYYCASGDYWGQGTLVTVSSASTKGPSVFPLAPSSKSTSGGTAALG

CLVKDYFPEPVTVSWNSGALTSGVHTFPAVLQSSGLYSLSSVVTVP

SSSLGTQTYICNVNHKPSNTKVDKKVEPKSCDKTHTCPPCPAPELL

GGPSVFLFPPKPKDTLMISRTPEVTCVVVDVSHEDPEVKFNWYVDG

VEVHNAKTKPREEQYNSTYRVVSVLTVLHQDWLNGKEYKCKVSNKA

LPAPIEKTISKAKGQPREPQVYTLPPSRDELTKNQVSLTCLVKGFY

PSDIAVEWESNGQPENNYKTTPPVLDSDGSFFLYSKLTVDKSRWQQ

GNVFSCSVMHEALHNHYTQKSLSLSPGK

3' Primer for VL PCR
                                         SEQ ID NO. 51
tatagagctc aagcttggat ggtgggaaga tggatacagt tggtgc 3' Primer for VH PCR
                                         SEQ ID NO. 52
tatagagctc aagcttccag tggatagach gatggggstg tygttttggc LCVR of exemplified PEG-anti-Aβ Antibody
Fragment
                                         SEQ ID NO. 53
DIVMTQTPLSLSVTPGQPASISCSSSQSLIYSDGNAYLHWYLQKPG

QSPQLLIYKVSNRFSGVPDRFSGSGSGTDFTLKISRVEAEDVGVYY

CTQSTHSPWTFGGGTKVEIK

HCVR of exemplified PEG-anti-Aβ Antibody
Fragment
                                         SEQ ID NO. 54
EVQLVESGGGLVKPGGSLRLSCAASGYTFSRYSMSWVRQAPGKGLE

WVGQININRGCNTYYPDTVKGRFTISRDDSKNTLYLQMNSLKTEDTA

VYYCTTGDFWGQGTLVTVSS
``` wherein, Cys at residue 56 is pegylated with a 20 KD PEG via maleimide linkage

```
HCVR of exemplified PEG-anti-Aβ Antibody Fragment
                                         SEQ ID NO. 55
EVQLVESGGGLVKPGGSLRLSCAASGYTFSRYSMSWVRQAPGKGLEWVGQIN

IRGNNTYYPDTVKGRFTISRDDSKNTLYLQMNSLKTEDTAVYYCTTGDFWGQ

GTLVTVSS amino acid residues 13-28 of Aβ peptide
                                         SEQ ID NO. 56
HHQKLVFFAEDVGSNK amino acid residues 14-28 of Aβ peptide
                                         SEQ ID NO. 57
HQKLVFFAEDVGSNK LCDR1 of exemplified PEG-anti-Aβ Antibody Fragment
                                         SEQ ID NO. 58
SSSQSLIYSDGNAYLH
```

-continued

LCDR2 of exemplified PEG-anti-Aβ Antibody Fragment
SEQ ID NO. 59
KVSNRFS

LCDR3 of exemplified PEG-anti-Aβ Antibody Fragment
SEQ ID NO. 60
TQSTHSPWT

HCDR1 of exemplified PEG-anti-Aβ Antibody Fragment
SEQ ID NO. 61
GYTFSRYSMS

HCVR2 of exemplified PEG-anti-Aβ Antibody Fragment
SEQ ID NO. 62
QINIRGCNTYYPDTVK HCDR2 of exemplified PEG-anti-Aβ Antibody Fragment
SEQ ID NO. 63
QINIRGNNTYYPDTVKG HCDR3 of exemplified PEG-anti-Aβ Antibody Fragment
SEQ ID NO. 64
GDF cDNA encoding LCVR (SEQ ID NO. 53) of exemplified PEG-anti-Aβ Antibody Fragment
SEQ ID NO. 65
gacatcgtta tgactcagac tccattgtcc ttgtctgtta ctccaggtca accagcttct
atttcctgtt cctcctccca atctttgatc tactccgacg gtaacgctta cttgcactgg
tacttgcaaa agcctggtca atccccacaa ttgttgatct acaaggtttc aacagattc
tctggtgttc ctgacagatt ttctggttcc ggttccggta ctgacttcac tttgaagatc
tccagagttg aagctgagga tgttggtgtt tactactgta ctcagtccac tcattcccca
tggacttttg gtggtggtac taaggttgag atcaagagaa ctgttgctgc tccatccgtt
ttcattttcc caccatccga cgaacaattg aagtctggta ctgcttccgt tgtttgtttg
ttgaacaact tctacccaag agaggctaag gttcagtgga aggttgacaa cgctttgcaa
tccggtaact cccaagaatc cgttactgag caagactcta aggactccac ttactccttg
tcctccactt tgactttgtc caaggctgat tacgagaagc acaaggttta cgcttgtgag
gttacacatc agggtttgtc ctccccagtt actaagtcct caacagagg agagtcc cDNA encoding HCVR (SEQ ID NO. 54) of exemplified PEG-anti-Aβ Antibody Fragment
SEQ ID NO. 66
gaggttcagt tggttgaatc tggtggtgga ttggttaagc ctggtggttc tttgagattg
tcctgtgctg cttccggtta cactttctcc agatactcca tgtcctgggt tagacaagct
ccaggaaagg gattggagtg ggttggtcaa atcaacatca gaggttgtaa cacttactac
ccagacactg ttaagggaag attcactatc tccagagatg actccaagaa cactttgtac
ttgcagatga actccttgaa aactgaggac actgctgttt actactgtac tactggtgac
ttttggggac agggaacttt ggttactgtt tcctccgctt ctactaaggg accatccgtt
tttccattgg ctccatcctc taagtctact tccggtggta ctgctgcttt gggatgtttg
gttaaggact acttcccaga gccagttact gtttcttgga actccggtgc tttgacttct
ggtgttcaca ctttcccagc tgttttgcaa tcttccggtt tgtactcctt gtcctccgtt
gttactgttc catcctcttc cttgggtact cagacttaca tctgtaacgt taaccacaag
ccatccaaca ctaaggttga caagaaggtt gaaccaaagt cctctgacaa gactcac LC of exemplified anti-Tau antibody
SEQ ID NO. 67
EIVLTQSPGTLSLSPGERATLSCRSSQSLVHSNQNTYLHWYQQKPGQAPRLLIYKV
DNRFSGIPDRFSGSGSGTDFTLTISRLEPEDFAVYYCSQSTLVPLTFGGGTKVEIK

```
RTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC
```

HC of exemplified anti-Tau antibody  
SEQ ID NO. 68
```
EVQLVQSGAEVKKPGESLKISCKGSGYTFSNYWIEWVRQMPGKGLEWMGEILPGSD

SIKYEKNFKGQVTISADKSISTAYLQWSSLKASDTAMYYCARRGNYVDDWGQGTLV

TVSSASTKGPSVFPLAPCSRSTSESTAALGCLVKDYFPEPVTVSWNSGALTSGVHT

FPAVLQSSGLYSLSSVVTVPSSSLGTKTYTCNVDHKPSNTKVDKRVESKYGPPCPP

CPAPEAAGGPSVFLFPPKPKDTLMISRTPEVTCVVVDVSQEDPEVQFNWYVDGVEV

HNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPP

VLDSDGSFFLYSRLTVDKSRWQEGNVFSCSVMHEALHNHYTQKSLSLSLG
```

LCDR1 of exemplified anti-Tau antibody  
SEQ ID NO. 69
```
RSSQSLVHSNQNTYLH
```

LCDR2 of exemplified anti-Tau antibody  
SEQ ID NO. 70
```
YKVDNRFS
```

LCDR3 of exemplified anti-Tau antibody  
SEQ ID NO. 71
```
SQSTLVPLT
```

HCDR1 of exemplified anti-Tau antibody  
SEQ ID NO. 72
```
KGSGYTFSNYWIE
```

HCDR2 of exemplified anti-Tau antibody  
SEQ ID NO. 73
```
EILPGSDSIKYEKNFKG
```

HCDR3 of exemplified anti-Tau antibody  
SEQ ID NO. 74
```
ARRGNYVDD
```

LCVR of exemplified anti-Tau antibody  
SEQ ID NO. 75
```
EIVLTQSPGTLSLSPGERATLSCRSSQSLVHSNQNTYLHWYQQKPGQAPRLLIYKV

DNRFSGIPDRFSGSGSGTDFTLTISRLEPEDFAVYYCSQSTLVPLTFGGGTKVEIK
```

HCVR of exemplified anti-Tau antibody  
SEQ ID NO. 76
```
EVQLVQSGAEVKKPGESLKISCKGSGYTFSNYWIEWVRQMPGKGLEWMGEILPGSD

SIKYEKNFKGQVTISADKSISTAYLQWSSLKASDTAMYYCARRGNYVDDWGQGTLV

TVSS
```

Nucleotide Sequence Encoding the Exemplified HC (SEQ ID NO: 68)  
SEQ ID NO. 77
```
gaggtgcagctggtgcagtctggagcagaggtgaaaaagcccggggagtctctgaagatctcct gtaaggttctggctacacattcagtaactactggatagagtgggtgcgccagatgcccgggaa aggcctggagtggatgggggagatatacctggaagtgatagtattaagtacgaaaagaatttca agggccaggtcaccatctcagccgacaagtccatcagcaccgcctacctgcagtggagcagcct gaaggcctcggacaccgccatgtattactgtgcgagaaggggggaactacgtggacgactgggc cagggcaccctggtcaccgtctcctcagatctaccaagggcccatcggtatcccgctagcgccc tgctccaggagcacctccgagagcacagccgccctgggctgcctggtcaaggactacttcccg aaccggtgacggtgtcgtggaactcaggcgccctgaccagcggcgtgcacaccaccggctgtc ctacagtcctcaggactctactccctcagcagcgtggtgaccgtgccctccagcagcagggcac gaagacctacacctgcaacgtagatcacaagcccagcaacaccaaggtggacaagagagttgag
```

-continued tccaaatatggtcccccatgcccaccctgcccagcacctgaggccgccggggaccatcagtct tcctgttccccccaaaacccaaggacactctcatgatctcccggacccctgaggtcacgtgcgt ggtggtggacgtgagccaggaagaccccgaggtccagttcaactggtacgtggatggcgtggag gtgcataatgccaagacaaagccgcgggaggagcagttcaacagcacgtaccgtgtggtcagcg tcctcaccgtcctgcaccaggactggctgaacggcaaggagtacaagtgcaaggtctccaacaa aggcctcccgtcctccatcgagaaaaccatctccaaagccaaagggcagccccgagagccacag gtgtacaccctgcccccatcccaggaggagatgaccaagaaccaggtcagcctgacctgcctgg tcaaaggcttctaccccagcgacatcgccgtggagtgggaaagcaatgggcagccggagaacaa ctacaagaccacgcctcccgtgctggactccgacggctcatcacctctacagcaggctaaccgt ggacaagagcaggtggcaggaggggaatgtcttctcatgctccgtgatgcatgaggctctgcac aaccactacacacagaagagcctctccctgtctctgggt Nucleotide Sequence Encoding the Exemplified LC (SEQ ID NO: 67)
SEQ ID NO. 78 gaaattgtgagacgcagtctccaggcaccctgtctagtctccaggggaaagagccaccctctcc tgcagatctagtcagagccttgtacacagtaatcagaacacctatttacattggtaccagcaga aacctggccaggctcccaggctcctcatctataaagttgacaaccgattactggcatcccagac aggacagtggcagtgggtctgggacagacttcactctcaccatcagcagactggagcctgaaga ttttgcagtgtattactgttctcaaagtacactggttccgctcacgttcggcggagggaccaag gtggagatcaaacggaccgtggctgcaccatctgtcttcatcttcccgccatctgatgagcagt tgaaatctggaactgcctctgttgtgtgcctgctgaataacttctatcccagagaggccaaagt acagtggaaggtggataacgccctccaatcgggtaactcccaggagagtgtcacagagcaggac agcaaggacagcacctacagcctcagcagcaccctgacgctgagcaaagcagactacgagaaac acaaagtctacgcctgcgaagtcacccatcagggcctgagctcgcccgtcacaaagagcttcaa caggggagagtgc Amino Acid Sequence of Human, Full-Length Tau
SEQ ID NO. 79

MAEPRQEFEVMEDHAGTYGLGDRKDQGGYTMHQDQEGDTDAGLKESPLQTPT

EDGSEEPGSETSDAKSTPTAEDVTAPLVDEGAPGKQAAAQPHTEIPEGTTAE

EAGIGDTPSLEDEAAGHVTQARMVSKSKDGTGSDDKKAKGADGKTKIATPRG

AAPPGQKGQANATRIPAKTPPAPKTPPSSGEPPKSGDRSGYSSPGSPGTPGS

RSRTPSLPTPPTREPKKVAVVRTPPKSPSSAKSRLQTAPVPMPDLKNVKSKI

GSTENLKHQPGGGKVQIINKKLDLSNVQSKCGSKDNIKHVPGGGSVQIVYKP

VDLSKVTSKCGSLGNIHHKPGGGQVEVKSEKLDFKDRVQSKIGSLDNITHVP

GGGNKKIETHKLTFRENAKAKTDHGAEIVYKSPVVSGDTSPRHLSNVSSTGS

IDMVDSPQLATLADEVSASLAKQGL

---

We claim:

1. A pharmaceutical composition, comprising an anti-N3pGlu Abeta antibody, with one or more pharmaceutically acceptable carriers, diluents, or excipients, in combination with a pharmaceutical composition of anti-Tau antibody, with one or more pharmaceutically acceptable carriers, diluents, or excipients, wherein the anti-Tau antibody comprises a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, wherein the amino acid sequence of LCDR1 is given by SEQ ID NO.69, the amino acid sequence of LCDR2 is given by SEQ ID NO.70, the amino acid sequence of LCDR3 is given by SEQ ID NO.71, the amino acid sequence of HCDR1 is given by SEQ ID NO. 72, the amino acid sequence of HCDR2 is given by SEQ ID NO.73, and the amino acid sequence of HCDR3 is given by SEQ ID NO.74.

2. The pharmaceutical composition of claim 1 wherein the anti-Tau antibody comprises a light chain variable region (LCVR) and a heavy chain variable region (HCVR), wherein the amino acid sequence of the LCVR is given by SEQ ID NO.75 and the amino acid sequence of the HCVR is given by SEQ ID NO.76.

3. The pharmaceutical composition of claim 1 wherein the anti-Tau antibody comprises a light chain (LC) and a heavy chain (HC), wherein the amino acid sequence of the LC is given by SEQ ID NO.67 and the amino acid sequence of the HC is given by SEQ ID NO.68.

4. The pharmaceutical composition of claim 1, wherein the anti-N3pGlu Abeta antibody comprises a light chain variable region (LCVR) and a heavy chain variable region (HCVR), wherein said LCVR comprises LCDR1, LCDR2 and LCDR3 and HCVR comprises HCDR1, HCDR2 and HCDR3 which are selected from the group consisting of:
  a) LCDR1 is SEQ ID NO.17, LCDR2 is SEQ ID NO.18, LCDR3 is SEQ ID NO.19, HCDR1 is SEQ ID NO.20, HCDR2 is SEQ ID NO.22, and HCDR3 is SEQ ID NO.23;
  b) LCDR1 is SEQ ID NO.17, LCDR2 is SEQ ID NO.18, LCDR3 is SEQ ID NO.19, HCDR1 is SEQ ID NO.21, HCDR2 is SEQ ID NO.22, and HCDR3 is SEQ ID NO.24;
  c) LCDR1 is SEQ ID NO.17, LCDR2 is SEQ ID NO.18, LCDR3 is SEQ ID NO.19, HCDR1 is SEQ ID NO.36, HCDR2 is SEQ ID NO.22, and HCDR3 is SEQ ID NO.37;
  d) LCDR1 is SEQ ID NO.4, LCDR2 is SEQ ID NO.6, LCDR3 is SEQ ID NO.7, HCDR1 is SEQ ID NO.1, HCDR2 is SEQ ID NO.2, and HCDR3 is SEQ ID NO.3; and
  e) LCDR1 is SEQ ID NO.4, LCDR2 is SEQ ID NO.5, LCDR3 is SEQ ID NO.7, HCDR1 is SEQ ID NO.1, HCDR2 is SEQ ID NO.2, and HCDR3 is SEQ ID NO.3.

5. The pharmaceutical composition of claim 1, wherein the anti-N3pGlu Abeta antibody comprises a light chain variable region (LCVR) and a heavy chain variable region (HCVR), wherein said LCVR and HCVR are selected from the group consisting of:
  a) LCVR of SEQ ID NO.25 and HCVR of SEQ ID NO.26;
  b) LCVR of SEQ ID NO.25 and HCVR of SEQ ID NO.27;
  c) LCVR of SEQ ID NO.32 and HCVR of SEQ ID NO.34;
  d) LCVR of SEQ ID NO.9 and HCVR of SEQ ID NO.8; and
  e) LCVR of SEQ ID NO.10 and HCVR of SEQ ID NO.8.

6. The pharmaceutical composition of claim 1, wherein the anti-N3pGlu Abeta antibody comprises two light chains (LC) and two heavy chains (HC), wherein each LC and each HC are selected from the group consisting of:
  a) LC of SEQ ID NO.28 and HC of SEQ ID NO.29;
  b) LC of SEQ ID NO.28 and HC of SEQ ID NO.30;
  c) LC of SEQ ID NO.33 and HC of SEQ ID NO.35;
  d) LC of SEQ ID NO.12 and HC of SEQ ID NO.11; and
  e) LC of SEQ ID NO.13 and HC of SEQ ID NO.11.

7. A method of treating a patient having a disease characterized by deposition of amyloid β (Aβ), comprising administering to a patient in need of such treatment an effective amount of an anti-N3pGlu Abeta antibody, in combination with an effective amount of an anti-Tau antibody, wherein the anti-Tau antibody comprises a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, wherein the amino acid sequence of LCDR1 is given by SEQ ID NO.69, the amino acid sequence of LCDR2 is given by SEQ ID NO.70, the amino acid sequence of LCDR3 is given by SEQ ID NO.71, the amino acid sequence of HCDR1 is given by SEQ ID NO. 72, the amino acid sequence of HCDR2 is given by SEQ ID NO.73, and the amino acid sequence of HCDR3 is given by SEQ ID NO.74.

8. The method of claim 7 wherein the anti-Tau antibody comprises a light chain variable region (LCVR) and a heavy chain variable region (HCVR), wherein the amino acid sequence of the LCVR is given by SEQ ID NO.75 and the amino acid sequence of the HCVR is given by SEQ ID NO.76.

9. The method of claim 8 wherein the anti-Tau antibody comprises a light chain (LC) and a heavy chain (HC), wherein the amino acid sequence of the LC is given by SEQ ID NO.67 and the amino acid sequence of the HC is given by SEQ ID NO.68.

10. The method of claim 7, wherein the anti-N3pGlu Abeta antibody comprises a light chain variable region (LCVR) and a heavy chain variable region (HCVR), wherein said LCVR comprises LCDR1, LCDR2 and LCDR3 and HCVR comprises HCDR1, HCDR2 and HCDR3 which are selected from the group consisting of:
  a) LCDR1 is SEQ ID NO.17, LCDR2 is SEQ ID NO.18, LCDR3 is SEQ ID NO.19, HCDR1 is SEQ ID NO.20, HCDR2 is SEQ ID NO.22, and HCDR3 is SEQ ID NO.23;

b) LCDR1 is SEQ ID NO.17, LCDR2 is SEQ ID NO.18, LCDR3 is SEQ ID NO.19, HCDR1 is SEQ ID NO.21, HCDR2 is SEQ ID NO.22, and HCDR3 is SEQ ID NO.24;

c) LCDR1 is SEQ ID NO.17, LCDR2 is SEQ ID NO.18, LCDR3 is SEQ ID NO.19, HCDR1 is SEQ ID NO.36, HCDR2 is SEQ ID NO.22, and HCDR3 is SEQ ID NO.37;

d) LCDR1 is SEQ ID NO.4, LCDR2 is SEQ ID NO.6, LCDR3 is SEQ ID NO.7, HCDR1 is SEQ ID NO.1, HCDR2 is SEQ ID NO.2, and HCDR3 is SEQ ID NO.3; and e) LCDR1 is SEQ ID NO.4, LCDR2 is SEQ ID NO.5, LCDR3 is SEQ ID NO.7, HCDR1 is SEQ ID NO.1, HCDR2 is SEQ ID NO.2, and HCDR3 is SEQ ID NO.3.

11. The method of claim 7, wherein the anti-N3pGlu Abeta antibody comprises a light chain variable region (LCVR) and a heavy chain variable region (HCVR), wherein said LCVR and HCVR are selected from the group consisting of:

a) LCVR of SEQ ID NO.25 and HCVR of SEQ ID NO.26;

b) LCVR of SEQ ID NO.25 and HCVR of SEQ ID NO.27;

c) LCVR of SEQ ID NO.32 and HCVR of SEQ ID NO.34;

d) LCVR of SEQ ID NO.9 and HCVR of SEQ ID NO.8; and e) LCVR of SEQ ID NO.10 and HCVR of SEQ ID NO.8.

12. The method of claim 7, wherein the anti-N3pGlu Abeta antibody comprises a light chain (LC) and a heavy chain (HC), wherein said LC and HC are selected from the group consisting of a) LC of SEQ ID NO.28 and HC of SEQ ID NO.29;
b) LC of SEQ ID NO.28 and HC of SEQ ID NO.30;
c) LC of SEQ ID NO.33 and HC of SEQ ID NO.35;
d) LC of SEQ ID NO.12 and HC of SEQ ID NO.11; and
e) LC of SEQ ID NO.13 and HC of SEQ ID NO.11.

13. The method of claim 7, wherein the anti-N3pGlu Abeta antibody comprises two light chains (LC) and two heavy chains (HC), wherein each LC and each HC are selected from the group consisting of a) LC of SEQ ID NO.28 and HC of SEQ ID NO.29;
b) LC of SEQ ID NO.28 and HC of SEQ ID NO.30;
c) LC of SEQ ID NO.33 and HC of SEQ ID NO.35;
d) LC of SEQ ID NO.12 and HC of SEQ ID NO.11; and
e) LC of SEQ ID NO.13 and HC of SEQ ID NO.11.

14. The method of claim 7, wherein the disease characterized by deposition of Aβ and aberrant tau aggregation is selected from a group consisting of clinical or pre-clinical Alzheimer's disease (AD).

15. The method of claim 7, wherein the disease characterized by deposition of Aβ is selected from prodromal AD, mild AD, moderate AD or severe AD.

16. The method of claim 7, wherein the patient is diagnosed as having a condition selected from prodromal AD, mild AD, moderate AD and severe AD.

17. The method of claim 11, wherein the patient is diagnosed as having a condition selected from prodromal AD, mild AD, moderate AD and severe AD.

18. The method of claim 7, wherein the anti-N3pGlu Abeta antibody and the anti-Tau antibody are administered simultaneously.

19. The method of claim 7, wherein the anti-N3pGlu Abeta antibody is administered prior to the administration of the anti-Tau antibody.

* * * * *